(12) United States Patent
Zhang et al.

(10) Patent No.: US 6,849,643 B2
(45) Date of Patent: Feb. 1, 2005

(54) INDAZOLYL-SUBSTITUTED PYRROLINE COMPOUNDS AS KINASE INHIBITORS

(75) Inventors: Han-Cheng Zhang, Lansdale, PA (US); Bruce Maryanoff, Forest Grove, PA (US); Bruce Conway, Doylestown, PA (US); Kimberly White, North Wales, PA (US); Hong Ye, Lansdale, PA (US); Leonard Robert Hecker, Harleysville, PA (US); David F. McComsey, Warminster, PA (US)

(73) Assignee: Ortho-McNeil Pharmaceutical, Inc., Skillman, NJ (US)

( * ) Notice: Subject to any disclaimer, the term of this patent is extended or adjusted under 35 U.S.C. 154(b) by 0 days.

(21) Appl. No.: 10/013,181

(22) Filed: Dec. 6, 2001

(65) Prior Publication Data

US 2003/0055097 A1 Mar. 20, 2003

Related U.S. Application Data

(60) Provisional application No. 60/254,166, filed on Dec. 8, 2000.

(51) Int. Cl.⁷ ................ A61K 31/4439; A61K 31/4709; A61K 31/4725; C07D 401/14
(52) U.S. Cl. ....................... 514/307; 514/314; 514/339; 546/139; 546/152; 546/275.7
(58) Field of Search ............................. 546/275.7, 139, 546/152; 514/339, 307, 314

(56) References Cited

U.S. PATENT DOCUMENTS

| 5,057,614 A | 10/1991 | Davis et al. |
| 5,624,949 A | 4/1997 | Heath, Jr. et al. |
| 5,721,245 A | 2/1998 | Davis et al. |

FOREIGN PATENT DOCUMENTS

| EP | 1057484 | 12/2000 |
| EP | 1120414 A1 | 8/2001 |
| WO | WO 9517182 | 6/1995 |
| WO | WO 9811102 | 3/1998 |
| WO | WO 00/06564 A1 | 2/2000 |
| WO | WO 00/21927 A2 | 4/2000 |

OTHER PUBLICATIONS

Davis, P.D. et al.: "Inhibitors of Protein Kinase C1.2, 3–Bisarylmaleimides" Journal of Medicinal Chemistry, American Chemical Society. Washington, D.C., U.S. vol. 35, no.1, 1992, pp. 177–184.
PCT Search Report dated Oct. 8, 2003 for PCT/US03/17569.
P. Xia, et al., "J. Clin. Invest.", 1996, 98, 2018.
H. Ishii, et al., "J. Mol. Med.", 1998, 72, 21.
Inoguchi, et al., "Proc. Natl. Acad. Sci. USA", 1992, 89, 11059–11065.
Bastyr III, E.J. and Lu, J., "Diabetes", 1993, 42 (Suppl. 1) 97A.
Hsieh, et al., "Proc. Natl. Acad. Sci. USA", 1991, 88, 9315–9319.
Hsieh, et al., "J. Biol. Chem." 1993, 268, 15118–15126.
Murray, et al., "J. Biol. Chem.", 1993, 268, 15847–15853.
Tamaoki, et al., "Biochem. Biophys. Res. Commun.", 1986, 135, 397–402.
Gross, et al., "Biochem. Pharmacol.", 1990, 40, 343–350.
Prudhomme, "Curr. Pharm Design", 1997, 3, 265–290.
Pindur, et al., "Curr. Med. Chem." 1999, 6, 29–69.
Ruegg, U.T. and Burgess, G.M., "Trends Pharmacol. Sci." 1989, 10, 218–220.
Davis, et al., "FEBS Lett.", 1989, 259, 61–63.
Twoemy, et al., "Biochem Biophys. Res., Commun.", 1990, 171, 1087–1092.
Touilec et al., "J. Biol. Chem" 1991, 266, 15771–15781.
Davis et al., "J. Med. Chem." 1992, 35, 994–1001.
Bit, et al., "J. Med. Chem.", 1993, 26, 21–29.
McGlynn, et al., "J. Cell. Biochem.", 1992, 49, 239–250.
Ward, N.E. and O'Brian, C.A., "Molec. Pharmacol." 1992, 41, 387–392.
Martiny–Baron, et al., "J. Biol. Chem.", 1993, 268, 9194–9197.
Wilkinson et al., "Biochem J.", 1993, 294, 335–337.
Jirousek et al., "J. Med. Chem.", 1996, 39, 2664–2671.
Hong Hu, "Drug Discovery Today", 1996, 1, 438–447.
Geokjian et al., "Curr. Med. Chem." 1999, 6, 877–903.
Mulqueen, M.J., et al., "Agents Actions", 1992, 37, 85–89.
Huang, K.P., "Trends Neurosci.", 1989, 12, 425–432.
Hara, H., et al., "J. Cereb. Blood Flow Metab.", 1990, 10, 646–653.
Shibata, S., et al., "Brain Res.", 1992, 594, 290–294.
Shimohama, S., et al., "Neurology", 1993, 43, 1407–1413.
Rotenberg, S.A. and Weinstein, I.B., "Biochem. Mol. Aspects Sel. Cancer", 1991, 1, 25–73.

(List continued on next page.)

*Primary Examiner*—Joseph K. McKane
*Assistant Examiner*—Rebecca Anderson
(74) *Attorney, Agent, or Firm*—Hal B. Woodrow; Gabriel Lopez

(57) ABSTRACT

The present invention is directed to novel indazolyl-substituted pyrroline compounds of Formula (I):

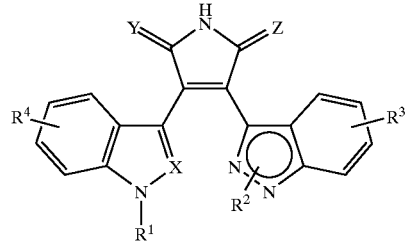

Formula (I)

useful as kinase or dual-kinase inhibitors, methods for producing such compounds and methods for treating or ameliorating a kinase or dual-kinase mediated disorder.

20 Claims, No Drawings

OTHER PUBLICATIONS

Ahmad et al., "Molecular Pharmacology", 1993, 43, 858–862.

Meyer, T., et al., "Int. J. Cancer", 1989, 43, 851–856.

Akinagaka, S., et al., "Cancer Res.", 1991, 51, 4888–4892.

Matsumoto, H. and Sasaki Y., "Biochem. Biophys. Res. Commun." 1989, 158, 105–109.

X. Gu et al., "Circ. Res", 199, 75, 926.

H. Wakasaki et al., "Proc. Natl. Acad. Sci. USA", 1997, 94, 9320.

Bilder, G.E., et al., "J. Pharmacol. Exp. Ther.", 1990, 252, 526–530.

Muid, R.E., et al., "FEBS Lett.", 1990, 293, 169–172.

Sonoki, H., et al., "Kokyu–To Junkan", 1989, 37 669–674.

Horn, F., et al., "J. Invest Dermatol", 1987, 88, 220–222.

Raynaud, F. and Evain–Brion, D., "Br. J. Dermatol.", 1991, 124, 542–546.

Hegemann, L., et al., "Arch. Dermatol. Res.", 1991, 283, 456–460.

Bollag, W.B. et al., "J. Invest. Dermatol.", 1993, 100, 240–246.

Karasik, A., et al., "J. Biol. Chem.", 1990, 265, 10226–10231.

Chen, K.S., et al., "Trans. Assoc. Am. Physicians.", 1991, 104, 206–212.

Chin, J.E., et al., "J. Biol. Chem.", 1993, 268, 6338–6347.

Lee, T–S., et al., "J. Clin. Invest.", 1989, 83, 90–94.

Lee, T–S., et al., "Proc. Natl. Acad. Sci. USA", 1989, 86, 5141–5145.

Craven, P.A. and DeRubertis, F.R., "J. Clin. Invest.", 1989, 87, 1667–1675.

Tesfamariam, B., et al., "J. Clin. Invest.", 1991, 87, 1643–1648.

G. Xie, et al., "Tetrahedron Lett.", 1994, 35, 5555.

Wolf, B.A., et al., J. Clin. Invest., 1991, 87, 31–35.

INDAZOLYL-SUBSTITUTED PYRROLINE COMPOUNDS AS KINASE INHIBITORS

This application claims benefit of provisional application Ser. No. 60/254,166, filed Dec. 8, 2000, which is hereby incorporated by reference.

FIELD OF THE INVENTION

This invention is directed to certain novel compounds, methods for producing them and methods for treating or ameliorating a kinase or dual-kinase mediated disorder. More particularly, this invention is directed to indazolyl-substituted pyrroline compounds useful as selective kinase or dual-kinase inhibitors, methods for producing such compounds and methods for treating or ameliorating a kinase or dual-kinase mediated disorder.

BACKGROUND OF THE INVENTION

U.S. Pat. No. 5,057,614 to Davis, et. al., describes substituted pyrrole compounds of formula I:

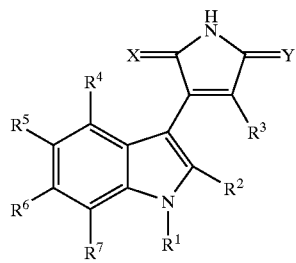

wherein $R^1$ signifies hydrogen, alkyl, aryl (limited to phenyl), aralkyl (limited to phenylalkyl), alkoxyalkyl, hydroxyalkyl, haloalkyl, aminoalkyl, monoalkylaminoalkyl, dialkylaminoalkyl, trialkylaminoalkyl, aminoalkyl- aminoalkyl, azidoalkyl, acylaminoalkyl, acylthioalkyl, alkylsulphonylaminoalkyl, arylsulphonylaminoalkyl, mercaptoalkyl, alkylthioalkyl, alkylsulphinylalkyl, alkylsulphonylalkyl, alkylsulphonyloxyalkyl, alkylcarbonyloxyalkyl, cyanoalkyl, amidinoalkyl, isothiocyanatoalkyl, glucopyranosyl, carboxyalkyl, alkoxycarbonylalkyl, aminocarbonylalkyl, hydroxyalkylthioalkyl, mercaptoalkylthioalkyl, arylthioalkyl or carboxyalkylthioalkyl or a group of the formula

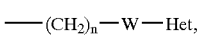 (a)

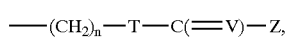 (b)

 (c)

 (d)

in which Het signifies a heterocyclyl group, W signifies NH, S or a bond, T signifies NH or S, V signifies O, S, NH, $NNO_2$, NCN OR $CHNO_2$, Z signifies alkylthio, amino, monoalkylamino or dialkylamino, Im signifies 1-imidazolyl, Ar signifies aryl, and n stands for 2–6; $R^2$ signifies hydrogen, alkyl, aralkyl, alkoxyalkyl, hydroxyalkyl, haloalkyl, aminoalkyl, monoalkylaminoalkyl, dialkylaminoalkyl, acylaminoalkyl, alkylsulphonylaminoalkyl, arylsulphonylaminoalkyl, mercaptoalkyl, alkylthioalkyl, carboxyalkyl, alkoxycarbonylalkyl, aminocarbonylalkyl, alkylthio or alkylsulphinyl; $R^3$ signifies a carbocyclic or heterocyclic aromatic group; $R^4$, $R^5$, $R^6$ and $R^7$ each independently signify hydrogen, halogen, hydroxy, alkoxy, aryloxy, haloalkyl, nitro, amino, acylamino, monoalkylamino, dialkylamino, alkylthio, alkylsulphinyl or alkylsulphonyl; and one of X and Y signifies O and the other signifies O, S, (H,OH) or (H,H); with the proviso that $R^1$ has a significance different from hydrogen when $R^2$ signifies hydrogen, $R^3$ signifies 3-indolyl or 6-hydroxy-3-indolyl, $R^4$, $R^5$ and $R^7$ each signify hydrogen, $R^6$ signifies hydrogen or hydroxy and X and Y both signify O and when $R^2$ signifies hydrogen, $R^3$ signifies 3-indolyl, $R^4$, $R^5$, $R^6$ and $R^7$ each signify hydrogen, X signifies (H,H) and Y signifies O; as well as pharmaceutically acceptable salts of acidic compounds of formula I with bases and of basic compounds of formula I with acids, as therapeutically active substances for the use in control or prevention of inflammatory, immunological, bronchopulmonary and cardiovascular disorders.

The novel compounds of the present invention are structurally unlike those disclosed by the Davis U.S. Pat. No. 5,057,614. In particular, the Davis U.S. Pat. No. 5,057,614 discloses indolyl substituted pyrrole compounds of formula I which may be further substituted on the $R^3$ position with a carbocyclic or heterocyclic aromatic group. The carbocyclic aromatic group denoted by $R^3$ can be a monocyclic or polycyclic group, preferably a monocyclic or bicyclic group, i.e. phenyl or naphthyl, which can be substituted or unsubstituted, for example, with one or more, preferably one to three, substituents selected from halogen, alkyl, hydroxy, alkoxy, haloalkyl, nitro, amino, acylamino, monoalkylamino, dialkylamino, alkylthio, alkylsulphinyl and alkylsulphonyl. Unlike compounds of the present invention, examples of carbocyclic aromatic groups denoted in the Davis '614 patent by $R^3$ are phenyl, 2-, 3-, or 4-chlorophenyl, 3-bromophenyl, 2- or 3-methylphenyl, 2,5-dimethylphenyl, 4-methoxyphenyl, 2- or 3-trifluoromethylphenyl, 2-, 3-, or 4-nitrophenyl, 3-, or 4-aminophenyl, 4-methylthiophenyl, 4-methylsulphinylphenyl, 4-methylsulphonylphenyl and 1-, or 2-naphthyl. The heterocyclic aromatic group denoted by $R^3$ can be a 5- or 6-membered heterocyclic aromatic group which can optionally carry a fused benzene ring and which can be substituted or unsubstituted, for example, with one or more, preferably one to three, substituents selected from halogen, alkyl, hydroxy, alkoxy, haloalkyl, nitro, amino, acylamino, mono- or dialkylamino, alkylthio, alkylsulphinyl and alkylsulphonyl. Unlike compounds of the present invention, examples of heterocyclic aromatic groups denoted in the Davis '614 patent by $R^3$ are 2-, or 3-thienyl, 3-benzothienyl, 1-methyl-2-pyrrolyl, 1-benzimidazolyl, 3-indolyl, 1- or 2-methyl-3-indolyl, 1-methoxymethyl-3-indolyl, 1-(1-methoxyethyl)-3-indolyl, 1-(2-hydroxypropyl)-3-indolyl, 1-(4-hydroxybutyl)-3-indolyl, 1-[1-(2-hydroxyethylthio)ethyl]-3-indolyl, 1-[1-(2-mercaptoethylthio)ethyl]-3-indolyl, 1-(1-phenylthioethyl)-3-indolyl, 1-[1-(carboxymethylthio)ethyl]-3-indolyl and 1-benzyl-3-indolyl.

U.S. Pat. No. 5,721,245 to Davis, et. al., describes substituted 4-[3-indolyl]-1H-pyrrolone compounds of formula I:

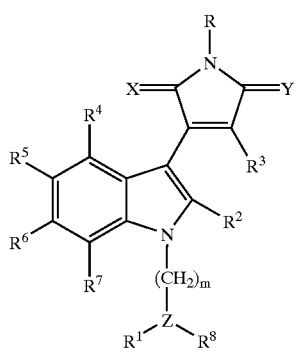

wherein R is hydrogen or hydroxy, $R^1$ and $R^2$ taken together are a group of the formula —$(CH_2)_n$— and $R^7$ is hydrogen or $R^1$ and $R^7$ taken together are a group of the formula —$(CH_2)_n$— and $R^2$ is hydrogen; $R^3$ is an aryl or aromatic heterocyclic group; $R^4$, $R^5$ and $R^6$ each independently are hydrogen, halogen, alkyl, hydroxy, alkoxy, haloalkyl, nitro, amino, acylamino, alkylthio, alkylsulfinyl or alkylsulfonyl; $R^8$ is a group of the formula —$(CH_2)_p$—$R^9$ or —$(CH_2)_q$—$R^{10}$; $R^9$ is hydrogen, alkylcarbonyl, aminoalkylcarbonyl, cyano, amidino, alkoxycarbonyl, aryloxycarbonyl, alkylsulfonyl, aminocarbonyl or aminothiocarbonyl; $R^{10}$ is hydroxy, alkoxy, halogen, amino, monoalkylamino, dialkylamino, trialkylamino, azido, acylamino, alkylsulfonylamino, arylsulfonylamino, alkylthio, alkoxycarbonylamino, aminoacylamino, aminocarbonylamino, isothiocyanato, alkylcarbonyloxy, alkylsulfonyloxy or arylsulfonyloxy, a 5- or 6-membered saturated nitrogen-containing heterocycle attached via the nitrogen atom or a group of the formula —U—C(V)—W; U is S or NH; V is NH, $NNO_2$, NCN, $CHNO_2$; W is amino, monoalkylamino or dialkylamino; one of X and Y is O and the other is O or (H,H); Z is CH or N; m, p and q are, independently, an integer from 0 to 5, and n is an integer from 1 to 5, with the proviso that q and m are, independently, 2 to 5 when Z is N; as well as pharmaceutically acceptable salts of acidic compounds of formula I with bases and of basic compounds of formula I with acids, as therapeutically active substances for use in control or prevention of inflammatory, immunological, bronchopulmonary and cardiovascular disorders.

The novel compounds of the present invention are structurally unlike those disclosed by the Davis U.S. Pat. No. 5,721,245. In particular, the Davis U.S. Pat. No. 5,721,245 discloses 4-[3-indolyl]-1H-pyrrolone compounds of formula I which may be further substituted on the $R^3$ position with an aryl or aromatic heterocyclic group. The term "aryl", alone or in combination denotes a monocyclic or polycyclic group, preferably a monocyclic or bicyclic group, for example, phenyl or naphthyl, which can be substituted or unsubstituted, for example, with one or more, preferably one to three, substituents selected from halogen, alkyl, hydroxy, alkoxy, haloalkyl, nitro, amino, acylamino, alkylthio, alkylsulfinyl and alkylsulfonyl. Unlike compounds of the present invention, examples of such aryl groups in the Davis '245 patent are phenyl, 2-chlorophenyl, 3-chlorophenyl, 4-chlorophenyl, 3-bromophenyl, 2-methylphenyl, 3-methylphenyl, 2,5-dimethylphenyl, 4-methoxyphenyl, 2-trifluoromethylphenyl, 3-trifluoromethyl phenyl, 2-nitrophenyl, 3-nitrophenyl, 4-nitrophenyl, 3-aminophenyl, 4-aminophenyl, 4-methylthiophenyl, 4-methylsulfinylphenyl, 4-methylsulfonylphenyl, 1-naphthyl, 2-naphthyl and the like. The term "aromatic heterocyclic" means a 5- or 6-membered heterocyclic aromatic group which can optionally carry a fused benzene ring and which can be substituted or unsubstituted, for example, with one or more, preferably one to three, substituents selected from halogen, alkyl, hydroxy, alkoxy, haloalkyl, nitro, amino, acylamino, alkylthio, alkylsulfinyl and alkylsulfonyl. Unlike compounds of the present invention, examples of such heterocyclic groups in the Davis '245 patent are 2-thienyl, 3-thienyl, 3-benzothienyl, 3-benzofuranyl, 2-pyrrolyl, 3-indolyl and the like which can be unsubstituted or substituted in the manner indicated. The 5- or 6-membered saturated nitrogen containing heterocycle attached via the nitrogen atom can contain an additional nitrogen or oxygen or a sulfur atom, examples of such heterocycles are pyrrolidino, piperidino, piperazino, morpholino and thiomorpholino.

U.S. Pat. No. 5,624,949 to Heath, Jr., et. al., describes bis-indolemaleimide derivatives of the formula:

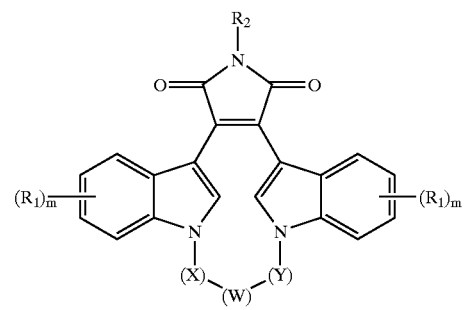

wherein W is —O—, —S—, —SO—, $SO_2$—, —CO—, $C_2$-$C_6$ alkylene, substituted alkylene, $C_2$-$C_6$ alkenylene, -aryl-, -aryl$(CH_2)_m$O—, -heterocycle-, -heterocycle-$(CH_2)_m$O—, -fused bicyclic-, -fused bicyclic-$(CH_2)_m$O—, —$NR_3$—, —$NOR_3$—, —CONH— or —NHCO—; X and Y are independently $C_1$-$C_4$ alkylene, substituted alkylene, or together, X, Y and W combine to form $(CH_2)_n$-AA-; $R_1$ is independently hydrogen, halo, $C_1$-$C_4$ alkyl, hydroxy, $C_1$-$C_4$ alkoxy, haloalkyl, nitro, $NR_4R_5$ or —NHCO($C_1$-$C_4$)alkyl; $R_2$ is hydrogen, $CH_3CO$—, $NH_2$ or hydroxy; $R_3$ is hydrogen, $(CH_2)_m$aryl, $C_1$-$C_4$ alkyl, —COO($C_1$-$C_4$ alkyl), —$CONR_4R_5$, —C(C=NH)$NH_2$, —SO($C_1$-$C_4$ alkyl), —$SO_2(NR_4R_5)$ or —$SO_2(C_1$-$C_4$ alkyl); $R_4$ and $R_5$ are independently hydrogen, $C_1$-$C_4$ alkyl, phenyl, benzyl, or combine to the nitrogen to which they are bonded to form a saturated or unsaturated 5 or 6 member ring; AA is an amino acid residue; m is independently 0, 1, 2 or 3; and n is independently 2, 3, 4 or 5 as protein kinase C (PKC) inhibitors and as selective PKCβ-I and PKCβ-II inhibitors.

Patent application WO 00/06564 discloses disubstituted maleimide compounds of Formula (I):

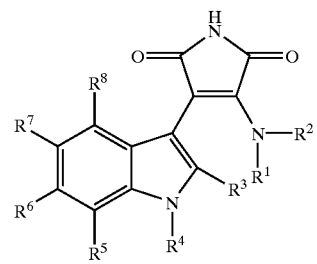

wherein $R^1$ represents hydrogen or alkyl; $R^2$ represents aryl, cycloalkyl or a heterocycle; $R^3$, $R^5$, $R^6$, $R^7$ and $R^8$ represent each hydrogen, halogen, hydroxy, amino, alkyl or alkoxy; and $R^4$ is W, or $R^4$ and $R^3$ or $R^4$ and $R^5$ may form together a ring substituted by W thereon; wherein W represents —$(CH_2)_l$—$(Y)_m$—$(CH_2)_n$—Z as PKCβ inhibitors.

Patent application WO 00/21927 describes 3-amino-4-arymaleimide compounds having formula (I):

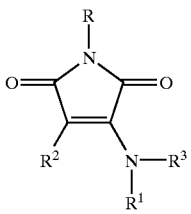

or a pharmaceutically acceptable derivative thereof, wherein: R is hydrogen, alkyl, aryl or aralkyl; $R^1$ is hydrogen, alkyl, aralkyl, hydroxyalkyl or alkoxyalkyl; $R^2$ is substituted or unsubstituted aryl or substituted or unsubstituted heterocyclyl; $R^3$ is hydrogen, substituted or unsubstituted alkyl, cycloalkyl, alkoxyalkyl, substituted or unsubstituted aryl, substituted or unsubstituted heterocyclyl or aralkyl wherein the aryl moiety is substituted or unsubstituted; or, $R^1$ and $R^3$ together with the nitrogen to which they are attached form a single or fused, optionally substituted, saturated or unsaturated heterocyclic ring and a method for the treatment of conditions associated with a need for inhibition of GSK-3, such as diabetes, dementias such as Alzheimer's disease and manic depression.

The indazolyl-substituted pyrroline compounds of the present invention have not been heretofore disclosed.

Accordingly, it is an object of the present invention to provide indazolyl-substituted pyrroline compounds useful as a kinase or dual-kinase inhibitor (in particular, a kinase selected from protein kinase C or glycogen synthase kinase-3; and, more particularly, a kinase selected from protein kinase Cα, protein kinase Cβ-II, protein kinase Cγ or glycogen synthase kinase-3β), methods for their production and methods for treating or ameliorating a kinase or dual-kinase mediated disorder.

SUMMARY OF THE INVENTION

The present invention is directed to indazolyl-substituted pyrroline compounds of Formula (I)

Formula (I)

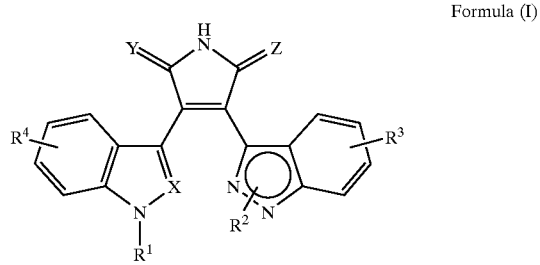

wherein $R^1$ and $R^2$ are independently selected from the group consisting of: hydrogen, $C_{1-8}$alkyl, $C_{2-8}$alkenyl, $C_{2-8}$alkynyl {wherein alkyl, alkenyl and alkynyl are optionally substituted with one to two substituents independently selected from the group consisting of —O—($C_{1-8}$)alkyl, —O—($C_{1-8}$)alkyl-OH, —O—($C_{1-8}$)alkyl-O—($C_{1-8}$)alkyl, —O—($C_{1-8}$)alkyl-NH$_2$, —O—($C_{1-8}$)alkyl-NH—($C_{1-8}$)alkyl, —O—($C_{1-8}$)alkyl-N[($C_{1-8}$)alkyl]$_2$, —O—($C_{1-8}$)alkyl-S—($C_{1-8}$)alkyl, —O—($C_{1-8}$)alkyl-SO$_2$—($C_{1-8}$)alkyl, —O—($C_{1-8}$)alkyl-SO$_2$—NH$_2$, —O—($C_{1-8}$)alkyl-SO$_2$—NH—($C_{1-8}$)alkyl, —O—($C_{1-8}$)alkyl-SO$_2$—N[($C_{1-8}$)alkyl]$_2$, —O—C(O)H, —O—C(O)—($C_{1-8}$)alkyl, —O—C(O)—NH$_2$, —O—C(O)—NH—($C_{1-8}$)alkyl, —O—C(O)—N[($C_{1-8}$)alkyl]$_2$, —O—($C_{1-8}$)alkyl-C(O)H, —O—($C_{1-8}$)alkyl-C(O)—($C_{1-8}$)alkyl, —O—($C_{1-8}$)alkyl-CO$_2$H, —O—($C_{1-8}$)alkyl-C(O)—O—($C_{1-8}$)alkyl, —O—($C_{1-8}$)alkyl-C(O)—NH$_2$, —O—($C_{1-8}$)alkyl-C(O)—NH—($C_{1-8}$)alkyl, —O—($C_{1-8}$)alkyl-C(O)—N[($C_{1-8}$)alkyl]$_2$, —C(O)H, —C(O)—($C_{1-8}$)alkyl, —CO$_2$H, —C(O)—O—($C_{1-8}$)alkyl, —C(O)—NH$_2$, —C(NH)—NH$_2$, —C(O)—NH—($C_{1-8}$)alkyl, —C(O)—N[($C_{1-8}$)alkyl]$_2$, —SH, —S—($C_{1-8}$)alkyl, —S—($C_{1-8}$)alkyl-S—($C_{1-8}$)alkyl, —S—($C_{1-8}$)alkyl-O—($C_{1-8}$)alkyl, S—($C_{1-8}$)alkyl-O—($C_{1-8}$)alkyl-OH, —S—($C_{1-8}$)alkyl-O—($C_{1-8}$)alkyl-NH$_2$, —S—($C_{1-8}$)alkyl-O—($C_{1-8}$)alkyl-NH—($C_{1-8}$)alkyl, —S—($C_{1-8}$)alkyl-O—($C_{1-8}$)alkyl-N[($C_{1-8}$)alkyl]$_2$, —S—($C_{1-8}$)alkyl-NH—($C_{1-8}$)alkyl, —SO$_2$—($C_{1-8}$)alkyl, —SO$_2$—NH$_2$, —SO$_2$—NH—($C_{1-8}$)alkyl, —SO$_2$—N[($C_{1-8}$)alkyl]$_2$, amino (substituted with two substituents independently selected from the group consisting of hydrogen, $C_{1-8}$alkyl, $C_{2-8}$alkenyl, $C_{2-8}$alkynyl, —($C_{1-8}$)alkyl-OH, —($C_{1-8}$)alkyl-O—($C_{1-8}$)alkyl, —($C_{1-8}$)alkyl-NH$_2$, —($C_{1-8}$)alkyl-NH—($C_{1-8}$)alkyl, —($C_{1-8}$)alkyl-N[($C_{1-8}$)alkyl]$_2$, —($C_{1-8}$)alkyl-S—($C_{1-8}$)alkyl, —C(O)—($C_{1-8}$)alkyl, —C(O)—O—($C_{1-8}$)alkyl, —C(O)—NH$_2$, —C(O)—NH—($C_{1-8}$)alkyl, —C(O)—N[($C_{1-8}$)alkyl]$_2$, —SO$_2$—($C_{1-8}$)alkyl, —SO$_2$—NH$_2$, —SO$_2$—NH—($C_{1-8}$)alkyl, —SO$_2$—N[($C_{1-8}$)alkyl]$_2$, —C(N)—NH$_2$, aryl and aryl($C_{1-8}$)alkyl (wherein aryl is optionally substituted with one to three substituents independently selected from the group consisting of halogen, $C_{1-8}$alkyl, $C_{1-8}$alkoxy, amino (substituted with two substituents selected from the group consisting of hydrogen and $C_{1-8}$alkyl), cyano, halo, (halo)$_{1-3}$($C_{1-8}$)alkyl, (halo)$_{1-3}$($C_{1-8}$)alkoxy, hydroxy, hydroxy($C_{1-8}$)alkyl and nitro)), cyano, (halo)$_{1-3}$, hydroxy, nitro, oxo, heterocyclyl, aryl and heteroaryl (wherein heterocyclyl, aryl and heteroaryl are optionally substituted with one to three substituents independently selected from the group consisting of $C_{1-8}$alkyl, $C_{1-8}$alkoxy, amino (substituted with two substituents selected from the group consisting of hydrogen and $C_{1-8}$alkyl), cyano, halo, (halo)$_{1-3}$($C_{1-8}$)alkyl, (halo)$_{1-3}$($C_{1-8}$)alkoxy, hydroxy, hydroxy($C_{1-8}$)alkyl and nitro)}, —C(O)—($C_{1-8}$)alkyl, —C(O)-aryl, —C(O)—O—($C_{1-8}$)alkyl, —C(O)—O-aryl, —C(O)—NH—($C_{1-8}$)alkyl, —C(O)—NH-aryl, —C(O)—N[($C_{1-8}$)alkyl]$_2$, —SO$_2$—($C_{1-8}$)alkyl, —SO$_2$-aryl, aryl and heteroaryl {wherein aryl and heteroaryl are optionally substituted with one to three substituents independently selected from the group consisting of $C_{1-8}$alkyl, $C_{2-8}$alkenyl, $C_{2-8}$alkynyl, $C_{1-8}$alkoxy, —C(O)H, —C(O)—($C_{1-8}$)alkyl, —CO$_2$H, —C(O)—O—($C_{1-8}$)alkyl, —C(O)—NH$_2$, —C(NH)—NH$_2$, —C(O)—NH—($C_{1-8}$)alkyl, —C(O)—N[($C_{1-8}$)alkyl]$_2$, —SH, —S—($C_{1-8}$)alkyl, —SO$_2$—($C_{1-8}$)alkyl, —SO$_2$—NH$_2$, —SO$_2$—NH—($C_{1-8}$)alkyl, —SO$_2$—N[($C_{1-8}$)alkyl]$_2$, amino (substituted with two substituents independently selected from the group consisting of hydrogen, $C_{1-8}$alkyl, $C_{2-8}$alkenyl, $C_{2-8}$alkynyl, —($C_{1-8}$)alkyl-NH$_2$, —C(O)—($C_{1-8}$)alkyl, —C(O)—O—($C_{1-8}$)alkyl, —C(O)—NH$_2$, —C(O)—NH—($C_{1-8}$)alkyl, —C(O)—N[($C_{1-8}$)alkyl]$_2$, —SO$_2$—($C_{1-8}$)alkyl, —SO$_2$—NH$_2$, —SO$_2$—NH—($C_{1-8}$)alkyl, —SO$_2$—N[($C_{1-8}$)alkyl]$_2$ and —C(NH)—NH$_2$), amino-($C_{1-8}$)alkyl- (wherein amino is substituted with two substituents independently selected from the group consisting of hydrogen, $C_{1-8}$alkyl, $C_{2-8}$alkenyl, $C_{2-8}$alkynyl, —($C_{1-8}$)alkyl-NH$_2$, —C(O)—($C_{1-8}$)alkyl, —C(O)—O—($C_{1-8}$)alkyl, —C(O)—NH$_2$, —C(O)—NH—($C_{1-8}$)alkyl, —C(O)—N[($C_{1-8}$)alkyl]$_2$, —SO$_2$—($C_{1-8}$)alkyl, —SO$_2$—NH$_2$, —SO$_2$—NH—($C_{1-8}$)alkyl, —SO$_2$—N[(C$_{1-8}$)alkyl]$_2$ and —C(NH)—NH$_2$), cyano, halo, (halo)$_{1-3}$(C$_{1-8}$)alkyl-, (halo)$_{1-3}$(C$_{1-8}$)alkoxy-, hydroxy, hydroxy(C$_{1-8}$)alkyl, nitro, aryl, —(C$_{1-8}$)alkyl-aryl, heteroaryl and —(C$_{1-8}$)alkyl-heteroaryl};

with the proviso that if R is selected from the group consisting of hydrogen, unsubstituted C$_{1-7}$alkyl and —(C$_{1-7}$)alkyl-(halo)$_{1-3}$, then R$^1$ is selected from the group consisting of other than hydrogen, C$_{1-7}$alkyl, aryl (limited to phenyl unsubstituted or substituted with one or more substituents selected from the group consisting of halo, unsubstituted C$_{1-7}$alkyl, hydroxy, unsubstituted C$_{1-7}$alkoxy, (halo)$_{1-3}$(C$_{1-7}$)alkyl, nitro, unsubstituted amino and cyano), —(C$_{1-7}$)alkyl-aryl (wherein aryl is limited to phenyl unsubstituted or substituted with one or more substituents selected from the group consisting of halo, unsubstituted C$_{1-7}$alkyl, hydroxy, C$_{1-7}$alkoxy, (halo)$_{1-3}$(C$_{1-7}$)alkyl, nitro, unsubstituted amino and cyano), —(C$_{1-7}$)alkyl(C$_{1-7}$)alkoxy, —(C$_{1-7}$)alkyl-hydroxy, —(C$_{1-7}$)alkyl-(halo)$_{1-3}$, —(C$_{1-7}$)alkyl-amino (wherein amino is substituted with two substituents independently selected from the group consisting of hydrogen and —C$_{1-7}$alkyl), —(C$_{1-7}$)alkyl-amino(C$_{1-7}$)alkylamino, —C$_{1-7}$alkyl-NH—C(O)—(C$_{1-7}$)alkyl, —C$_{1-7}$alkyl-NH—SO$_2$—(C$_{1-7}$)alkyl, —(C$_{1-7}$)alkyl-SH, —(C$_{1-7}$)alkyl-S—(C$_{1-7}$)alkyl, —(C$_{1-7}$)alkyl-SO$_2$—(C$_{1-7}$)alkyl, —(C$_{1-7}$)alkyl-O—C(O)—(C$_{1-7}$)alkyl, —(C$_{1-7}$)alkyl-C(N), —(C$_{1-7}$)alkyl-C(NH)—NH$_2$, —(C$_{1-7}$)alkyl-CO$_2$H, —(C$_{1-7}$)alkyl-C(O)—O—(C$_{1-7}$)alkyl, —(C$_{1-7}$)alkyl-C(O)—NH$_2$, —(CH$_2$)$_{2-6}$-heterocyclyl, —(CH$_2$)$_{2-6}$-T-C(V)-Z (wherein T is NH, V is O and Z is amino (wherein amino is substituted with two substituents independently selected from the group consisting of hydrogen and C$_{1-7}$alkyl));

X is selected from the group consisting of N and CR$^5$;

R$^3$ and R$^4$ are independently selected from the group consisting of hydrogen, C$_{1-8}$alkyl, C$_{2-8}$alkenyl, C$_{2-8}$alkynyl, C$_{1-8}$alkoxy, —C(O)H, —C(O)—(C$_{1-8}$)alkyl, —CO$_2$H, —C(O)—O—(C$_{1-8}$)alkyl, —C(O)—NH$_2$, —C(NH)—NH$_2$, —C(O)—NH—(C$_{1-8}$)alkyl, —C(O)—N[(C$_{1-8}$)alkyl]$_2$, —SH, —S—(C$_{1-8}$)alkyl, —SO$_2$—(C$_{1-8}$)alkyl, —SO$_2$—NH$_2$, —SO$_2$—NH—(C$_{1-8}$)alkyl, —SO$_2$—N[(C$_{1-8}$)alkyl]$_2$, amino (substituted with two substituents independently selected from the group consisting of hydrogen, C$_{1-8}$alkyl, C$_{2-8}$alkenyl, C$_{2-8}$alkynyl, —(C$_{1-8}$)alkyl-NH$_2$, —C(O)—(C$_{1-8}$)alkyl, —C(O)—O—(C$_{1-8}$)alkyl, —C(O)—NH$_2$, —C(O)—NH—(C$_{1-8}$)alkyl, —C(O)—N[(C$_{1-8}$)alkyl]$_2$, —SO$_2$—(C$_{1-8}$)alkyl, —SO$_2$—NH$_2$, —SO$_2$—NH—(C$_{1-8}$)alkyl, —SO$_2$—N[(C$_{1-8}$)alkyl]$_2$ and —C(NH)—NH$_2$), amino-(C$_{1-8}$)alkyl- (wherein amino is substituted with two substituents independently selected from the group consisting of hydrogen, C$_{1-8}$alkyl, C$_{2-8}$alkenyl, C$_{2-8}$alkynyl, —(C$_{1-8}$)alkyl-NH$_2$, —C(O)—(C$_{1-8}$)alkyl, —C(O)—O—(0$_{1-8}$)alkyl, —C(O)—NH$_2$, —C(O)—NH—(C$_{1-8}$)alkyl, —C(O)—N[(C$_{1-8}$)alkyl]$_2$, —SO$_2$—(C$_{1-8}$)alkyl, —SO$_2$—NH$_2$, —SO$_2$—NH—(C$_{1-8}$)alkyl, —SO$_2$—N[(C$_{1-8}$)alkyl]$_2$ and —C(NH)—NH$_2$), cyano, halo, (halo)$_{1-3}$(C$_{1-8}$)alkyl-, (halo)$_{1-3}$(C$_{1-8}$)alkoxy-, hydroxy, hydroxy(C$_{1-8}$)alkyl-, nitro, aryl, —(C$_{1-8}$)alkyl-aryl, heteroaryl and —(C$_{1-8}$)alkyl-heteroaryl;

Y and Z are independently selected from the group consisting of O, S, (H,OH) and (H,H); with the proviso that one of Y and Z is O and the other is selected from the group consisting of O, S, (H,OH) and (H,H); and, R$^5$ is selected from the group consisting of hydrogen, halogen, C$_{1-8}$alkyl, C$_{2-8}$alkenyl, C$_{2-8}$alkynyl {wherein alkyl, alkenyl and alkynyl are optionally substituted with one to two substituents independently selected from the group consisting of amino (substituted with two substituents selected from the group consisting of hydrogen and C$_{1-8}$alkyl), cyano, halo, hydroxy, nitro, oxo, aryl and heteroaryl}, aryl and heteroaryl {wherein aryl and heteroaryl are optionally substituted with one to two substituents independently selected from the group consisting of C$_{1-8}$alkyl, C$_{1-8}$alkoxy, amino (substituted with two substituents selected from the group consisting of hydrogen and C$_{1-8}$alkyl), cyano, halo, hydroxy and nitro};

and pharmaceutically acceptable salts thereof.

The present invention is directed to indazolyl-substituted pyrroline compounds useful as a selective kinase or dual-kinase inhibitor; in particular, a kinase selected from protein kinase C or glycogen synthase kinase-3; and, more particularly, a kinase selected from protein kinase Cα, protein kinase C β-II, protein kinase Cγ or glycogen synthase kinase-3β.

The present invention Is also directed to methods for producing the instant indazolyl-substituted pyrroline compounds and pharmaceutical compositions and medicaments thereof.

The present invention is further directed to methods for treating or ameliorating a kinase or dual-kinase mediated disorder. In particular, the method of the present invention is directed to treating or ameliorating a kinase or dual-kinase mediated disorder such as, but not limited to, cardiovascular diseases, diabetes, diabetes-associated disorders, inflammatory diseases, immunological disorders, dermatological disorders, oncological disorders and CNS disorders.

DETAILED DESCRIPTION OF THE INVENTION

Preferred embodiments of the present invention include compounds of Formula (I) wherein, R$^1$ and R$^2$ are independently selected from the group consisting of:

hydrogen,

C$_{1-4}$alkyl, C$_{2-4}$alkenyl, C$_{2-4}$alkynyl {wherein alkyl, alkenyl and alkynyl are optionally substituted with one to two substituents independently selected from the group consisting of —O—(C$_{1-4}$)alkyl, —O—(C$_{1-4}$)alkyl-OH, —O—(C$_{1-4}$)alkyl-O—(C$_{1-4}$)alkyl, —O—(C$_{1-4}$)alkyl-NH$_2$, —O—(C$_{1-4}$)alkyl-NH—(C$_{1-4}$)alkyl, —O—(C$_{1-4}$)alkyl-N[(C$_{1-4}$)alkyl]$_2$, —O—(C$_{1-4}$)alkyl-S—(C$_{1-4}$)alkyl, —O—(C$_{1-4}$)alkyl-SO$_2$—(C$_{1-4}$)alkyl, —O—(C$_{1-4}$)alkyl-SO$_2$—NH$_2$, —O—(C$_{1-4}$)alkyl-SO$_2$—NH—(C$_{1-4}$)alkyl, —O—(C$_{1-4}$)alkyl-SO$_2$—N[(C$_{1-4}$)alkyl]$_2$, —O—C(O)H, —O—C(O)—(C$_{1-4}$)alkyl, —O—C(O)—NH$_2$, —O—C(O)—NH—(C$_{1-4}$)alkyl, —O—C(O)—N[(C$_{1-4}$)alkyl]$_2$, —O—(C$_{1-4}$)alkyl-C(O)H, —O—(C$_{1-4}$)alkyl-C(O)—(C$_{1-4}$)alkyl, —O—(C$_{1-4}$)alkyl-CO$_2$H, —O—(C$_{1-4}$)alkyl-C(O)—O—(C$_{1-4}$)alkyl, —O—(C$_{1-4}$)alkyl-C(O)—NH$_2$, —O—(C$_{1-4}$)alkyl-C(O)—NH—(C$_{1-4}$)alkyl, —O—(C$_{1-4}$)alkyl-C(O)—N[(C$_{1-4}$)alkyl]$_2$, —C(O)H, —C(O)—(C$_{1-4}$)alkyl, —CO$_2$H, —C(O)—O—(C$_{1-4}$)alkyl, —C(O)—NH$_2$, —C(NH)—NH$_2$, —C(O)—NH—(C$_{1-4}$)alkyl, —C(O)—N[(C$_{1-4}$)alkyl]$_2$, —SH, —S—(C$_{1-4}$)alkyl, —S—(C$_{1-4}$)alkyl-S—(C$_{1-4}$)alkyl, —S—(C$_{1-4}$)alkyl-O—(C$_{1-4}$)alkyl, —S—(C$_{1-4}$)alkyl-O—(C$_{1-4}$)alkyl-OH, —S—(C$_{1-4}$)alkyl-O—(C$_{1-4}$)alkyl-NH$_2$, —S—(C$_{1-4}$)alkyl-O—(C$_{1-4}$)alkyl-NH—(C$_{1-4}$)alkyl, —S—(C$_{1-4}$)alkyl-O—(C$_{1-4}$)alkyl-N[(C$_{1-4}$)alkyl]$_2$, —S—(C$_{1-4}$)alkyl-NH—(C$_{1-4}$)alkyl, —SO$_2$—(C$_{1-4}$)alkyl, —SO$_2$—NH$_2$, —SO$_2$—NH—(C$_{1-4}$)alkyl, —SO$_2$—N[(C$_{1-4}$)alkyl]$_2$, amino (substituted with two substituents independently selected from the group consisting of hydrogen, C$_{1-4}$alkyl, $C_{2-4}$alkenyl, $C_{2-4}$alkynyl, —($C_{1-4}$)alkyl-OH, —($C_{1-4}$)alkyl-O—($C_{1-4}$)alkyl, —($C_{1-4}$)alkyl-NH$_2$, —($C_{1-4}$)alkyl-NH—($C_{1-4}$)alkyl, —($C_{1-4}$)alkyl-N[($C_{1-4}$)alkyl]$_2$, —($C_{1-4}$)alkyl-S—($C_{1-4}$)alkyl, —C(O)—($C_{1-4}$)alkyl, —C(O)—O—($C_{1-4}$)alkyl, —C(O)—NH$_2$, —C(O)—NH—($C_{1-4}$)alkyl, —C(O)—N[($C_{1-4}$)alkyl]$_2$, —SO$_2$—($C_{1-4}$)alkyl, —SO$_2$—NH$_2$, —SO$_2$—NH—($C_{1-4}$)alkyl, —SO$_2$—N[($C_{1-4}$)alkyl]$_2$, —C(N)—NH$_2$, aryl and aryl($C_{1-4}$)alkyl (wherein aryl is optionally substituted with one to three substituents independently selected from the group consisting of halogen, $C_{1-4}$alkyl, $C_{1-4}$alkoxy, amino (substituted with two substituents selected from the group consisting of hydrogen and $C_{1-4}$alkyl), cyano, halo, (halo)$_{1-3}$($C_{1-4}$)alkyl, (halo)$_{1-3}$($C_{1-4}$)alkoxy, hydroxy, hydroxy($C_{1-4}$)alkyl and nitro)), cyano, (halo)$_{1-3}$, hydroxy, nitro, oxo, heterocyclyl, aryl and heteroaryl (wherein heterocyclyl, aryl and heteroaryl are optionally substituted with one to three substituents independently selected from the group consisting of $C_{1-4}$alkyl, $C_{1-4}$alkoxy, amino (substituted with two substituents selected from the group consisting of hydrogen and $C_{1-4}$alkyl), cyano, halo, (halo)$_{1-3}$($C_{1-4}$)alkyl, (halo)$_{1-3}$($C_{1-4}$)alkoxy, hydroxy, hydroxy($C_{1-4}$)alkyl and nitro)}, —C(O)—($C_{1-4}$)alkyl, —C(O)-aryl, —C(O)—O—($C_{1-4}$)alkyl, —C(O)—O-aryl, —C(O)—NH—($C_{1-4}$)alkyl, —C(O)—NH-aryl, —C(O)—N[($C_{1-4}$)alkyl]$_2$, —SO$_2$—($C_{1-4}$)alkyl, —SO$_2$-aryl, aryl and heteroaryl {wherein aryl and heteroaryl are optionally substituted with one to three substituents independently selected from the group consisting of $C_{1-4}$alkyl, $C_{2-4}$alkenyl, $C_{2-4}$alkynyl, $C_{1-4}$alkoxy, —C(O)H, —C(O)—($C_{1-4}$)alkyl, —CO$_2$H, —C(O)—O—($C_{1-4}$)alkyl, —C(O)—NH$_2$, —C(NH)—NH$_2$, —C(O)—NH—($C_{1-4}$)alkyl, —C(O)—N[($C_{1-4}$)alkyl]$_2$, —SH, —S—($C_{1-4}$)alkyl, —SO$_2$—($C_{1-4}$)alkyl, —SO$_2$—NH$_2$, —SO$_2$—NH—($C_{1-4}$)alkyl, —SO$_2$—N[($C_{1-4}$)alkyl]$_2$, amino (substituted with two substituents independently selected from the group consisting of hydrogen, $C_{1-4}$alkyl, $C_{2-4}$alkenyl, $C_{2-4}$alkynyl, —($C_{1-4}$)alkyl-NH$_2$, —C(O)—($C_{1-4}$)alkyl, —C(O)—O—($C_{1-4}$)alkyl, —C(O)—NH$_2$, —C(O)—NH—($C_{1-4}$)alkyl, —C(O)—N[($C_{1-4}$)alkyl]$_2$, —SO$_2$—($C_{1-4}$)alkyl, —SO$_2$—NH$_2$, —SO$_2$—NH—($C_{1-4}$)alkyl, —SO$_2$—N[($C_{1-4}$)alkyl]$_2$ and —C(NH)—NH$_2$), amino-($C_{1-4}$)alkyl- (wherein amino is substituted with two substituents independently selected from the group consisting of hydrogen, $C_{1-4}$alkyl, $C_{2-4}$alkenyl, $C_{2-4}$alkynyl, —($C_{1-4}$)alkyl-NH$_2$, —C(O)—($C_{1-4}$)alkyl, —C(O)—O—($C_{1-4}$)alkyl, —C(O)—NH$_2$, —C(O)—NH—($C_{1-4}$)alkyl, —C(O)—N[($C_{1-4}$)alkyl]$_2$, —SO$_2$—($C_{1-4}$)alkyl, —SO$_2$—NH$_2$, SO$_2$—NH—($C_{1-4}$)alkyl, —SO$_2$—N[($C_{1-4}$)alkyl]$_2$ and —C(NH)—NH$_2$), cyano, halo, (halo)$_{1-3}$($C_{1-4}$)alkyl, (halo)$_{1-3}$($C_{1-4}$)alkoxy, hydroxy, hydroxy($C_{1-4}$)alkyl, nitro, aryl, —($C_{1-4}$)alkyl-aryl, heteroaryl and —($C_{1-4}$)alkyl-heteroaryl};

with the proviso that if $R^2$ is selected from the group consisting of hydrogen, unsubstituted $C_{1-4}$alkyl and —($C_{1-4}$)alkyl-(halo)$_{1-3}$, then $R^1$ is selected from the group consisting of other than hydrogen, $C_{1-4}$alkyl, aryl (limited to phenyl unsubstituted or substituted with one or more substituents selected from the group consisting of halo, unsubstituted $C_{1-4}$alkyl, hydroxy, $C_{1-4}$alkoxy, (halo)$_{1-3}$($C_{1-4}$)alkyl, nitro, unsubstituted amino and cyano), —($C_{1-4}$)alkyl-aryl (wherein aryl is limited to phenyl unsubstituted or substituted with one or more substituents selected from the group consisting of halo, unsubstituted $C_{1-4}$alkyl, hydroxy, $C_{1-4}$alkoxy, (halo)$_{1-3}$($C_{1-4}$)alkyl, nitro, unsubstituted amino and cyano), —($C_{1-4}$)alkyl ($C_{1-4}$)alkoxy, —($C_{1-4}$)alkyl-hydroxy, —($C_{1-4}$)alkyl-(halo)$_{1-3}$, —($C_{1-4}$)alkyl-amino (wherein amino is substituted with two substituents independently selected from the group consisting of hydrogen and $C_{1-4}$alkyl), —($C_{1-4}$)alkyl-amino($C_{1-4}$)alkylamino, —$C_{1-4}$alkyl-NH—C(O)—($C_{1-4}$)alkyl, —$C_{1-4}$alkyl-NH—SO$_2$—($C_{1-4}$)alkyl, —($C_{1-4}$)alkyl-SH, —($C_{1-4}$)alkyl-S—($C_{1-4}$)alkyl, —($C_{1-4}$)alkyl-SO$_2$—($C_{1-4}$)alkyl, —($C_{1-4}$)alkyl-O—C(O)—($C_{1-4}$)alkyl, —($C_{1-4}$)alkyl-C(N), —($C_{1-4}$)alkyl-C(NH)—NH$_2$, —($C_{1-4}$)alkyl-CO$_2$H, —($C_{1-4}$)alkyl-C(O)—O—($C_{1-4}$)alkyl, —($C_{1-4}$)alkyl-C(O)—NH$_2$, (CH$_2$)$_{2-4}$-heterocyclyl, —(CH$_2$)$_{2-4}$-T-C(V)—Z (wherein T is NH, V is O and Z is amino (wherein amino is substituted with two substituents independently selected from the group consisting of hydrogen and $C_{1-4}$alkyl)).

More preferably, $R^1$ and $R^2$ are independently selected from the group consisting of:

hydrogen, $C_{1-4}C_{2-4}$alkenyl {wherein alkyl is substituted with one to two substituents independently selected from the group consisting of —O—($C_{1-4}$)alkyl, —O—($C_{1-4}$)alkyl-OH, —O—($C_{1-4}$)alkyl-NH—($C_{1-4}$)alkyl, —O—C(O)—($C_{1-4}$)alkyl, —C(O)H, —CO$_2$H, —C(O)—O—($C_{1-4}$)alkyl, amino (substituted with two substituents independently selected from the group consisting of hydrogen, $C_{1-4}$alkyl, —($C_{1-4}$)alkyl-OH, —C(O)—O—($C_{1-4}$)alkyl and aryl ($C_{1-4}$)alkyl), hydroxy, heterocyclyl, aryl and heteroaryl (wherein heterocyclyl, aryl and heteroaryl are optionally substituted with one to three substituents independently selected from the group consisting of $C_{1-4}$alkyl and halo)}, aryl and heteroaryl {wherein aryl and heteroaryl are optionally substituted with one to two substituents independently selected from the group consisting of $C_{1-4}$alkyl, $C_{1-4}$alkoxy, amino (substituted with two substituents independently selected from the group consisting of hydrogen and $C_{1-4}$alkyl), cyano, halo, (halo)$_{1-3}$($C_{1-4}$)alkyl, (halo)$_{1-3}$($C_{1-4}$)alkoxy, hydroxy, hydroxy($C_{1-4}$)alkyl, aryl and heteroaryl};

with the proviso that if $R^2$ is selected from the group consisting of hydrogen and unsubstituted $C_{1-4}$alkyl, then $R^1$ is selected from the group consisting of other than hydrogen, $C_{1-4}$alkyl, aryl (limited to phenyl unsubstituted or substituted with one or more substituents selected from the group consisting of halo, unsubstituted $C_{1-4}$alkyl, hydroxy, $C_{1-4}$alkoxy, (halo)$_{1-3}$($C_{1-4}$)alkyl, unsubstituted amino and cyano), —($C_{1-4}$)alkyl-aryl (wherein aryl is limited to phenyl unsubstituted or substituted with one or more substituents selected from the group consisting of halo and unsubstituted $C_{1-4}$alkyl), —($C_{1-4}$)alkyl($C_{1-4}$)alkoxy, —($C_{1-4}$)alkyl-hydroxy, —($C_{1-4}$)alkyl-amino (wherein amino is substituted with two substituents independently selected from the group consisting of hydrogen and $C_{1-4}$-alkyl), —($C_{1-4}$)alkyl-O—C(O)—($C_{1-4}$)alkyl, —($C_{1-4}$)alkyl-CO$_2$H, —($C_{1-4}$)alkyl-C(O)—O—($C_{1-4}$)alkyl and —(CH$_2$)$_{2-4}$-heterocyclyl.

Preferred embodiments of the present invention include compounds of Formula (I) wherein, $R^1$ is selected from the group consisting of hydrogen, $C_{1-4}$alkyl, $C_{2-4}$alkenyl {wherein alkyl is substituted with one to two substituents independently selected from the group consisting of —O—($C_{1-4}$)alkyl-NH—($C_{1-4}$)alkyl, amino (substituted with two substituents independently selected from the group consisting of hydrogen and $C_{1-4}$alkyl), hydroxy, heterocyclyl, aryl and heteroaryl (wherein heterocyclyl, aryl and heteroaryl are optionally substituted with one to three substituents independently selected from the group consisting of $C_{1-4}$alkyl and halo)}, aryl and heteroaryl {wherein aryl and heteroaryl are optionally substituted with one to two substituents independently selected from the group consisting of $C_{1-4}$alkyl, $C_{1-4}$alkoxy, amino (substituted with two substituents independently selected from the group consisting of hydrogen and $C_{1-4}$alkyl), cyano, halo, (halo)$_{1-3}$($C_{1-4}$)alkyl, (halo)$_{1-3}$($C_{1-4}$)alkoxy, hydroxy, hydroxy($C_{1-4}$)alkyl, aryl and heteroaryl};

with the proviso that if $R^2$ is selected from the group consisting of hydrogen, unsubstituted $C_{1-4}$alkyl and —($C_{1-4}$)alkyl-(halo)$_{1-3}$, then $R^1$ is selected from the group consisting of other than hydrogen, $C_{1-4}$alkyl, aryl (limited to phenyl unsubstituted or substituted with one or more substituents selected from the group consisting of halo, unsubstituted $C_{1-4}$alkyl, hydroxy, $C_{1-4}$alkoxy, (halo)$_{1-3}$($C_{1-4}$)alkyl, unsubstituted amino and cyano), —($C_{1-4}$)alkyl-aryl (wherein aryl is limited to phenyl unsubstituted or substituted with one or more substituents selected from the group consisting of halo and unsubstituted $C_{1-4}$alkyl), —($C_{1-4}$)alkyl-hydroxy, —($C_{1-4}$)alkyl-amino (wherein amino is substituted with two substituents independently selected from the group consisting of hydrogen and $C_{1-4}$alkyl) and —($CH_2$)$_{2-4}$-heterocyclyl.

More preferably, $R^1$ is selected from the group consisting of hydrogen, $C_{1-4}$alkyl, $C_{2-3}$alkenyl {wherein alkyl is substituted with one to two substituents independently selected from the group consisting of —O—($C_{1-4}$)alkyl-NH—($C_{1-4}$)alkyl, amino (substituted with two substituents independently selected from the group consisting of hydrogen and $C_{1-4}$alkyl), hydroxy, pyrrolidinyl, morpholinyl, piperazinyl (wherein piperazinyl is optionally substituted with methyl), phenyl, naphthalenyl, benzo[b]thienyl and quinolinyl (wherein phenyl and benzo[b]thienyl are optionally substituted with one to two chloro substituents)}, phenyl, naphthalenyl, furyl, thienyl, pyridinyl, pyrimidinyl, benzo[b]thienyl, quinolinyl and isoquinolinyl (wherein phenyl, naphthalenyl and pyridinyl are optionally substituted with one to two substituents independently selected from the group consisting of $C_{1-4}$alkyl, $C_{1-4}$alkoxy, halo and hydroxy; and, wherein phenyl is optionally substituted with one substituent selected from the group consisting of phenyl and thienyl);

with the proviso that if $R^2$ is selected from the group consisting of hydrogen, unsubstituted $C_{1-4}$alkyl and —($C_{1-4}$)alkyl-(halo)$_{1-3}$, then $R^1$ is selected from the group consisting of other than hydrogen, $C_{1-4}$alkyl, phenyl (wherein phenyl is unsubstituted or substituted with one or more substituents selected from the group consisting of halo, unsubstituted $C_{1-4}$alkyl, hydroxy and $C_{1-4}$alkoxy), —($C_{1-4}$)alkyl-phenyl (wherein phenyl is unsubstituted or substituted with one or more chloro substituents), —($C_{1-4}$)alkyl-hydroxy, —($C_{1-4}$)alkyl-amino (wherein amino is substituted with two substituents independently selected from the group consisting of hydrogen and $C_{1-4}$alkyl) and —($CH_2$)$_{2-4}$-heterocyclyl.

Preferred embodiments of the present invention include compounds of Formula (I) wherein, $R^2$ is selected from the group consisting of:

hydrogen, $C_{1-4}$alkyl {wherein alkyl is substituted with one to two substituents independently selected from the group consisting of —O—($C_{1-4}$)alkyl, —O—($C_{1-4}$)alkyl-OH, —O—($C_{1-4}$)alkyl-NH—($C_{1-4}$)alkyl, —O—C(O)—($C_{1-4}$)alkyl, —C(O)H, —CO$_2$H, —C(O)—O—($C_{1-4}$)alkyl, amino (substituted with two substituents independently selected from the group consisting of hydrogen, $C_{1-4}$alkyl, —($C_{1-4}$)alkyl-OH, —C(O)—O—($C_{1-4}$)alkyl and aryl ($C_{1-4}$)alkyl), hydroxy and heterocyclyl (wherein heterocyclyl is optionally substituted with one to two $C_{1-4}$alkyl substituents)} and heteroaryl;

with the proviso that if $R^2$ is selected from the group consisting of hydrogen and unsubstituted $C_{1-4}$alkyl, then $R^1$ is selected from the group consisting of other than hydrogen, $C_{1-4}$alkyl, aryl (limited to phenyl unsubstituted or substituted with one or more substituents selected from the group consisting of halo, unsubstituted $C_{1-4}$alkyl, hydroxy, $C_{1-4}$alkoxy, (halo)$_{1-3}$($C_{1-4}$)alkyl, nitro, unsubstituted amino and cyano), —($C_{1-4}$)alkyl-aryl (wherein aryl is limited to phenyl unsubstituted or substituted with one or more substituents selected from the group consisting of halo, unsubstituted $C_{1-4}$alkyl, hydroxy, $C_{1-4}$alkoxy, (halo)$_{1-3}$($C_{1-4}$)alkyl, nitro, unsubstituted amino and cyano), —($C_{1-4}$)alkyl($C_{1-4}$)alkoxy, —($C_{1-4}$)alkyl-hydroxy, —($C_{1-4}$)alkyl-(halo)$_{1-3}$, —($C_{1-4}$)alkyl-amino (wherein amino is substituted with two substituents independently selected from the group consisting of hydrogen and $C_{1-4}$alkyl), —($C_{1-4}$)alkyl-amino($C_{1-4}$)alkylamino, —$C_{1-4}$alkyl-NH—C(O)—($C_{1-4}$)alkyl, —$C_{1-4}$alkyl-NH—SO$_2$—($C_{1-4}$)alkyl, —($C_{1-4}$)alkyl-SH, —($C_{1-4}$)alkyl-S—($C_{1-4}$)alkyl, —($C_{1-4}$)alkyl-SO$_2$—($C_{1-4}$)alkyl, —($C_{1-4}$)alkyl-O-C(O)—($C_{1-4}$)alkyl, —($C_{1-4}$)alkyl-C(N), ($C_{1-4}$)alkyl-C(NH)—NH$_2$, —($C_{1-4}$)alkyl-CO$_2$H, —($C_{1-4}$)alkyl-C(O)—O—($C_{1-4}$)alkyl, —($C_{1-4}$)alkyl-C(O)—NH$_2$, —($CH_2$)$_{2-4}$-heterocyclyl, —($CH_2$)$_{2-4}$-T-C(V)—Z (wherein T is NH, V is O and Z is amino (wherein amino is substituted with two substituents independently selected from the group consisting of hydrogen and $C_{1-4}$alkyl)).

More preferably, $R^2$ is selected from the group consisting of:

hydrogen, $C_{1-4}$alkyl {wherein alkyl is substituted with one to two substituents independently selected from the group consisting of —O—($C_{1-4}$)alkyl, —O—($C_{1-4}$)alkyl-OH, —O—($C_{1-4}$)alkyl-NH—($C_{1-4}$)alkyl, —O—C(O)—($C_{1-4}$)alkyl, —C(O)H, —CO$_2$H, —C(O)—O—($C_{1-4}$)alkyl, amino (substituted with two substituents independently selected from the group consisting of hydrogen, $C_{1-4}$alkyl, —($C_{1-4}$)alkyl-OH, —C(O)—O—($C_{1-4}$)alkyl and phenyl ($C_{1-4}$)alkyl), hydroxy, pyrrolidinyl, 1,3-dioxolanyl, morpholinyl and piperazinyl (wherein piperazinyl is optionally substituted with methyl)} and pyridinyl;

with the proviso that if $R^2$ is selected from the group consisting of hydrogen and unsubstituted $C_{1-4}$alkyl, then $R^1$ is selected from the group consisting of other than hydrogen, $C_{1-4}$alkyl, aryl (limited to phenyl unsubstituted or substituted with one or more substituents selected from the group consisting of halo, unsubstituted $C_{1-4}$alkyl, hydroxy, $C_{1-4}$alkoxy, (halo)$_{1-3}$($C_{1-4}$)alkyl, nitro, unsubstituted amino and cyano), —($C_{1-4}$)alkyl-aryl (wherein aryl is limited to phenyl unsubstituted or substituted with one or more substituents selected from the group consisting of halo, unsubstituted $C_{1-4}$alkyl, hydroxy, $C_{1-4}$alkoxy, (halo)$_{1-3}$($C_{1-4}$)alkyl, nitro, unsubstituted amino and cyano), —($C_{1-4}$)alkyl($C_{1-4}$)alkoxy, —($C_{1-4}$)alkyl-hydroxy, —($C_{1-4}$)alkyl-(halo)$_{1-3}$, —($C_{1-4}$)alkyl-amino (wherein amino is substituted with two substituents independently selected from the group consisting of hydrogen and $C_{1-4}$alkyl), —($C_{1-4}$)alkyl-amino($C_{1-4}$)alkylamino, —$C_{1-4}$alkyl-NH—C(O)—($C_{1-4}$)alkyl, —$C_{1-4}$alkyl-NH—SO$_2$—($C_{1-4}$)alkyl, —($C_{1-4}$)alkyl-SH, —($C_{1-4}$)alkyl-S—($C_{1-4}$)alkyl, —($C_{1-4}$)alkyl-SO$_2$—($C_{1-4}$)alkyl, —($C_{1-4}$)alkyl-O—C(O)—($C_{1-4}$)alkyl, —($C_{1-4}$)alkyl-C(N), —($C_{1-4}$)alkyl-C(NH)—NH$_2$, —($C_{1-4}$)alkyl-CO$_2$H, —($C_{1-4}$)alkyl-C(O)—O—($C_{1-4}$)alkyl, —($C_{1-4}$)alkyl-C(O)—NH$_2$, —(CH$_2$)$_{2-4}$-heterocyclyl, —(CH$_2$)$_{2-4}$-T-C(V)—Z (wherein T is NH, V is O and Z is amino (wherein amino is substituted with two substituents independently selected from the group consisting of hydrogen and $C_{1-4}$alkyl)).

Preferred embodiments of the present invention include compounds of Formula (I) wherein, X is selected from the group consisting of N and CR$^5$.

Preferred embodiments of the present invention include compounds of Formula (I) wherein, R$^3$ and R$^4$ are independently selected from the group consisting of hydrogen, $C_{1-4}$alkyl, $C_{2-4}$alkenyl, $C_{2-4}$alkynyl, $C_{1-4}$alkoxy, —C(O)H, —C(O)—($C_{1-4}$)alkyl, —CO$_2$H, —C(O)—O—($C_{1-4}$)alkyl, —C(O)—NH$_2$, —C(NH)—NH$_2$, —C(O)—NH—($C_{1-4}$)alkyl, —C(O)—N[($C_{1-4}$)alkyl]$_2$, —SH, —S—($C_{1-4}$)alkyl, —SO$_2$—($C_{1-4}$)alkyl, —SO$_2$—NH$_2$, —SO$_2$—NH—($C_{1-4}$)alkyl, —SO$_2$—N[($C_{1-4}$)alkyl]$_2$, amino (substituted with two substituents independently selected from the group consisting of hydrogen, $C_{1-4}$alkyl, $C_{2-4}$alkenyl, $C_{2-4}$alkynyl, —($C_{1-4}$)alkyl-NH$_2$, —C(O)—($C_{1-4}$)alkyl, —C(O)—O—($C_{1-4}$)alkyl, —C(O)—NH$_2$, —C(O)—NH—($C_{1-4}$)alkyl, —C(O)—N[($C_{1-4}$)alkyl]$_2$, —SO$_2$—($C_{1-4}$)alkyl, —SO$_2$—NH$_2$, —SO$_2$—NH—($C_{1-4}$)alkyl, —SO$_2$—N[($C_{1-4}$)alkyl]$_2$ and —C(NH)—NH$_2$), amino-($C_{1-4}$)alkyl- (wherein amino is substituted with two substituents independently selected from the group consisting of hydrogen, $C_{1-4}$alkyl, $C_{2-4}$alkenyl, $C_{2-4}$alkynyl, —($C_{1-4}$)alkyl-NH$_2$, —C(O)—($C_{1-4}$)alkyl, —C(O)—O—($C_{1-4}$)alkyl, —C(O)—NH$_2$, —C(O)—NH—($C_{1-4}$)alkyl, —C(O)—N[($C_{1-4}$)alkyl]$_2$, —SO$_2$—($C_{1-4}$)alkyl, —SO$_2$—NH$_2$, —SO$_2$—NH—($C_{1-4}$)alkyl, —SO$_2$—N[($C_{1-4}$)alkyl]$_2$ and —C(NH)—NH$_2$), cyano, halo, (halo)$_{1-3}$($C_{1-4}$)alkyl, (halo)$_{1-3}$($C_{1-4}$)alkoxy, hydroxy, hydroxy($C_{1-4}$)alkyl, nitro, aryl, —($C_{1-4}$)alkyl-aryl, heteroaryl and —($C_{1-4}$)alkyl-heteroaryl.

More preferably, R$^3$ and R$^4$ are independently selected from the group consisting of hydrogen, $C_{1-4}$alkyl, $C_{1-4}$alkoxy, cyano and halogen.

Most preferably, R$^3$ and R$^4$ are independently selected from the group consisting of hydrogen, methyl, methoxy, cyano and chloro.

Preferred embodiments of the present invention include compounds of Formula (I) wherein, Y and Z are independently selected from the group consisting of O, S, (H,OH) and (H,H); with the proviso that one of Y and Z is O, and the other is selected from the group consisting of O, S, (H,OH) and (H,H).

More preferably, Y and Z are independently selected from the group consisting of O and (H,H); with the proviso that one of Y and Z is O, and the other is selected from the group consisting of O and (H,H).

Preferred embodiments of the present invention include compounds of Formula (I) wherein, R$^5$ is selected from the group consisting of hydrogen, halogen, $C_{1-4}$alkyl, $C_{2-4}$alkenyl, $C_{2-4}$alkynyl {wherein alkyl, alkenyl and alkynyl are optionally substituted with one to two substituents independently selected from the group consisting of amino (substituted with two substituents selected from the group consisting of hydrogen and $C_{1-4}$alkyl), cyano, halo, hydroxy, nitro, oxo, aryl and heteroaryl}, aryl and heteroaryl {wherein aryl and heteroaryl are optionally substituted with one to two substituents independently selected from the group consisting of $C_{1-4}$alkyl, $C_{1-4}$alkoxy, amino (substituted with two substituents selected from the group consisting of hydrogen and $C_{1-4}$alkyl), cyano, halo, hydroxy and nitro}.

More preferably, R$^5$ is selected from the group consisting of $C_{1-4}$alkyl and aryl.

Most preferably, R$^5$ is selected from the group consisting of methyl and naphthalenyl.

Exemplified compounds of Formula (I) include compounds selected from Formula (Ia) (N1 and N2 for the R$^2$ substituent indicate that R$^2$ is attached to the N1- or N2-position of the indazole ring, respectively):

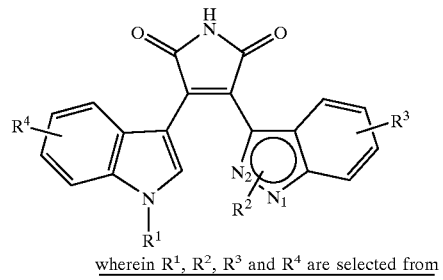

Formula (Ia)

wherein R$^1$, R$^2$, R$^3$ and R$^4$ are selected from

| No. | R$^1$ | R$^2$ | R$^3$ | R$^4$ |
|---|---|---|---|---|
| 1 | H$_2$C=CH | N1-[Me$_2$NCH$_2$CH(OH)CH$_2$] | H | H; |
| 2 | H$_2$C=CH | N1-[MeNHCH$_2$CH(OH)CH$_2$] | H | H; |
| 3 | H$_2$C=CH | N1-[Me$_2$N(CH$_2$)$_3$] | H | H; |
| 4 | H$_2$C=CH | N1-[Me$_2$NCH$_2$CH(OH)CH$_2$] | 5-Cl | H; |
| 5 | H$_2$C=CH | N1-[Me$_2$N(CH$_2$)$_3$] | 5-Cl | H; |

-continued

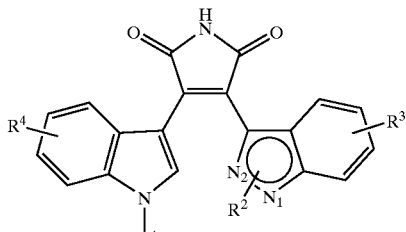

Formula (Ia)

wherein R¹, R², R³ and R⁴ are selected from

| No. | R¹ | R² | R³ | R⁴ |
|---|---|---|---|---|
| 6 | $H_2C=CH$ | N1-[$Me_2N(CH_2)_3$] | H | 5-Cl; |
| 7 | $H_2C=CHCH_2$ | N1-[$Me_2N(CH_2)_3$] | H | H; |
| 8 | 3-thienyl | N1-[$Me_2N(CH_2)_3$] | H | H; |
| 9 | 2-thienyl | N1-[$Me_2N(CH_2)_3$] | H | H; |
| 10 | $H_2C=CH$ | N1-[$Me_2N(CH_2)_3$] | H | 4-Cl; |
| 11 | 3-furyl | N1-[$Me_2N(CH_2)_3$] | H | H; |
| 12 | 3-pyridinyl | N1-[$Me_2N(CH_2)_3$] | H | H; |
| 13 | 3-pyridinyl | N1-[$Me_2N(CH_2)_3$] | H | 5-Cl; |
| 14 | 2-naphthyl | N1-[$Me_2N(CH_2)_3$] | H | H; |
| 15 | 1-naphthyl | N1-[$Me_2N(CH_2)_3$] | H | H; |
| 16 | 4-isoquinolinyl | N1-[$Me_2N(CH_2)_3$] | H | H; |
| 18 | 3-pyridinyl | N1-[$Me_2N(CH_2)_3$] | H | 6-Cl; |
| 19 | 3-quinolinyl | N1-[$Me_2N(CH_2)_3$] | H | H; |
| 21 | 3-quinolinyl | N1-[$Et_2N(CH_2)_3$] | H | H; |
| 22 | 3-quinolinyl | N1-[(4-morpholinyl)($CH_2)_3$] | H | H; |
| 23 | 3-quinolinyl | N1-[$HCO(CH_2)_2$] | H | H; |
| 24 | 3-quinolinyl | N1-[(1,3-dioxolan-2-yl)($CH_2)_2$] | H | H; |
| 25 | 3-pyridinyl | N1-[$Me_2N(CH_2)_3$] | H | 5-OMe; |
| 26 | 3-pyridinyl-$CH_2$ | N1-[$Me_2N(CH_2)_3$] | H | H; |
| 27 | (6-$CH_3$)pyridin-3-yl | N1-[$Me_2N(CH_2)_3$] | H | H; |
| 28 | $H_2C=CH$ | N2-[$Me_2N(CH_2)_3$] | H | H; |
| 29 | $H_2C=CH$ | N2-[$Me_2N(CH_2)_3$] | H | 5-Cl; |
| 31 | 2-pyridinyl | N1-[$Me_2N(CH_2)_3$] | H | H; |
| 32 | 4-pyridinyl | N1-[$Me_2N(CH_2)_3$] | H | H; |
| 33 | 2-thienyl | N1-[$Me_2N(CH_2)_3$] | H | 5-Cl; |
| 34 | 5-pyrimidinyl | N1-[$Me_2N(CH_2)_3$] | H | H; |
| 35 | (5-Br)pyridin-2-yl | N1-[$Me_2N(CH_2)_3$] | H | H; |
| 38 | $Me_2N(CH_2)_3$ | N1-H | H | H; |
| 39 | H | N1-[$Me_2NCH_2CH(OH)CH_2$] | H | H; |
| 40 | Me | N1-[$Me_2NCH_2CH(OH)CH_2$] | 5-Cl | H; |
| 41 | Me | N1-[$Me_2NCH_2CH(OH)CH_2$] | H | H; |
| 42 | Me | N1-[$Me_2N(CH_2)_3$] | H | H; |
| 43 | Me | N1-[$Me_2N(CH_2)_3$] | H | 5-Cl; |
| 44 | Et | N1-[$Me_2N(CH_2)_3$] | H | H; |
| 45 | Ph | N1-[$Me_2N(CH_2)_3$] | H | H; |
| 46 | Et | N1-[$Me_2N(CH_2)_3$] | H | 5-Cl; |
| 47 | H | N1-[$Me_2N(CH_2)_3$] | H | 5-Cl; |
| 48 | Ph | N1-[$Me_2N(CH_2)_3$] | H | 5-Cl; |
| 49 | H | N1-[$Me_2N(CH_2)_3$] | H | 4-Cl; |
| 50 | i-propyl | N1-[$Me_2N(CH_2)_3$] | H | 5-Cl; |
| 51 | Et | N1-[$Me_2N(CH_2)_3$] | H | 5-Me; |
| 52 | $HO(CH_2)_2$ | N1-[$Me_2N(CH_2)_3$] | H | H; |
| 53 | 2-MePh | N1-[$Me_2N(CH_2)_3$] | H | H; |
| 54 | 3-BrPh | N1-[$Me_2N(CH_2)_3$] | H | H; |
| 55 | H | N1-[$Me_2N(CH_2)_3$] | H | H; |
| 56 | Me | N2-[$Me_2N(CH_2)_3$] | H | H; |
| 59 | $Me_2N(CH_2)_3$ | N1-3-pyridinyl | H | H; |
| 60 | 3-benzo[b]thienyl | N1-[$Me_2N(CH_2)_3$] | H | H; |
| 61 | 3-Ph-Ph | N1-[$Me_2N(CH_2)_3$] | H | H; |
| 62 | 2,5-diMe-pyridin-3-yl | N1-[$Me_2N(CH_2)_3$] | H | H; |
| 63 | 6-OMe-naphth-2-yl | N1-[$Me_2N(CH_2)_3$] | H | H; |
| 64 | 6-OH-naphth-2-yl | N1-[$Me_2N(CH_2)_3$] | H | H; |
| 65 | 6-quinolinyl | N1-[$Me_2N(CH_2)_3$] | H | H; |
| 66 | 1-naphthyl-$CH_2$ | N1-[$Me_2N(CH_2)_3$] | H | H; |
| 67 | 2-quinolinyl-$CH_2$ | N1-[$Me_2N(CH_2)_3$] | H | H; |
| 68 | 3-pyridinyl | N1-[(4-morpholinyl)($CH_2)_3$] | H | H; |
| 69 | Et | N1-[(4-morpholinyl)($CH_2)_3$] | H | 5-Cl; |
| 70 | 2-naphthyl | N1-[(4-morpholinyl)($CH_2)_3$] | H | H; |
| 71 | 2,6-diCl-Ph—$CH_2$ | N1-[$Me_2N(CH_2)_3$] | H | H; |
| 72 | 3-(thien-3-yl)-Ph | N1-[$Me_2N(CH_2)_3$] | H | H; |
| 73 | 5-Cl-benzo[b]thien-3-yl-$CH_2$ | N1-[$Me_2N(CH_2)_3$] | H | H; |
| 74 | Me | N1-[$HO(CH_2)_3$] | H | 5-Cl; |

-continued

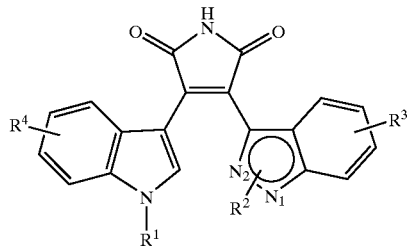

Formula (Ia)

wherein R¹, R², R³ and R⁴ are selected from

| No. | R¹ | R² | R³ | R⁴ |
|---|---|---|---|---|
| 75 | Me | N1-[(1-pyrrolidinyl)(CH$_2$)$_3$] | H | 5-Cl; |
| 76 | Me | N1-[AcO(CH$_2$)$_3$] | H | 5-Cl; |
| 77 | Me | N1-[(4-Me-piperazin-1-yl)(CH$_2$)$_3$] | H | 5-Cl; |
| 78 | Me | N1-[(4-morpholinyl)(CH$_2$)$_3$] | H | 5-Cl; |
| 79 | Me | N1-[(HOCH$_2$CH$_2$)MeN(CH$_2$)$_3$] | H | 5-Cl; |
| 80 | Me | N1-[MeHN(CH$_2$)$_3$] | H | 5-Cl; |
| 81 | Et | N1-[Me$_2$N(CH$_2$)$_3$] | H | 5-OMe; |
| 82 | Me | N1-[(PhCH$_2$)MeN(CH$_2$)$_3$] | H | 5-Cl; |
| 83 | MeHN(CH$_2$)$_2$O(CH$_2$)$_2$ | N1-[MeHN(CH$_2$)$_2$O(CH$_2$)$_2$] | H | H |
| 84 | 2-naphthyl | N1-[HO(CH$_2$)$_3$] | H | H; |
| 85 | 2-naphthyl | N1-[(1-pyrrolidinyl)(CH$_2$)$_3$] | H | H; |
| 86 | (4-morpholinyl)(CH$_2$)$_3$ | N1-Et | 5-Cl | H |
| 87 | (4-Me-piperazin-1-yl)-(CH$_2$)$_3$ | N1-Et | 5-Cl | H |
| 88 | 2-naphthyl | N1-[(HOCH$_2$CH$_2$)MeN(CH$_2$)$_3$] | H | H; |
| 89 | 2-naphthyl | N1-[4-Me-piperazin-1-yl-(CH$_2$)$_3$] | H | H; |
| 90 | Et | N1-[Me$_2$N(CH$_2$)$_3$] | H | 6-Cl; |
| 91 | 2-naphthyl | N1-[HO(CH$_2$)$_4$] | H | H; |
| 92 | 3-benzo[b]thienyl | N1-[HO(CH$_2$)$_4$] | H | H; |
| 93 | 3-benzo[b]thienyl | N1-[Me$_2$N(CH$_2$)$_4$] | H | H; |
| 94 | 3-pyridinyl | N1-[HO(CH$_2$)$_3$] | H | H; |
| 95 | Et | N1-[Me$_2$N(CH$_2$)$_3$] | H | 7-Cl; |
| 96 | (1-pyrrolidinyl)(CH$_2$)$_3$ | N1-Et | 5-Cl | H |
| 97 | 2-naphthyl | N1-[Me$_2$N(CH$_2$)$_4$] | H | H; |
| 98 | Et | N1-[Me$_2$N(CH$_2$)$_3$] | H | 5-CN; |
| 99 | 3-benzo[b]thienyl | N1-[HO(CH$_2$)$_2$] | H | H; |
| 100 | 2-naphthyl | N1-[HO(CH$_2$)$_2$] | H | H; |
| 101 | 2-naphthyl | N1-[Me$_2$N(CH$_2$)$_2$] | H | H; |
| 102 | 2-pyridinyl | N1-[HO(CH$_2$)$_3$] | H | H; |
| 103 | 3-benzo[b]thienyl | N1-[Me$_2$N(CH$_2$)$_2$] | H | H; |
| 104 | 3-benzo[b]thienyl | H | H | H; |
| 105 | 4-isoquinolinyl | N1-[HO(CH$_2$)$_3$] | H | H; |
| 106 | 3-pyridinyl | N1-[HO(CH$_2$)$_2$O(CH$_2$)$_2$] | H | H; |
| 107 | 3-quinolinyl | N1-[HO(CH$_2$)$_3$] | H | H; |
| 108 | 3-benzo[b]thienyl | N1-[H$_2$N(CH$_2$)$_3$] | H | H; |
| 109 | 3-pyridinyl | N1-[H$_2$N(CH$_2$)$_3$] | H | H; |
| 110 | 3-pyridinyl | N1-[HO(CH$_2$)$_2$] | H | H; |
| 111 | 3-pyridinyl | N1-[HO(CH$_2$)$_4$] | H | H; |
| 112 | 3-pyridinyl | N1-[OHC(CH$_2$)$_2$] | H | H; |
| 113 | 3-pyridinyl | N1-[HO$_2$C(CH$_2$)$_2$] | H | H; |
| 114 | 3-pyridinyl | N1-[(HOCH$_2$CH$_2$)MeN(CH$_2$)$_3$] | H | H; |
| 115 | 3-pyridinyl | N1-[BocNH(CH$_2$)$_3$] | H | H; |
| 116 | 3-benzo[b]thienyl | N1-[MeO$_2$C(CH$_2$)$_2$] | H | H; |
| 117 | 3-pyridinyl | N1-[MeO(CH$_2$)$_3$] | H | H; |
| 118 | 3-pyridinyl | H | H | H; |
| 119 | 3-pyridinyl | N1-[AcO(CH$_2$)$_3$] | H | H; |
| 120 | 4-morpholinyl)(CH$_2$)$_3$ | N2-Et | 5-Cl | H; |
| 121 | 3-pyridinyl | N2-[HO(CH$_2$)$_3$] | H | H; |
| 122 | 2-naphthyl | N2-[Me$_2$N(CH$_2$)$_2$] | H | H; |
| 123 | 3-benzo[b]thienyl | N2-[Me$_2$N(CH$_2$)$_2$] | H | H; |
| or, | | | | |
| 124 | Me | N2-[HO(CH$_2$)$_3$] | H | 5-Cl; | and pharmaceutically acceptable salts thereof.

Exemplified compounds of Formula (I) include compounds selected from Formula (Ib) (N1 and N2 for the $R^2$ substituent indicate that $R^2$ is attached to the N1- or N2-position of the indazole ring, respectively):

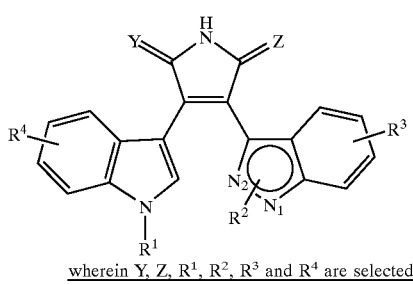

Formula (Ib)

wherein Y, Z, $R^1$, $R^2$, $R^3$ and $R^4$ are selected from

| No. | Y | Z | $R^1$ | $R^2$ | $R^3$ | $R^4$ |
|---|---|---|---|---|---|---|
| 36 | H, H | O | 2-thienyl | N1-[Me$_2$N(CH$_2$)$_3$] | H | H; |
| 37 or, | O | H, H | 2-thienyl | N1-[Me$_2$N(CH$_2$)$_3$] | H | H; |
| 125 | O | H, H | 3-pyridinyl | N1-[Me$_2$N(CH$_2$)$_3$] | H | H; | and pharmaceutically acceptable salts thereof.

Exemplified compounds of Formula (I) include compounds selected from Formula (Ic) (N1 and N2 for the $R^2$ substituent indicate that $R^2$ is attached to the N1- or N2-position of the indazole ring, respectively):

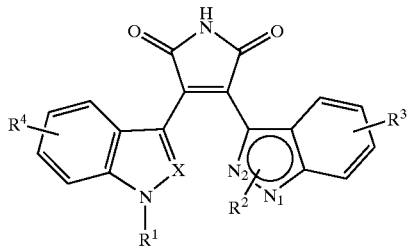

Formula (Ic)

wherein X, $R^1$, $R^2$, $R^3$, $R^4$ and $R^5$ are selected from

| No. | X | $R^1$ | $R^2$ | $R^3$ | $R^4$ | $R^5$ |
|---|---|---|---|---|---|---|
| 17 | C-$R^5$ | 3-pyridinyl | N1-[Me$_2$N(CH$_2$)$_3$] | H | H | 2-naphthyl; |
| 20 | C-$R^5$ | 3-pyridinyl | N1-[Me$_2$N(CH$_2$)$_3$] | H | 5-Cl | CH$_3$; |
| 30 | N | H$_2$C=CHCH$_2$ | N1-[Me$_2$N(CH$_2$)$_3$] | H | H | —; |
| 57 or, | N | H | N1-[Me$_2$N(CH$_2$)$_3$] | H | H | —; |
| 58 | N | Me$_2$N(CH$_2$)$_3$ | N1-[Me$_2$N(CH$_2$)$_3$] | H | H | —; | and pharmaceutically acceptable salts thereof.

The compounds of the present invention may also be present in the form of pharmaceutically acceptable salts. For use in medicine, the salts of the compounds of this invention refer to non-toxic "pharmaceutically acceptable salts." FDA approved pharmaceutically acceptable salt forms (Ref. International J. Pharm. 1986, 33, 201–217; J. Pharm. Sci., 1977, Jan, 66(1), p1) include pharmaceutically acceptable acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methyisulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc. Other salts may, however, be useful in the preparation of compounds according to this invention or of their pharmaceutically acceptable salts. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid.

The present invention includes within its scope prodrugs of the compounds of this invention. In general, such prodrugs will be functional derivatives of the compounds which are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. Where the processes for the preparation of the compounds according to the invention give rise to mixture of stereoisomers, these isomers may be separated by conventional techniques such as preparative chromatography. The compounds may be prepared in racemic form or individual enantiomers may be prepared by standard techniques known to those skilled in the art, for example, by enantiospecific synthesis or resolution formation of diastereomeric pairs by salt formation with an optically active acid, followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column. It is to be understood that all such isomers and mixtures thereof are encompassed within the scope of the present invention.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991. The protecting groups may be removed at a convenient subsequent stage using methods known in the art.

Furthermore, some of the crystalline forms for the compounds may exist as polymorphs and as such are intended to be included in the present invention. In addition, some of the compounds may form solvates with water (i.e., hydrates) or common organic solvents and such solvates are also intended to be encompassed within the scope of this invention.

Unless specified otherwise, the term "alkyl" refers to a saturated straight or branched chain consisting solely of 1–8 hydrogen substituted carbon atoms; preferably, 1–6 hydrogen substituted carbon atoms; and, most preferably, 1–4 hydrogen substituted carbon atoms. The term "alkenyl" refers to a partially unsaturated straight or branched chain consisting solely of 2–8 hydrogen substituted carbon atoms that contains at least one double bond. The term "alkynyl" refers to a partially unsaturated straight or branched chain consisting solely of 2–8 hydrogen substituted carbon atoms that contains at least one triple bond. The term "alkoxy" refers to —O-alkyl, where alkyl is as defined supra. The term "hydroxyalkyl" refers to radicals wherein the alkyl chain terminates with a hydroxy radical of the formula HO-alkyl, where alkyl is as defined supra. Alkyl, alkenyl and alkynyl chains are optionally substituted within the alkyl chain or or a terminal carbon atom.

The term "cycloalkyl" refers to a saturated or partially unsaturated monocyclic alkyl ring consisting of 3–8 hydrogen substituted carbon atoms or a saturated or partially unsaturated bicyclic ring consisting of 9 or 10 hydrogen substituted carbon atoms. Examples include, and are not limited to, cyclopropyl, cyclopentyl, cyclohexyl or cycloheptyl.

The term "heterocyclyl" refers to a saturated or partially unsaturated ring having five members of which at least one member is a N, O or S atom and which optionally contains one additional O atom or one, two or three additional N atoms, a saturated or partially unsaturated ring having six members of which one, two or three members are a N atom, a saturated or partially unsaturated bicyclic ring having nine members of which at least one member is a N, O or S atom and which optionally contains one, two or three additional N atoms or a saturated or partially unsaturated bicyclic ring having ten members of which one, two or three members are a N atom. Examples include, and are not limited to, pyrrolinyl, pyrrolidinyl, 1,3-dioxolanyl, imidazolinyl, imidazolidinyl, pyrazolinyl, pyrazolidinyl, piperidinyl, morpholinyl or piperazinyl.

The term "aryl" refers to an aromatic monocyclic ring containing 6 hydrogen substituted carbon atoms, an aromatic bicyclic ring system containing 10 hydrogen substituted carbon atoms or an aromatic tricyclic ring system containing 14 hydrogen substituted carbon atoms. Examples include, and are not limited to, phenyl, naphthalenyl or anthracenyl.

The term "heteroaryl" refers to an aromatic monocyclic ring system containing five members of which at least one member is a N, O or S atom and which optionally contains one, two or three additional N atoms, an aromatic monocyclic ring having six members of which one, two or three members are a N atom, an aromatic bicyclic ring having nine members of which at least one member is a N, O or S atom and which optionally contains one, two or three additional N atoms or an aromatic bicyclic ring having ten members of which one, two or three members are a N atom. Examples include, and are not limited to, furyl, thienyl, pyrrolyl, oxazolyl, thiazolyl, imidazolyl, pyrazolyl, isoxazolyl, isothiazolyl, pyridinyl, pyridazinyl, pyrimidinyl, pyrazinyl, indolyl, indazolyl, benzo[b]thienyl, quinolinyl, isoquinolinyl or quinazolinyl.

Whenever the term "alkyl" or "aryl" or either of their prefix roots appear in a name of a substituent (e.g., aralkyl, alkylamino) it shall be interpreted as including those limitations given above for "alkyl" and "aryl." Designated numbers of carbon atoms (e.g., $C_1$–$C_6$) shall refer independently to the number of carbon atoms in an alkyl or cycloalkyl moiety or to the alkyl portion of a larger substituent in which alkyl appears as its prefix root.

Under standard nomenclature rules used throughout this disclosure, the terminal portion of the designated side chain is described first followed by the adjacent functionality toward the point of attachment. Thus, for example, a "phenyl$C_{1-6}$alkylamido$C_{1-6}$alkyl" substituent refers to a group of the formula:

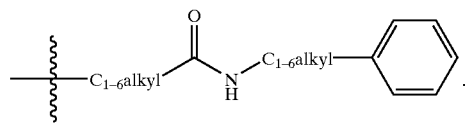

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

An embodiment of the invention is a pharmaceutical composition comprising a pharmaceutically acceptable carrier and any of the compounds described above. Illustrative of the invention is a pharmaceutical composition made by mixing any of the compounds described above and a pharmaceutically acceptable carrier. Another illustration of the invention is a process for making a pharmaceutical composition comprising mixing any of the compounds described above and a pharmaceutically acceptable carrier. Further illustrative of the present invention are pharmaceutical compositions comprising one or more compounds of this invention in association with a pharmaceutically acceptable carrier.

As used herein, the term "composition" is intended to encompass a product comprising the specified ingredients in the specified amounts, as well as any product which results, directly or indirectly, from combinations of the specified ingredients in the specified amounts.

The compounds of the present invention are selective kinase or dual-kinase inhibitors useful in a method for treating or ameliorating a kinase or dual-kinase mediated disorder. In particular, the kinase is selected from protein kinase C or glycogen synthase kinase-3. More particularly, the kinase is selected from protein kinase Cα, protein kinase Cβ-II, protein kinase Cγ or glycogen synthase kinase-3β.

Protein Kinase C Isoforms

Protein kinase C is known to play a key role in intracellular signal transduction (cell-cell signaling), gene expression and in the control of cell differentiation and growth. The PKC family is composed cT twelve isoforms that are further classified into 3 subfamilies: the calcium dependent classical PKC isoforms alpha (α), beta-I (β-I), beta-II (β-II) and gamma (γ); the calcium independent PKC isoforms deita (δ), epsilon (ε), eta (η), theta (θ) and mu (μ); and, the atypical PKC isoforms zeta (ζ), lambda (λ) and iota (ι).

Certain disease states tend to be associated with elevation of particular PKC isoforms. The PKC isoforms exhibit distinct tissue distribution, subcellular localization and activation-dependent cofactors. For example, the α and β isoforms of PKC are selectively induced in vascular cells stimulated with agonists such as vascular endothelial growth factor (VEGF) (P. Xia, et al., *J. Clin. Invest.*, 1996, 98, 2018) and have been implicated in cellular growth, differentiation, and vascular permeability (H. Ishii, et al., *J. Mol. Med.*, 1998, 76, 21). The elevated blood glucose levels found in diabetes leads to an isoform-specific elevation of the β-II isoform in vascular tissues (Inoguchi, et al., *Proc. Natl. Acad. Sci. USA*, 1992, 89, 11059–11065). A diabetes-linked elevation of the β isoform in human platelets has been correlated with their altered response to agonists (Bastyr III, E. J. and Lu, J., *Diabetes*, 1993, 42, (Suppl. 1) 97A). The human vitamin D receptor has been shown to be selectively phosphorylated by PKCβ. This phosphorylation has been inked to alterations in the functioning of the receptor (Hsieh, et al., *Proc. Natl. Acad. Sci. USA*, 1991, 88, 9315–9319; Hsieh, et al., *J. Biol. Chem.*, 1993, 268, 15118–15126). In addition, the work has shown that the β-II isoform is responsible for erythroleukemia cell proliferation while the α isoform is involved in megakaryocyte differentiation in these same cells (Murray, et al., *J. Biol. Chem.*, 1993, 268, 15847–15853).

Cardiovascular Diseases

PKC activity plays an important role in cardiovascular diseases. Increased PKC activity in the vasculature has been shown to cause increased vasoconstriction and hypertension (Bilder, G. E., et al., *J. Pharmacol. Exp. Ther.*, 1990, 252, 526–530). PKC inhibitors block agonist-induced smooth muscle cell proliferation (Matsumoto, H. and Sasaki, Y., *Biochem. Biophys. Res. Commun.*, 1989, 158, 105–109). PKC β triggers events leading to induction of Egr-1 (Early Growth Factor-1) and tissue factor under hypoxic conditions (as part of the oxygen deprivation-mediated pathway for triggering procoagulant events) (Yan, S-F, et al., *J. Biol. Chem.*, 2000, 275, 16, 11921–11928). PKC β is suggested as a mediator for production of PAI-1 (Plaminogen Activator Inhibitor-1) and is implicated in the development of thrombosis and atherosclerosis (Ren, S, et al., *Am. J. Physiol.*, 2000, 278, (4, Pt. 1), E656-E662). PKC inhibitors are useful in treating cardiovascular ischemia and improving cardiac function following ischemia (Muid, R. E., et al., *FEBS Lett.*, 1990, 293, 169–172; Sonoki, H. et al., *Kokyu-To Junkan*, 1989, 37, 669–674). Elevated PKC levels have been correlated with an increased platelet function response to agonists (Bastyr III, E. J. and Lu, J., *Diabetes*, 1993, 42, (Suppl. 1) 97A). PKC has been implicated in the biochemical pathway in the platelet-activating factor (PAF) modulation of microvascular permeability (Kobayashi, et al., *Amer. Phys. Soc.*, 1994, H1214–H1220). PKC inhibitors affect agonist-induced aggregation in platelets (Toullec, D., et al., *J. Biol. Chem.*, 1991, 266, 15771–15781). Accordingly, PKC inhibitors may be indicated for use in treating cardiovascular disease, ischemia, thrombotic conditions, atherosclerosis and restenosis.

Diabetes

Excessive activity of PKC has been linked to insulin signaling defects and therefore to the insulin resistance seen in Type II diabetes (Karasik, A., et al., *J. Biol. Chem.*, 1990, 265, 10226–10231; Chen, K. S., et al., *Trans. Assoc. Am. Physicians*, 1991, 104, 206–212; Chin, J. E., et al., *J. Biol. Chem.*, 1993, 268, 6338–6347).

Diabetes-Associated Disorders

Studies have demonstrated an increase in PKC activity in tissues known to be susceptible to diabetic complications when exposed to hyperglycemic conditions (Lee, T-S., et al., *J. Clin. Invest.*, 1989, 83, 90–94; Lee, T-S., et al., *Proc. Natl. Acad. Sci. USA*, 1989, 86, 5141–5145; Craven, P. A. and DeRubertis, F. R., *J. Clin. Invest.*, 1989, 87, 1667–1675; Wolf, B. A., et al., *J. Clin. Invest.*, 1991, 87, 31–38; Tesfamariam, B. et al., *J. Clin. Invest*, 1991, 87, 1643–1648). For example, activation of the PKC-β-II isoform plays an important role in diabetic vascular complications such as retinopathy (Ishii, H., et al., *Science*, 1996, 272, 728–731) and PKCβ has been implicated in development of the cardiac hypertrophy associated with heart failure (X. Gus et al., *Circ. Res.*, 1994, 75. 926; R. H. Strasser. et al., *Circulation*, 1996, 94–1551). Overexpression of cardiac PKCβII in transgenic mice caused cardiomyopathy involving hypertrophy, fibrosis and decreased left ventricular function (H. Wakasaki, et al., *Proc. Natl. Acad. Sci. USA*, 1997, 94, 9320).

Inflammatory Diseases

PKC inhibitors block inflammatory responses such as the neutrophil oxidative burst, CD3 down-regulation in T-lymphocytes and phorbol-induced paw edema (Twoemy, B., et al., *Biochem. Biophys. Res. Commun.*, 1990, 171, 1087–1092; Mulqueen, M. J., et al. *Agents Actions*, 1992, 37, 85–89). PKCβ has an essential role in the degranulation of bone marrow-derived mast cells, thus affecting cell capacity to produce IL-6 (Interleukin-6) (Nechushtan, H., et al., *Blood*, 2000 (March), 95, 5, 1752–1757). PKC plays a role in enhanced ASM (Airway Smooth Muscle) cell growth in rat models of two potential risks for asthma: hyperresponsiveness to contractile agonists and to growth stimuli (Ren, S, et al., *Am. J. Physiol.*, 2000, 278, (4, Pt. 1), E656–E662). PKC β-1 overexpression augments an increase in endothelial permeability, suggesting an important function in the regulation of the endothelial barrier (Nagpala, P. G., et al., *J. Cell Physiol.*, 1996, 2, 249–55). PKCβ mediates activation of neutrophil NADPH oxidase by PMA and by stimulation of Fcγ receptors in neutrophils (Dekker, L. V., et al., *Biochem. J.*, 2000, 347, 285–289). Thus, PKC inhibitors may be indicated for use in treating inflammation and asthma.

Immunological Disorders

PKC may be useful in treating or ameliorating certain immunological disorders. While one study suggests that HCMV (Human Cytomegalovirus) inhibition is not correlated with PKC inhibition (Slater, M. J., et al., *Biorg. & Med. Chem.*, 1999, 7, 1067–1074), another study showed that the PKC signal transduction pathway synergistically interacted with the cAMP-dependent PKA pathway to activate or increase HIV-1 transcription and viral replication and, was abrogated with a PKC inhibitor (Rabbi, M. F., et al., *Virology*, 1998 (June 5), 245, 2, 257–69). Therefore, an immunological disorder may be treated or ameliorated as a function of the affected underlying pathway's response to up- or down-regulation of PKC.

PKC β deficiency also results in an immunodeficiency characterized by impaired humoral immune responses and a reduced B cell response, similar to X-linked immunodeficiency in mice, playing an important role in antigen receptor-mediated signal transduction (Leitges, M., et al., *Science* (Wash., D.C.), 1996, 273, 52076, 788–789). Accordingly, transplant tissue rejection may be ameliorated or prevented by suppressing the immune response using a PKC β inhibitor.

Dermatological Disorders

Abnormal activity of PKC has been linked to dermatological disorders characterized by abnormal proliferation of keratinocytes, such as psoriasis (Horn, F., et al., *J. Invest. Dermatol.*, 1987, 88, 220–222; Raynaud, F. and Evain-Brion, D., *Br. J. Dermatol.*, 1991, 124, 542–546). PKC inhibitors have been shown to inhibit keratinocyte proliferation in a dose-dependent manner (Hegemann, L., et al., *Arch. Dermatol. Res.*, 1991. 283, 456–460; Bollag, W. B., et al., *J. Invest. Dermatol.*, 1993, 100, 240–246).

Oncological Disorders

PKC activity has been associated with cell growth, tumor promotion and cancer (Rotenberg, S. A. and Weinstein, I. B., *Biochem. Mol. Aspects Sel. Cancer*, 1991, 1, 25–73; Ahmad, et al., *Molecular Pharmacology*, 1993, 43, 858–862); PKC inhibitors are known to be effective in preventing tumor growth in animals (Meyer, T., et al., *Int. J. Cancer*, 1989, 43, 851–856; Akinagaka, S., et al., *Cancer Res.*, 1991, 51, 4888–4892). PKC β-1 and β-2 expression in differentiated HD3 colon carcinoma cells blocked their differentiation, enabling them to proliferate in response to basic FGF (Fibroblast Growth Factor) like undifferentiated cells, increasing their growth rate and activating several MBP (Myelin-Basic Protein) kinases, including p57 MAP (Mitogen-Activated Protein) kinase (Sauma, S., et al., *Cell Growth Differ.*, 1996, 7, 5, 587–94). PKC α inhibitors, having an additive therapeutic effect in combination with other anti-cancer agents, inhibited the growth of lymphocytic leukemia cells (Konig, A., et al., *Blood*, 1997, 90, 10, Suppl. 1 Pt. 2). PKC inhibitors enhanced MMC (Mitomycin-C) induced apoptosis in a time-dependent fashion in a gastric cancer cell-line, potentially indicating use as agents for chemotherapy-induced apoptosis (Danso, D., et al., *Proc. Am. Assoc. Cancer Res.*, 1997, 38, 88 Meet., 92). Therefore, PKC inhibitors may be indicated for use in ameliorating cell and tumor growth, in treating or ameliorating cancers (such as leukemia or color cancer) and as adjuncts to chemotherapy.

PKC α (by enhancing cell migration) may mediate some proangiogenic effects of PKC activation while PKC δ may direct antiangiogenic effects of overall PKC activation (by inhibiting cell growth and proliferation) in capillary endothelial cells, thus regulating endothelial proliferation and angiogenesis (Harrington, E. O., et al., *J. Biol. Chem.*, 1997, 272, 11, 7390–7397). PKC inhibitors inhibit cell growth and induce apoptosis in human glioblastoma cell lines, inhibit the growth of human astrocytoma xenografts and act as radiation sensitizers in glioblastoma cell lines (Begemann, M., et al., *Anticancer Res.* (*Greece*), 1998 (Jul–Aug), 18, 4A, 2275–82). PKC inhibitors, in combination with other anti-cancer agents, are radiation and chemosensitizers useful in cancer therapy (Teicher, B. A., et al., *Proc. Am. Assoc. Cancer Res.*, 1998, 39, 89 Meet., 384). PKC β inhibitors (by blocking the MAP kinase signal transduction pathways for VEGF (Vascular Endothelial Growth Factor) and bFGF (basic Fibrinogen Growth Factor) in endothelial cells), in a combination regimen with other anti-cancer agents, have an anti-angiogenic and antitumor effect in a human T98G glioblastoma multiforme xenograft model (Teicher, B. A., et al., *Clinical Cancer Research*, 2001 (March), 7, 634–640). Accordingly, PKC inhibitors may be indicated for use in ameliorating angiogenesis and in treating or ameliorating cancers (such as breast, brain, kidney, bladder, ovarian or colon cancers) and as adjuncts to chemotherapy and radiation therapy.

Central Nervous System Disorders

PKC activity plays a central role in the functioning of the central nervous system (CNS) (Huang, K. P., *Trends Neurosci.*, 1989, 12, 425–432) and PKC is implicated in Alzheimer's disease (Shimohama, S., et al., *Neurology*, 1993, 43, 1407–1413) and inhibitors have been shown to prevent the damage seen in focal and central ischemic brain injury and brain edema (Hara, H., et al., *J. Cereb. Blood Flow Metab.*, 1990, 10, 646–653; Shibata, S., et al., *Brain Res.*, 1992, 594, 290–294). Accordingly, PKC inhibitors may be indicated for use in treating Alzheimer's disease and in treating neurotraumatic and ischemia-related diseases.

The long-term increase in PKC γ (as a component of the phosphoinositide $2^{nd}$ messenger system) and muscarinic acetylcholine receptor expression in an amygdala-kindled rat model has been associated with epilepsy, serving as a basis for the rat's permanent state of hyperexcitability (Beldhuis, H. J. A., et al., *Neuroscience*, 1993, 55, 4, 965–73). Therefore, PKC inhibitors may be indicated for use in treating epilepsy.

The subcellular changes in content of the PKC γ and PKC β-II isoenzymes for animals in an in-vivo thermal hyperalgesia model suggests that peripheral nerve injury contributes to the development of persistent pain (Miletic, V., et al., *Neurosci. Lett.*, 2000, 288, 3, 199–202). Mice lacking PKC γ display normal responses to acute pain stimuli, but almost completely fail to develop a neuropathic pain syndrome after partial sciatic nerve section (Chen, C., et al., *Science* (Wash., D.C.), 1997, 278, 5336, 279–283). PKC modulation may thus be indicated for use in treating chronic pain and neuropathic pain.

PKC has demonstrated a role in the pathology of conditions such as, but not limited to, cardiovascular diseases, diabetes, diabetes-associated disorders, inflammatory diseases, immunological disorders, dermatological disorders, oncological disorders and central nervous system disorders.

Glycogen Synthase Kinase-3

Glycogen synthase kinase-3 (GSK-3) is a serine/threonine protein kinase composed of two isoforms (α and β) which are encoded by distinct genes. GSK-3 is one of several protein kinases which phosphorylate glycogen synthase (GS) (Embi, et al., *Eur. J. Biochem*, 1980, 107, 519–527). The α and β isoforms have a monomeric structure of 49 and 47 kD respectively and are both found in mammalian cells. Both isoforms phosphorylate muscle glycogen synthase (Cross, et al., *Biochemical Journal*, 1994, 303, 21–26) and these two isoforms show good homology between species (human and rabbit GSK-3α are 96% identical).

Diabetes

Type II diabetes (or Non-Insulin Dependent Diabetes Mellitus, NIDDM) is a multifactorial disease. Hyperglycemia is due to insulin resistance in the liver, muscle and other tissues coupled with inadequate or defective secretion of insulin from pancreatic islets. Skeletal muscle is the major site for insulin-stimulated glucose uptake and in this tissue glucose removed from the circulation is either metabolised through glycolysis and the TCA (tricarboxylic acid) cycle or stored as glycogen. Muscle glycogen deposition plays the more important role in glucose homeostasis and Type II diabetic subjects have defective muscle glycogen storage. The stimulation of glycogen synthesis by insulin in skeletal muscle results from the dephosphorylation and activation of glycogen synthase (Villar-Palasi C. and Larner J., *Biochim. Biophys. Acta,* 1960, 39, 171–173, Parker P. J., et al., *Eur. J. Biochem.*, 1983, 130, 227–234, and Cohen P., *Biochem. Soc. Trans.*, 1993, 21, 555–567). The phosphorylation and dephosphorylation of GS are mediated by specific kinases and phosphatases. GSK-3 is responsible for phosphorylation and deactivation of GS, while glycogen bound protein phosphatase 1 (PP1G) dephosphorylates and activates GS. Insulin both inactivates GSK-3 and activates PP1G (Srivastava A. K. and Pandey S. K., *Mol. and Cellular Biochem.*, 1998, 182, 135–141).

Studies suggest that an in(crease in GSK-3 activity might be important in Type II diabetic muscle (Chen, et al., *Diabetes*, 1994, 43, 1234–1241). Overexpression of GSK-3β and constitutively active GSK-3β (S9A, S9e) mutants in HEK-293 cells resulted in suppression of glycogen synthase activity (Eldar-Finkelman, et al., *PNAS*, 1996, 93, 10228–10233) and overexpression of GSK-3β in CHO cells, expressing both insulin receptor and insulin receptor substrate 1 (IRS-1) resulted in impairment of insulin action (Eldar-Finkelman and Krebs, *PNAS*, 1997, 94, 9660–9664). Recent evidence for the involvement of elevated GSK-3 activity and the development of insulin resistance and Type II diabetes in adipose tissue has emerged from studies undertaken in diabetes and obesity prone C57BL/6J mice (Eldar-Finkelman, et al., *Diabetes*, 1999, 48, 1662–1666).

Dermatological Disorders

The finding that transient β-catenin stabilization may play a role in hair development (Gat, et al., *Cell*, 1998, 95, 605–614) suggests that GSK-3 inhibitors could also be used in the treatment of baldness.

Inflammatory Diseases

Studies on fibroblasts from the GSK-3β knockout mouse indicate that inhibition of GSK-3 may be useful in treating inflammatory disorders or diseases through the negative regulation of NFkB activity (Hoeflich K. P., et al., *Nature*, 2000, 406, 86–90).

Central Nervous System Disorders

In addition to modulation of glycogen synthase activity, GSK-3 also plays an important role in the CNS disorders. GSK-3 inhibitors may be of value as neuroprotectants in the treatment of acute stroke and other neurotraumatic injuries (Pap and Cooper, *J. Biol. Chem.*, 1998, 273, 19929–19932). Lithium, a low mM inhibitor of GSK-3, has been shown to protect cerebellar granule neurons from death D'Mello, et al., *Exp. Cell Res.*, 1994, 211, 332–338) and chronic lithium treatment has demonstrable efficacy in the middle cerebral artery occlusion model of stroke in rodents (Nonaka and Chuang, *Neuroreport,* 1998, 9(9), 2081–2084).

Tau and β-catenin, two known in vivo substrates of GSK-3, are of direct relevance in consideration of further aspects of the value of GSK-3 inhibitors in relation to treatment of chronic neurodegenerative conditions. Tau hyperphosphorylation is an early event in neurodegenerative conditions such as Alzheimer's disease and is postulated to promote microtubule disassembly. Lithium has been reported to reduce the phosphorylation of tau, enhance the binding of tau to microtubules and promote microtubule assembly through direct and reversible inhibition of GSK-3 (Hong M. et al *J. Biol. Chem.*, 1997, 272(40), 25326–32). β-catenin is phosphorylated by GSK-3 as part of a tripartite axin protein complex resulting in β-catenin degradation (Ikeda, et al., *EMBO J.*, 1998, 17, 1371–1384). Inhibition of GSK-3 activity is involved in the stabilization of catenin hence promotes β-catenin-LEF-1/TCF transcriptional activity (Eastman, Grosschedl, *Curr. Opin. Cell Biol.*, 1999, 11, 233). Studies have also suggested that GSK-3 inhibitors may also be of value in treatment of schizophrenia (Cotter D., et al. *Neuroreport*, 1998, 9, 1379–1383; Lijam N., et al., *Cell*, 1997, 90, 895–905) and manic depression (Manji, et al., *J. Clin. Psychiatry*, 1999, 60, (Suppl 2) 27–39 for review).

Accordingly, compounds found useful as GSK-3 inhibitors could have further therapeutic utility in the treatment of diabetes, dermatological disorders, inflammatory diseases and central nervous system disorders.

Embodiments of the method of the present invention include a method for treating or ameliorating a kinase or dual-kinase mediated disorder in a subject in need thereof comprising administering to the subject a therapeutically effective amount of an instant compound or pharmaceutical composition thereof. The therapeutically effective amount of the compounds of Formula (I) exemplified in such a method is from about 0.001 mg/kg/day to about 300 mg/kg/day.

Embodiments of the present invention include the use of a compound of Formula (I) for the preparation of a medicament for treating or ameliorating a kinase or dual-kinase mediated disorder in a subject in need thereof.

In accordance with the methods of the present invention, an individual compound of the present invention or a pharmaceutical composition thereof can be administered separately at different times during the course of therapy or concurrently in divided or single combination forms. The instant invention is therefore to be understood as embracing all such regimes of simultaneous or alternating treatment and the term "administering" is to be interpreted accordingly.

Embodiments of the present method include a compound or pharmaceutical composition thereof advantageously co-administered in combination with other agents for treating or ameliorating a kinase or dual-kinase mediated disorder. For example, in the treatment of diabetes, especially Type II diabetes, a compound of Formula (I) or pharmaceutical composition thereof may be used in combination with other agents, especially insulin or antidiabetic agents including, but not limited to, insulin secretagogues (such as sulphonylureas), insulin sensitizers including, but not limited to, glitazone insulin sensitizers (such as thiazolidinediones) or biguanides or a glucosidase inhibitors.

The combination product comprises co-administration of a compound of Formula (I) or pharmaceutical composition thereof and an additional agent for treating or ameliorating a kinase or dual-kinase mediated disorder, the sequential administration of a compound of Formula (I) or pharmaceutical composition thereof and an additional agent for treating or ameliorating a kinase or dual-kinase mediated disorder, administration of a pharmaceutical composition containing a compound of Formula (I) or pharmaceutical composition thereof and an additional agent for treating or ameliorating a kinase or dual-kinase mediated disorder or the essentially simultaneous administration of a separate pharmaceutical composition containing a compound of Formula (I) or pharmaceutical composition thereof and a separate pharmaceutical composition containing an additional agent for treating or ameliorating a kinase or dual-kinase mediated disorder.

The term "subject" as used herein, refers to an animal, preferably a mammal, most preferably a human who has been the object or treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The ubiquitous nature of the PKC and GSK isoforms and their important roles in physiology provide incentive to produce highly selective PKC and GSK inhibitors. Given the evidence demonstrating linkage of certain isoforms to disease states, it is reasonable to assume that inhibitory compounds that are selective to one or two PKC isoforms or to a GSK isoform relative to the other PKC and GSK isoforms and other protein kinases are superior therapeutic agents. Such compounds should demonstrate greater efficacy and lower toxicity by virtue of their specificity. Accordingly, it will be appreciated by one skilled in the art that a compound of Formula (I) is therapeutically effective for certain kinase or dual-kinase mediated disorders based on the modulation of the disorder by selective kinase or dual-kinase inhibition. The usefulness of a compound of formula (I) as a selective kinase or dual-kinase inhibitor can be determined according to the methods disclosed herein and the scope of such use includes use in one or more kinase or dual-kinase mediated disorders.

Therefore, the term "kinase or dual-kinase mediated disorders" as used herein, includes, and is not limited to, cardiovascular diseases, diabetes, diabetes-associated disorders, inflammatory diseases, immunological disorders, dermatological disorders, oncological disorders and CNS disorders.

Cardiovascular diseases include, and are not limited to, acute stroke, heart failure, cardiovascular ischemia, thrombosis, atherosclerosis, hypertension, restenosis, retinopathy of prematurity or age-related macular degeneration. Diabetes includes insulin dependent diabetes or Type II non-insulin dependent diabetes mellitus. Diabetes-associated disorders include, and are not limited to, impaired glucose tolerance, diabetic retinopathy, proliferative retinopathy, retinal vein occlusion, macular edema, cardiomyopathy, nephropathy or neuropathy. Inflammatory diseases include, and are not limited to, vascular permeability, inflammation, asthma, rheumatoid arthritis or osteoarthritis. Immunological disorders include, and are not limited to, transplant tissue rejection, HIV-1 or immunological disorders treated or ameliorated by PKC modulation. Dermatological disorders include, and are not limited to, psoriasis, hair loss or baldness. Oncological disorders include, and are not limited to, cancers or tumor growth (such as breast, brain, kidney, bladder, ovarian or colon cancer or leukemia), proliferative angiopathy and angiogenesis; and, includes use for compounds of Formula (I) as an adjunct to chemotherapy and radiation therapy. CNS disorders include, and are not limited to, chronic pain, neuropathic pain, epilepsy, chronic neurodegenerative conditions (such as dementia or Alzheimer's disease), mood disorders (such as schizophrenia), manic depression or neurotraumatic, cognitive decline and ischemia-related diseases {as a result of head trauma (from acute ischemic stroke, injury or surgery) or transient ischemic stroke (from coronary bypass surgery or other transient ischemic conditions)}.

In another embodiment of a method of treating or ameliorating a disorder selected from the group consisting of diabetes-associated disorders, dermatological disorders, oncological disorders and central nervous system disorders comprising administering to a subject in need of treatment a therapeutically effective amount of a compound of Formula (I):

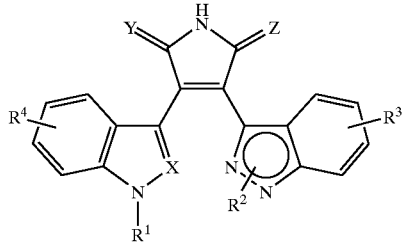

Formula (I)

wherein
$R^1$ and $R^2$ are independently selected from the group consisting of: hydrogen,
$C_{1-8}$alkyl, $C_{2-8}$alkenyl, $C_{2-8}$alkynyl {wherein alkyl, alkenyl and alkynyl are optionally substituted with one to two substituents independently selected from the group consisting of —O—$(C_{1-8})$alkyl, —O—$(C_{1-8})$alkyl-OH, —O—$(C_{1-8})$alkyl-O—$(C_{1-8})$alkyl, —O—$(C_{1-8})$alkyl-NH$_2$, —O—$(C_{1-8})$alkyl-NH—$(C_{1-8})$alkyl, —O—$(C_{1-8})$alkyl-N[$(C_{1-8})$alkyl]$_2$, —O—$(C_{1-8})$alkyl-S—$(C_{1-8})$alkyl, —O—$(C_{1-8})$alkyl-SO$_2$—$(C_{1-8})$alkyl, —O—$(C_{1-8})$alkyl-SO$_2$—NH$_2$, —O—$(C_{1-8})$alkyl-SO$_2$—NH—$(C_{1-8})$alkyl, —O—$(C_{1-8})$alkyl-SO$_2$—N[$(C_{1-8})$alkyl]$_2$, —O—C(O)H, —O—C(O)—$(C_{1-8})$alkyl, —O—C(O)—NH$_2$, —O—C(O)—NH—$(C_{1-8})$alkyl, —O—C(O)—N[$(C_{1-8})$alkyl]$_2$, —O—$(C_{1-8})$alkyl-C(O)H, —O—$(C_{1-8})$alkyl-C(O)—$(C_{1-8})$alkyl, —O—$(C_{1-8})$alkyl-CO$_2$H, —O—$(C_{1-8})$alkyl-C(O)—O—$(C_{1-8})$alkyl, —O—$(C_{1-8})$alkyl-C(O)—NH$_2$, —O—$(C_{1-8})$alkyl-C(O)—NH—$(C_{1-8})$alkyl, —O—$(C_{1-8})$alkyl-C(O)—N[$(C_{1-8})$alkyl]$_2$, —C(O)H, —C(O)—$(C_{1-8})$alkyl, —CO$_2$H, —C(O)—O—$(C_{1-8})$alkyl, —C(O)—NH$_2$, —C(NH)—NH$_2$, —C(O)—NH—$(C_{1-8})$alkyl, —C(O)—N[$(C_{1-8})$alkyl]$_2$, —SH, —S—$(C_{1-8})$alkyl, —S—$(C_{1-8})$alkyl-S—$(C_{1-8})$alkyl, —S—$(C_{1-8})$alkyl-O—$(C_{1-8})$alkyl, —S—$(C_{1-8})$alkyl-O—$(C_{1-8})$alkyl-OH, —S—$(C_{1-8})$alkyl-O—$(C_{1-8})$alkyl-NH$_2$, —S—$(C_{1-8})$alkyl-O—$(C_{1-8})$alkyl-NH—$(C_{1-8})$alkyl, —S—$(C_{1-8})$alkyl-O—$(C_{1-8})$alkyl-N[$(C_{1-8})$alkyl]$_2$, —S—$(C_{1-8})$alkyl-NH—$(C_{1-8})$alkyl, —SO$_2$—$(C_{1-8})$alkyl, —SO$_2$—NH$_2$, —SO$_2$—NH—$(C_{1-8})$alkyl, —SO$_2$—N[$(C_{1-8})$alkyl]$_2$, amino (substituted with two substituents independently selected from the group consisting of hydrogen, $C_{1-8}$alkyl, $C_{2-8}$alkenyl, $C_{2-8}$alkynyl, —$(C_{1-8})$alkyl-OH, —$(C_{1-8})$alkyl-O—$(C_{1-8})$alkyl, —$(C_{1-8})$alkyl-NH$_2$, —$(C_{1-8})$alkyl-NH—$(C_{1-8})$alkyl, —$(C_{1-8})$alkyl-N[$(C_{1-8})$alkyl]$_2$, —$(C_{1-8})$alkyl-S—$(C_{1-8})$alkyl, —C(O)—$(C_{1-8})$alkyl, —C(O)—O—$(C_{1-8})$alkyl, —C(O)—NH$_2$, —C(O)—NH—C(O)alkyl, —C(O)—N[$(C_{1-8})$alkyl]$_2$, —SO$_2$—$(C_{1-8})$alkyl, SO$_2$—NH$_2$, —SO$_2$—NH—$(C_{1-8})$alkyl, —SO2—N[$(C_{1-8})$alkyl]$_2$, —C(N)—NH$_2$, aryl and aryl$(C_{1-8})$alkyl (wherein aryl is optionally substituted with one to three substituents independently selected from the group consisting of halogen, $C_{1-8}$alkyl, $C_{1-8}$alkoxy, amino (substituted with two substituents selected from the group consisting of hydrogen and $C_{1-8}$alkyl), cyano, halo, (halo)$_{1-3}$($C_{1-8}$)alkyl, (halo)$_{1-3}$($C_{1-8}$)alkoxy, hydroxy, hydroxy($C_{1-8}$)alkyl and nitro)), cyano, (halo)$_{1-3}$, hydroxy, nitro, oxo, heterocyclyl, aryl and heteroaryl (wherein heterocyclyl, aryl and heteroaryl are optionally substituted with one to three substituents independently selected from the group consisting of $C_{1-8}$alkyl, $C_{1-8}$alkoxy, amino (substituted with two substituents selected from the group consisting of hydrogen and $C_{1-8}$alkyl), cyano, halo, (halo)$_{1-3}$($C_{1-8}$)alkyl, (halo)$_{1-3}$($C_{1-8}$)alkoxy, hydroxy, hydroxy($C_{1-8}$)alkyl and nitro)},
—C(O)—$(C_{1-8})$alkyl, —C(O)-aryl, —C(O)—O—$(C_{1-8})$alkyl, —C(O)—O-aryl, —C(O)—NH—$(C_{1-8})$alkyl, —C(O)—NH-aryl, —C(O)—N[$(C_{1-8})$alkyl]$_2$, —SO$_2$—$(C_{1-8})$alkyl, —SO$_2$-aryl,
aryl and heteroaryl {wherein aryl and heteroaryl are optionally substituted with one to three substituents independently selected from the group consisting of $C_{1-8}$alkyl, $C_{2-8}$alkenyl, $C_{2-8}$alkynyl, $C_{1-8}$alkoxy, —C(O)H, —C(O)—$(C_{1-8})$alkyl, —CO$_2$H, —C(O)—O—$(C_{1-8})$alkyl, —C(O)—NH$_2$, —C(NH)—NH$_2$, —C(O)—NH—$(C_{1-8})$alkyl, —C(O)—N[$(C_{1-8})$alkyl]$_2$, —SH, —S—$(C_{1-8})$alkyl, —SO$_2$—$(C_{1-8})$alkyl, —SO$_2$—NH$_2$, —SO$_2$—NH—$(C_{1-8})$alkyl, —SO$_2$—N[$(C_{1-8})$alkyl]$_2$, amino (substituted with two substituents independently selected from the group consisting of hydrogen, $C_{1-8}$alkyl, $C_{2-8}$alkenyl, $C_{2-8}$alkynyl, —$(C_{1-8})$alkyl-NH$_2$, —C(O)—$(C_{1-8})$alkyl, —C(O)—O—$(C_{1-8})$alkyl, —C(O)—NH$_2$, —C(O)—NH—$(C_{1-8})$alkyl, —C(O)—N[$(C_{1-8})$alkyl]$_2$, —SO$_2$—$(C_{1-8})$alkyl, —SO$_2$—NH$_2$, —SO$_2$—NH—$(C_{1-8})$ alkyl, —SO$_2$—N[(C$_{1-8}$)alkyl]$_2$ and —C(NH)—NH$_2$), amino-(C$_{1-8}$)alkyl- (wherein amino is substituted with two substituents independently selected from the group consisting of hydrogen, C$_{1-8}$alkyl, C$_{2-8}$alkenyl, C$_{2-8}$alkynyl, —(C$_{1-8}$)alkyl-NH$_2$, —C(O)—(C$_{1-8}$)alkyl, —C(O)—O—(C$_{1-8}$)alkyl, —C(O)—NH$_2$, —C(O)—NH—(C$_{1-8}$)alkyl, —C(O)—N[(C$_{1-8}$)alkyl]$_2$, —SO$_2$—(C$_{1-8}$)alkyl, —SO$_2$—NH$_2$, —SO$_2$—NH—(C$_{1-8}$)alkyl, SO$_2$—N[(C$_{1-8}$)alkyl]$_2$ and —C(NH)—NH$_2$), cyano, halo, (halo)$_{1-3}$(C$_{1-8}$)alkyl-, (halo)$_{1-3}$(C$_{1-8}$)alkoxy-, hydroxy, hydroxy(C$_{1-8}$)alkyl, nitro, aryl, —(C$_{1-8}$)alkyl-aryl, heteroaryl and —(C$_{1-8}$)alkyl-heteroaryl};

X is selected from the group consisting of N and CR$^5$;

R$^3$ and R$^4$ are independently selected from the group consisting of hydrogen, C$_{1-8}$alkyl, C$_{2-8}$alkenyl, C$_{2-8}$alkynyl, C$_{1-8}$alkoxy, —C(O)H, —C(O)—(C$_{1-8}$)alkyl, CO$_2$H, —C(O)—O—(C$_{1-8}$)alkyl, —C(O)—NH$_2$, —C(NH)—NH$_2$, —C(O)—NH—(C$_{1-8}$)alkyl, —C(O)—N[(C$_{1-8}$)alkyl]$_2$, —SH, —S—(C$_{1-8}$)alkyl, —SO$_2$—(C$_{1-8}$)alkyl, —SO$_2$—NH$_2$, —SO$_2$—NH—(C$_{1-8}$)alkyl, —SO$_2$—N[(C$_{1-8}$)alkyl]$_2$, amino (substituted with two substituents independently selected from the group consisting of hydrogen, C$_{1-8}$alkyl, C$_{2-8}$alkenyl, C$_{2-8}$alkynyl, —(C$_{1-8}$)alkyl-NH$_2$, —C(O)—(C$_{1-8}$)alkyl, —C(O)—O—(C$_{1-8}$)alkyl, —C(O)—NH$_2$, —C(O)—NH—(C$_{1-8}$)alkyl, —C(O)—N[(C$_{1-8}$)alkyl]$_2$, —SO$_2$—(C$_{1-8}$)alkyl, —SO$_2$—NH$_2$, —SO$_2$—NH—(C$_{1-8}$)alkyl, —SO$_2$—N[(C$_{1-8}$)alkyl]$_2$ and —C(NH)—NH$_2$), amino-(C$_{1-8}$)alkyl- (wherein amino is substituted with two substituents independently selected from the group consisting of hydrogen, C$_{1-8}$alkyl, C$_{2-8}$-alkenyl, C$_{2-8}$alkynyl, —(C$_{1-8}$)alkyl-NH$_2$, —C(O)—(C$_{1-8}$)alkyl, —C(O)—O—(C$_{1-8}$)alkyl, —C(O)—NH$_2$, —C(O)—NH—(C$_{1-8}$)alkyl, —C(O)—N[(C$_{1-8}$)alkyl]$_2$, —SO$_2$—(C$_{1-8}$)alkyl, —SO$_2$—NH$_2$, —SO$_2$—NH—(C$_{1-8}$)alkyl, —SO$_2$—N[(C$_{1-8}$)alkyl]$_2$ and —C(NH)—NH$_2$), cyano, halo, (halo)$_{1-3}$(C$_{1-8}$)alkyl-, (halo)$_{1-3}$(C$_{1-8}$)alkoxy-, hydroxy, hydroxy(C$_{1-8}$)alkyl-, nitro, aryl, —(C$_{1-8}$)alkyl-aryl, heteroaryl and —(C$_{1-8}$)alkyl-heteroaryl;

Y and Z are independently selected from the group consisting of O, S, (H,OH) and (H,H); with the proviso that one of Y and Z is O and the other is selected from the group consisting of O, S, (H,OH) and (H,H); and, R$^5$ is selected from the group consisting of:
hydrogen, halogen,
C$_{1-8}$alkyl, C$_{2-8}$alkenyl, C$_{2-8}$alkynyl {wherein alkyl, alkenyl and alkynyl are optionally substituted with one to two substituents independently selected from the group consisting of amino (substituted with two substituents selected from the group consisting of hydrogen and C$_{1-8}$alkyl), cyano, halo, hydroxy, nitro, oxo, aryl and heteroaryl},
aryl and heteroaryl {wherein aryl and heteroaryl are optionally substituted with one to two substituents independently selected from the group consisting of C$_{1-8}$alkyl, C$_{1-8}$alkoxy, amino (substituted with two substituents selected from the group consisting of hydrogen and C$_{1-8}$alkyl), cyano, halo, hydroxy and nitro};
and pharmaceutically acceptable salts thereof.

A compound may be administered to a subject in need of treatment by any conventional route of administration including, but not limited to oral, nasal, sublingual, ocular, transdermal, rectal, vaginal and parenteral (i.e. subcutaneous, intramuscular, intradermal, intravenous etc.).

To prepare the pharmaceutical compositions of this invention, one or more compounds of Formula (I) or salt thereof as the active ingredient, is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets*, Second Edition, Revised and Expanded, Volumes 1–3, edited by Lieberman, et al.; *Pharmaceutical Dosage Forms: Parenteral Medications*, Volumes 1–2, edited by Avis, et al.; and *Pharmaceutical Dosage Forms: Disperse Systems*, Volumes 1–2, edited by Lieberman, et al.; published by Marcel Dekker, Inc.

In preparing a pharmaceutical composition of the present invention in liquid dosage form for oral, topical and parenteral administration, any of the usual pharmaceutical media or excipients may be employed. Thus, for liquid dosage forms, such as suspensions (i.e. colloids, emulsions and dispersions) and solutions, suitable carriers and additives include but are not limited to pharmaceutically acceptable wetting agents, dispersants, flocculation agents. thickeners, pH control agents (i e. buffers), osmotic agents, coloring agents, flavors, fragrances, preservatives (i.e. to control microbial growth, etc.) and a liquid vehicle may be employed. Not all of the components listed above will be required for each liquid dosage form.

In solid oral preparations such as, for example, powders, granules, capsules, caplets, gelcaps, pills and tablets (each including immediate release, timed release and sustained release formulations), suitable carriers and additives include but are not limited to diluents, granulating agents, lubricants, binders, glidants, disintegrating agents and the like. Because of their ease of administration, tablets and capsules represent the most advantageous oral dosage unit form, in which case solid pharmaceutical carriers are obviously employed. If desired, tablets may be sugar coated, gelatin coated, film coated or enteric coated by standard techniques.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.001 mg to about 300 mg (preferably, from about 0.01 mg to about 100 mg; and, more preferably, from about 0.1 mg to about 30 mg) and may be given at a dosage of from about 0.001 mg/kg/day to about 300 mg/kg/day (preferably, from about 0.01 mg/kg/day to about 100 mg/kg/day, and, more preferably, from about 0.1 mg/kg/day to about 30 mg/kg/day). Preferably, in the method for treating or ameliorating a kinase or dual-kinase mediated disorder described in the present invention and using any of the compounds as defined herein, the dosage form will contain a pharmaceutically acceptable carrier containing between about 0.01 mg and 100 mg; and, more preferably, between about 5 mg and 50 mg of the compound; and, may be constituted into any form suitable for the mode of administration selected. The dosages, however, may be varied depending upon the requirement of the subjects, the severity of the condition being treated and the compound being employed. The use of either daily administration or post-periodic dosing may be employed.

Preferably these compositions are in unit dosage forms such as tablets, pills, capsules, powders, granules, lozenges, sterile parenteral solutions or suspensions, metered aerosol or liquid sprays, drops, ampoules, autoinjector devices or suppositories for administration by oral, intranasal, sublingual, intraocular, transdermal, parenteral, rectal, vaginal, inhalation or insufflation means. Alternatively, the composition may be presented in a form suitable for once-weekly or once-monthly administration; for example, an insoluble salt of the active compound, such as the decanoate salt, may be adapted to provide a depot preparation for intramuscular injection.

For preparing solid pharmaceutical compositions such as tablets, the principal active ingredient is mixed with a pharmaceutical carrier, e.g. conventional tableting ingredients such as diluents, binders, adhesives, disintegrants, lubricants, antiadherents and glidants. Suitable diluents include, but are not limited to, starch (i.e. corn, wheat, or potato starch, which may be hydrolized), lactose (granulated, spray dried or anhydrous), sucrose, sucrose-based diluents (confectioner's sugar; sucrose plus about 7 to 10 weight percent invert sugar; sucrose plus about 3 weight percent modified dextrins; sucrose plus invert sugar, about 4 weight percent invert sugar, about 0.1 to 0.2 weight percent cornstarch and magnesium stearate), dextrose, inositol, mannitol. sorbitol, microctystalline cellulose (i.e. AVICEL™ microcrystalline cellulose available from FMC Corp.), dicalcium phosphate, calcium sulfate dihydrate. calcium lactate trihydrate and the like. Suitable binders and adhesives include, but are not limited to acacia gum, guar gum, tragacanth gum, sucrose, gelatin, glucose, starch, and cellulosics (i.e. methylcellulose, sodium carboxymethycellulose, ethylcellulose, hydroxypropylmethylcellulose, hydroxypropylcellulose, and the like), water soluble or dispersible binders (i.e. alginic acid and salts thereof, magnesium aluminum silicate, hydroxyethylcellulose (i.e. TYLOSE™ available from Hoechst Celanese), polyethylene glycol, polysaccharide acids, bentonites, polyvinylpyrrolidone, polymethacrylates and pregelatinized starch) and the like. Suitable disintegrants include, but are not limited to, starches (corn, potato, etc.), sodium starch glycolates, pregelatinized starches, clays (magnesium aluminum silicate), celluloses (such as crosslinked sodium carboxymethylcellulose and microcrystalline cellulose), alginates, pregelatinized starches (i.e. corn starch, etc.), gums (i.e. agar, guar, locust bean, karaya, pectin and tragacanth gum), crosslinked polyvinylpyrrolidone and the like. Suitable lubricants and antiadherents include, but are not limited to, stearates (magnesium, calcium and sodium), stearic acid, talc waxes, stearowet, boric acid, sodium chloride, DL-leucine, carbowax 4000, carbowax 6000, sodium oleate, sodium benzoate, sodium acetate, sodium lauryl sulfate, magnesium lauryl sulfate and the like. Suitable glidants include, but are not limited to, talc, cornstarch, silica (i.e. CAB-O-SIL™ silica available from Cabot, SYLOID™ silica available from W. R. Grace/Davison and AEROSIL™ silica available from Degussa) and the like. Sweeteners and flavorants may be added to chewable solid dosage forms to improve the palatability of the oral dosage form. Additionally, colorants and coatings may be added or applied to the solid dosage form for ease of identification of the drug or for aesthetic purposes. These carriers are formulated with the pharmaceutical active to provide an accurate, appropriate dose of the pharmaceutical active with a therapeutic release profile.

Generally these carriers are mixed with the pharmaceutical active to form a solid preformulation composition containing a homogeneous mixture of the pharmaceutical active of the present invention, or a pharmaceutically acceptable salt thereof. Generally the preformation will be formed by one of three common methods: (a) wet granulation, (b) dry granulation and (c) dry blending. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from about 0.1 mg to about 500 mg of the active ingredient of the present invention. The tablets or pills containing the novel compositions may also be formulated in multilayer tablets or pills to provide a sustained or provide dual-release products. For example, a dual release tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of materials can be used for such enteric layers or coatings, such materials including a number of polymeric materials such as shellac, cellulose acetate (i.e. cellulose acetate phthalate), polyvinyl acetate phthalate, hydroxypropyl methylcellulose phthalate, hydroxypropyl methylcellulose acetate succinate, methacrylate and ethylacrylate copolymers, methacrylate and methyl methacrylate copolymers and the like. Sustained release tablets may also be made by film coating or wet granulation using slightly soluble or insoluble substances in solution (which for a wet granulation acts as the binding agents) or low melting solids a molten form (which in a wet granulation may incorporate the active ingredient). These materials include natural and synthetic polymers waxes, hydrogenated oils, fatty acids and alcohols (i.e. beeswax, carnauba wax, cetyl alcohol, cetyl-stearyl alcohol and the like), esters of fatty acids metallic soaps and other acceptable materials that can be used to granulate, coat, entrap or otherwise limit the solubility of an active ingredient to achieve a prolonged or sustained release product.

The liquid forms in which the novel compositions of the present invention may be incorporated for administration orally or by injection include, but are not limited to aqueous solutions, suitably flavored syrups, aqueous or oil suspensions and flavored emulsions with edible oils such as cottonseed oil, sesame oil, coconut oil or peanut oil, as well as elixirs and similar pharmaceutical vehicles. Suitable suspending agents for aqueous suspensions, include synthetic and natural gums such as, acacia, agar, alginate (i.e. propylene alginate, sodium alginate and the like), guar, karaya, locust bean, pectin, tragacanth and xanthan gum, cellulosics such as sodium carboxymethylcellulose, methylcellulose, hydroxymethylcellulose, hydroxyethylcellulose, hydroxypropyl cellulose and hydroxypropyl methylcellulose and combinations thereof, synthetic polymers such as polyvinyl pyrrolidone, carbomer (i.e. carboxypolymethylene) and polyethylene glycol; clays such as bentonite, hectorite, attapulgite or sepiolite; and other pharmaceutically acceptable suspending agents such as lecithin, gelatin or the like. Suitable surfactants include but are not limited to sodium docusate, sodium lauryl sulfate, polysorbate, octoxynol-9, nonoxynol-10, polysorbate 20, polysorbate 40, polysorbate 60, polysorbate 80, polyoxamer 188, polyoxamer 235 and combinations thereof. Suitable deflocculating or dispersing agent include pharmaceutical grade lecithins. Suitable flocculating agent include but are not limited to simple neutral electrolytes (i.e. sodium chloride, potassium, chloride and the like), highly charged insoluble polymers and polyelectrolyte species, water soluble divalent or trivalent ions (i.e. calcium salts, alums or sulfates, citrates and phosphates (which can be used jointly in formulations as pH buffers and flocculating agents). Suitable preservatives include but are not limited to parabens (i.e. methyl, ethyl, n-propyl and n-butyl), sorbic acid, thimerosal, quaternary ammonium salts, benzyl alcohol, benzoic acid, chlorhexidine gluconate, phenylethanol and the like. There are many liquid vehicles that may be used in liquid pharmaceutical dosage forms, however, the liquid vehicle that is used in a particular dosage form must be compatible with the suspending agent(s). For example, nonpolar liquid vehicles such as fatty esters and oils liquid vehicles are best used with suspending agents such as low HLB (Hydrophile-Lipophile Balance) surfartants, stearalkonium hectorite, water insoluble resins, water insoluble film forming polymers and the like. Conversely, polar liquids such as water, alcohols, polyols and glycols are best used with suspending agents such as higher HLB surfactants, clays silicates, gums, water soluble cellulosics, water soluble polymers and the like. For parenteral administration, sterile suspensions and solutions are desired. Liquid forms useful for parenteral administration include sterile solutions, emulsions and suspensions. Isotonic preparations which generally contain suitable preservatives are employed when intravenous administration is desired.

Furthermore, compounds of the present invention can be administered in an intranasal dosage form via topical use of suitable intranasal vehicles or via transdermal skin patches, the composition of which are well known to those of ordinary skill in that art. To be administered in the form of a transdermal delivery system, the administration of a therapeutic dose will, of course, be continuous rather than intermittent throughout the dosage regimen.

Compounds of the present invention can also be administered in the form of liposome delivery systems, such as small unilamellar vesicles, large unilamellar vesicles, multilamellar vesicles and the like. Liposomes can be formed from a variety of phospholipids, such as cholesterol, stearylamine, phosphatidylcholines and the like.

Compounds of the present invention may also be delivered by the use of monoclonal antibodies as individual carriers to which the compound molecules are coupled. The compounds of the present invention may also be coupled with soluble polymers as targetable drug carriers. Such polymers can include, but are not limited to polyvinylpyrrolidone, pyran copolymer, polyhydroxypropylmethacrylamidephenol, polyhydroxyethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, to homopolymers and copolymers (which means polymers containing two or more chemically distinguishable repeating units) or lactide (which includes lactic acid d-, l- and meso lactide), glyrolide (including glycolic acid), ε-caprolactone, p-dioxanone (1,4-dioxan-2-one), trimethylene carbonate (1,3-dioxan-2-one), alkyl derivatives of trimethylene carbonate, δ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one, polyorthoesters, polyacetals, polydihydropyrans, polycyanoacrylates and cross-linked or amphipathic block copolymers of hydrogels and blends thereof.

Compounds of this invention may be administered in any of the foregoing compositions and dosage regimens or by means of those compositions and dosage regimens established in the art whenever treating or ameliorating a kinase or dual-kinase mediated disorder is required for a subject in need thereof; in particular, whenever treating or ameliorating a kinase disorder mediated by selective inhibition of a kinase selected from protein kinase C or glycogen synthase kinase-3 is required; and, whenever treating or ameliorating a kinase disorder mediated by dual inhibition of at least two kinases selected from protein kinase C and glycogen synthase kinase-3 is required; and, more particularly, whenever treating or ameliorating a kinase disorder mediated by selective inhibition of a kinase selected from protein kinase C α, protein kinase C β-II, protein kinase C γ or glycogen synthase kinase-3β is required; and, whenever treating or ameliorating a kinase disorder mediated by dual inhibition of at least two kinases selected from protein kinase C α, protein kinase C β-II, protein kinase C γ or glycogen synthase kinase-3β is required.

The daily dose of a pharmaceutical composition of the present invention may be varied over a wide range from about 0.7 mg to about 21,000 mg per 70 kilogram (kg) adult human per day; preferably in the range of from about 7 mg to about 7,000 mg per adult human per day: and, more preferably, in the range of from about 7 mg to about 2,100 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the subject to be treated. A therapeutically effective amount of the drug is ordinarily supplied at a dosage level of from about 0.001 mg/kg to about 300 mg/kg of body weight per day. Preferably, the range is from about 0.1 mg/kg to about 100 mg/kg of body weight per day; and, most preferably, from about 0.1 mg/kg to about 30 mg/kg of body weight per day. Advantageously, compounds of the present invention may be administered in a single daily dose or the total daily dosage may be administered in divided doses of two, three or four times daily.

Optimal dosages to be administered may be readily determined by those skilled in the art and will vary with the particular compound used, the mode of administration, the strength of the preparation and the advancement of the disease condition. In addition, factors associated with the particular subject being treated, including subject age, weight, diet and time of administration, will result in the need to adjust the dose to an appropriate therapeutic level.

Abbreviations used in the instant specification, particularly the Schemes and Examples, are as follows:

| | | |
|---|---|---|
| ATP | = | adenosinetriphosphate |
| BSA | = | bovine serum albumin |
| DCM | = | dichloromethane |
| DMF | = | N,N-dimethylformamide |
| DMSO | = | dimethylsulfoxide |
| EDTA | = | ethylenediaminetetraacetic acid |
| EGTA | = | ethylenebis(oxyethylenenitrilo)tetraacetic acid |
| h | = | hour |
| HEPES | = | 4-(2-hydroxyethyl)-1-piperazine-ethanesulfonic acid |
| min | = | minute |
| rt | = | room temperature |
| TCA | = | trichloroacetic acid |

-continued

| THF | = | tetrahydrofuran |
| --- | --- | --- |
| TFA | = | trifluoroacetic acid |
| TMSCHN$_2$ | = | trimethylsilyldiazomethane |

General Synthetic Methods

Representative compounds of the present invention can be synthesized in accordance with the general synthetic methods described below and are illustrated more particularly in the schemes that follow. Since the schemes are an illustration, the invention should not be construed as being limited by the chemical reactions and conditions expressed. The preparation of the various starting materials used in the schemes is well within the skill of persons versed in the art.

The following schemes describe general synthetic methods whereby intermediate and target compounds of the present invention may be prepared. Additional representative compounds of the present invention can be synthesized using the intermediates prepared in accordance with the schemes and other materials, compounds and reagents known to those skilled in the art.

In Scheme AA, the substituted indole Compound AA1 was arylated with an appropriately substituted aryl or heteroaryl halide and a base such as cesium or potassium carbonate and copper oxide in a dipolar aprotic solvent such as DMF to give Compound AA2. Compound AA2 was acylated with oxalyl chloride in an aprotic solvent such as diethyl ether or DCM and quenched with sodium methoxide to afford an intermediate glyoxylic ester Compound AA3.

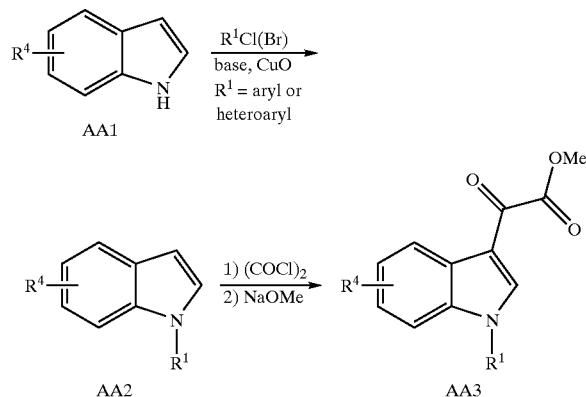

Another intermediate Compound AA5 was prepared from Compound AA1 via acylation with oxalyl chloride followed by treatment with sodium methoxide to afford glyoxylic ester Compound AA4 which was then alkylated with 1,2-dibromoethane under basic conditions to derive Compound AA5.

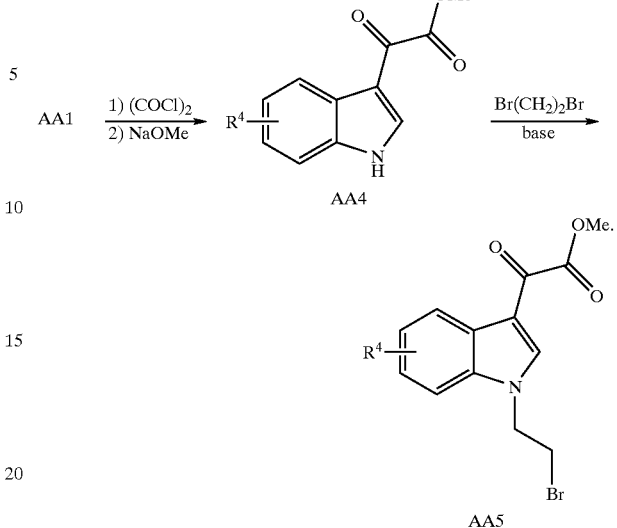

The intermediate Compound AA6 was prepared from Compound AA4 via alkylation with an appropriate alkylating agent under basic conditions.

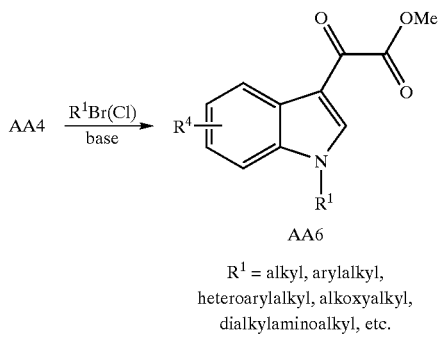

$R^1$ = alkyl, arylalkyl,
heteroarylalkyl, alkoxyalkyl,
dialkylaminoalkyl, etc.

The substituted 3-indazoleacetic acid Compound AA8 was prepared from aldehyde Compound AA7 by reaction with malonic acid and ammonium formate followed by reductive cyclization under basic conditions (B. Mylari, et al., *J. Med. Chem.*, 1992, 35, 2155). The acid Compound AA8 was coupled with ammonium hydroxide in an aprotic solvent such as DCM or acetonitrile using a dehydrating agent like dicyclohexyl carbodiimide (DCC) and 1-hydroxybenzotriazole (HOBT) to give amide Compound AA9, which was treated with an appropriate alkylating agent in the presence of a base such as sodium hydride to afford indazole Compound AA10 as a mixture of N1-alkylated (major) and N2-alkylated (minor) products.

Target Compound AA11, having a variety of $R^1$ and $R^2$ substituents, may be prepared using Compound AA3, Compound AA5 or Compound AA6 in reaction with the amide Compound AA10.

The ester Compound AA3 (wherein $R^1$ is an aryl or heteroaryl) may he reacted with the amide Compound AA10 stirred in an aprotic solvent such as THF with ice bath cooling and a base, such as potassium tert-butoxide or sodium hydride, to give a target Compound AA11. Alternatively, the ester Compound AA5 may be condensed with Compound AA10 under strong basic conditions, concomitantly causing the elimination of HBr, to give a target Compound AA11 (wherein $R^1$ is vinyl) as the product. Also, the ester Compound AA6 (wherein $R^1$ is selected from alkyl, arylalkyl, heteroarylalkyl, alkoxyalkyl, dialkylaminoalkyl, etc.) may reacted with Compound AA10 under basic conditions to give a target Compound AA11 as the product.

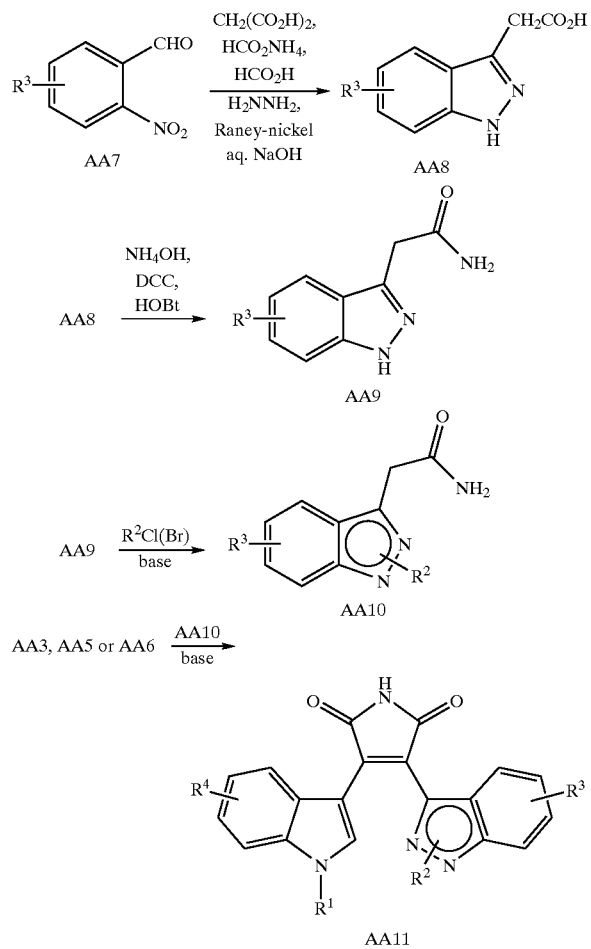

Specific Synthetic Methods

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents. All chemicals were obtained from commercial suppliers and used without further purification. $^1$H and $^{13}$C NMR spectra were recorded on a Bruker AC 300B (300 MHz proton) or a Bruker AM-400 (400 MHz proton) spectrometer with $Me_4Si$ as an internal standard (s=singlet, d=doublet, t=triplet, br=broad). APCI-MS and ES-MS were recorded on a VG Platform II mass spectrometer; methane was used for chemical ionization, unless noted otherwise. Accurate mass measurements were obtained by using a VG ZAB 2-SE spectrometer in the FAB mode. TLC was performed with Whatman 250-μm silica gel plates. Preparative TLC was performed with Analtech 1000-μm silica gel GF plates. Flash column chromatography was conducted with flash column silica gel (40–63 μm) and column chromatography was conducted with standard silica gel. HPLC separations were carried out on three Waters PrepPak® Cartridges (25×100 mm, Bondapak® C18, 15–20 μm, 125 Å) connected in series; detection was at 254 nm on a Waters 486 UV detector Analytical HPLC was carried out on a Supelcosil ABZ+PLUS column (5 cm×2.1 mm), with detection at 254 nm on a Hewlett Packard 1100 UV detector. Microanalysis was performed by Robertson Microlit Laboratories, Inc.

Representative Chemical Abstracts Service (CAS) Index-like names for the compounds of the present invention were derived using the ACD/LABS SOFTWARE™ Index Name Pro Version 4.5 nomenclature software program provided by Advanced Chemistry Development, Inc., Toronto, Ontario, Canada.

EXAMPLE 1

3-[1-[3-(dimethylamino)propyl]-1H-indazol-3-yl]4-[1-(3-pyridinyl)-1H-indol-3-yl]-H-pyrrole-2,5-dione (Compound 12)

Indole Compound 1a (2.34 g, 20 mmol) and 3-bromopyridine (3.16 g, 20 mmol) were dissolved in DMF (10 mL) and potassium carbonate (2.76 g, 20 mmol). CuO (130 mg, 1.6 mmol) was added and the reaction was refluxed under argon for 16 h. The reaction was cooled to rt and partitioned between DCM (100 mL) and water (100 mL). The organic layer was washed with water (3×50 mL) and brine (2×50 mL), then dried ($Na_2SO_4$) and evaporated in vacuo to a brown oil. The product was purified via flash column chromatography (ethyl acetate:hexane; 1:1) to give Compound 1b (3.16 g, 81%) as a colorless oil. The indole Compound 1b (0.78 g, 4.0 mmol) in DCM (12 mL) was treated with oxalyl chloride (0.52 g, 4.1 mmol) with ice bath cooling and then stirred at ambient temperature for 16 h. The solution was cooled to –65° C. and sodium methoxide (0.46 g, 8.0 mmol) in methanol (10 mL) was added slowly; the reaction was stirred at ambient temperature for 1 h and then evaporated in vacuo to a solid. The solid was extracted with chloroform (25 mL), filtered and the filtrate dried ($K_2CO_3$) and evaporated in vacuo to provide Compound 1c (0.73 g, 65%) as a grey solid. $^1$H NMR ($CDCl_3$) δ 8.88 (d, J=2.3 Hz, 1H), 8.77 (dd, J=4.7, 1.3 Hz, 1H), 8.60 (s, 1H), 8.54 (d, J=7.1 Hz, 1H), 7.90 (m, 1H), 7.56 (m, 1H), 7.43 (m, 3H), 3.98 (s, 3H). ES-MS m/z 281 (MH$^+$).

Using the procedure described for preparing Compound 2e (see Example 2), acid Compound 1d (5.28 g, 30 mmol) was dissolved in DCM (120 mL) and DMF (30 mL) under argon. HOBT (4.45 g, 33 mmol) and DCC (6.51 g, 32 mmol) were added and the reaction was stirred at ambient temperature for 1 h. Ammonium hydroxide (28%, 2.7 g, 44 mmol) was added over 5 min and the reaction was then stirred at ambient temperature for 16 h. A white solid was filtered off. The filtrate was diluted with DCM (150 mL) and filtered again. The DCM solution was extracted four times with 5% $NaHCO_3$ (150 mL). The combined aqueous solution was treated with sodium chloride (190 g) and extracted with ethyl acetate (6×300 mL). The organic extract was dried ($Na_2SO_4$) and evaporated in vacuo to a solid (6.25 g), which was triturated with diethyl ether (100 mL) and filtered to afford Compound 1e (3.52 g, 67%) as a white solid.

Indazole Compound 1e (2.62 g, 15 mmol) in DMF (35 mL) was combined with 3-dimethylaminopropylchloride hydrochloride (2.61 g, 16.5 mmol) and cooled in an ice bath as 95% sodium hydride (0.80 g, 31.5 mmol) was added portionwise over a 20 min period. The reaction was stirred at ambient temperature for 10 min and then placed in an oilbath at 55° C. for 3 h. After cooling to rt, the reaction was diluted with DCM (200 mL) and washed with 0.3N NaOH (200 mL), water (2×100 mL) and brine (50 mL), then dried ($K_2CO_3$) and evaporated in vacuo to a first crop of light yellow solid (2.50 g). The aqueous solutions were re-extracted with DCM (3×100 mL) and the DCM was washed with brine, then dried ($K_2CO_3$) and evaporated in vacuo to give a second crop (1.63 g). These two crops were combined and purified by flash column chromatography (DCM:MeOH:$NH_4OH$; 90:9:1) to afford Compound 1f (2.63 g, 64%) as a white solid.

The ester Compound 1c (700 mg, 2.5 mmol) and amide Compound 1f (546 mg, 2.1 mmol) were combined in dry THF (10 mL) under argon and cooled with an ice bath as 1M potassium t-butoxide in THF (8.4 mL, 8.4 mmol) was added with stirring over a 20 min period. After 1 h, the reaction was quenched in an ice bath, 12 N HCl (3.5 mL, 42 mmol) was slowly added over a 3 min period. The mixture was stirred for 5 min and then partitioned between chloroform:2-propanol (10:1; 200 mL) and saturated $NaHCO_3$. The organic solution was washed with brine, then dried ($Na_2SO_4$) and evaporated in vacuo to a flaky solid. The solid was then purified by flash column chromatography (90:9:1; DCM:MeOH.$NH_4OH$) to afford Compound 12 (0.70 g, 68%) as an orange flaky solid. A portion of Compound 12 was dissolved in excess dilute HCl, then frozen and lyophilized to give the hydrochloride salt. $^1H$ NMR (DMSO) δ 8.97 (s, 1H), 8.75 (bd s, 1H), 8.40 (s, 1H), 8.27 (d, J=9.2 Hz, 1H), 7.78 (m, 3H), 7.51 (m, 2H), 7.18 (m, 2H), 6.88 (dd, J=7.5, 7.7 Hz, 1H), 6.49 (d, J=8.0 Hz, 1H), 4.47 (m, 2H), 2.94 (m, 2H), 2.58 (s, 6H), 2.01 (m, 2H). ES-MS m/z 491 ($MH^+$). Anal. Calcd. for $C_{29}H_{26}N_6O_2 \cdot 2HCl \cdot 2.5H_2O$ (490.56/608.52): C, 57.24:H, 5.46; N, 13.81; $H_2O$, 7.40. Found: C, 57.06; H, 5.26; N, 13.89; $H_2O$, 6.92.

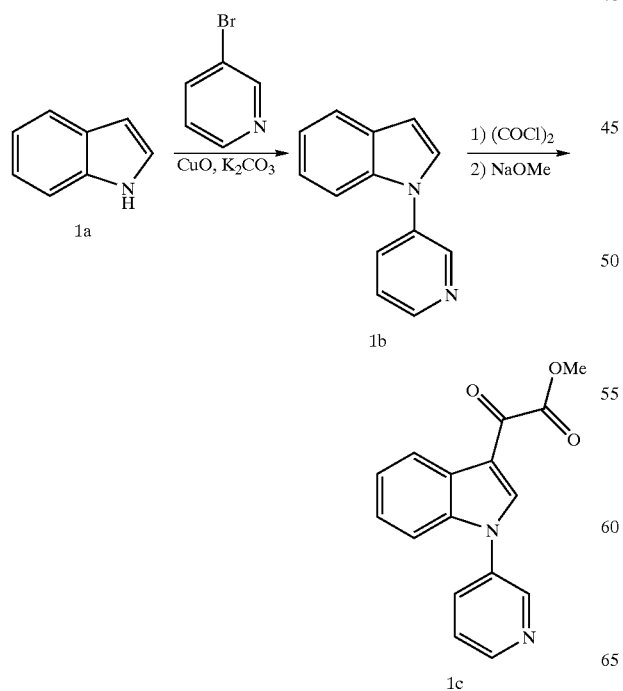

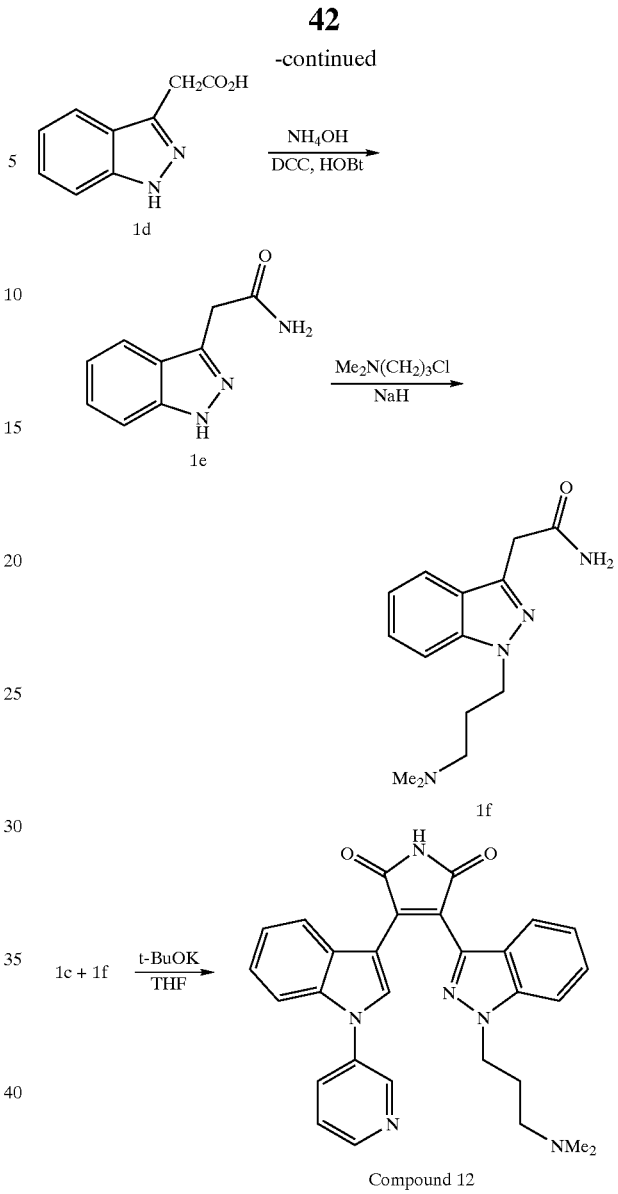

Compound 12

Using the procedure of Example 1 and the appropriate reagents and starting materials known to those skilled in the art, other compounds of the present invention may be prepared including, but not limited to:

| Cpd | Name | ES-MS m/z ($MH^+$) |
|---|---|---|
| 8 | 3-[1-[3-(dimethylamino)propyl]-1H-indazol-3-yl]-4-[1-(3-thienyl)-1H-indol-3-yl]-1H-pyrrole-2,5-dione | 496 |
| 11 | 3-[1-[3-(dimethylamino)propyl]-1H-indazol-3-yl]-4-[1-(3-furanyl)-1H-indol-3-yl]-1H-pyrrole-2,5-dione | 480 |
| 13 | 3-[5-chloro-1-(3-pyridinyl)-1H-indol-3-yl]-4-[1-[3-(dimethylamino)propyl]-1H-indazol-3-yl]-1H-pyrrole-2,5-dione | 525 |
| 17 | 3-[2-(2-naphthalenyl)-1-(3-pyridinyl)-1H-indol-3-yl]-4-[1-[3-(dimethylamino)propyl]-1H-indazol-3-yl]-1H-pyrrole-2,5-dione | 617 |
| 18 | 3-[6-chloro-1-(3-pyridinyl)-1H-indol-3-yl]-4-[1-[3-(dimethylamino)propyl]-1H-indazol-3-yl]-1H-pyrrole-2,5-dione | 525 |

-continued

| Cpd | Name | ES-MS m/z (MH+) |
|---|---|---|
| 19 | 3-[1-[3-(dimethylamino)propyl]-1H-indazol-3-yl]-4-[1-(3-quinolinyl)-1H-indol-3-yl]-1H-pyrrole-2,5-dione | 541 |
| 21 | 3-[1-[3-(diethylamino)propyl]-1H-indazol-3-yl]-4-[1-(3-quinolinyl)-1H-indol-3-yl]-1H-pyrrole-2,5-dione | 569 |
| 22 | 3-[1-[3-(4-morpholinyl)propyl]-1H-indazol-3-yl]-4-[1-(3-quinolinyl)-1H-indol-3-yl]-1H-pyrrole-2,5-dione | 583 |
| 23 | 3-[2,5-dihydro-2,5-dioxo-4-[1-(3-quinolinyl)-1H-indol-3-yl]-1H-pyrrol-3-yl]-1H-indazole-1-propionaldehyde | 512 |
| 24 | 3-[1-[2-(1,3-dioxolan-2-yl)ethyl]-1H-indazol-3-yl]-4-[1-(3-quinolinyl)-1H-indol-3-yl]-1H-pyrrole-2,5-dione | 556 |
| 25 | 3-[1-[3-(dimethylamino)propyl]-1H-indazol-3-yl]-4-[5-methoxy-1-(3-pyridinyl)-1H-indol-3-yl]-1H-pyrrole-2,5-dione | 521 |
| 27 | 3-[1-[3-(dimethylamino)propyl]-1H-indazol-3-yl]-4-[1-(6-methyl-3-pyridinyl)-1H-indol-3-yl]-1H-pyrrole-2,5-dione | 505 |
| 31 | 3-[1-[3-(dimethylamino)propyl]-1H-indazol-3-yl]-4-[1-(2-pyridinyl)-1H-indol-3-yl]-1H-pyrrole-2,5-dione | 491 |
| 32 | 3-[1-[3-(dimethylamino)propyl-1H-indazol-3-yl]-4-[1-(4-pyridinyl)-1H-indol-3-yl]-1H-pyrrole-2,5-dione | 491 |
| 33 | 3-[5-chloro-1-(2-thienyl)-1H-indol-3-yl]-4-[1-[3-(dimethylamino)propyl]-1H-indazol-3-yl]-1H-pyrrole-2,5-dione | 530 |
| 35 | 3-[1-(5-bromo-2-pyridinyl)-1H-indol-3-yl]-4-[1-[3-(dimethylamino)propyl]-1H-indazol-3-yl]-1H-pyrrole-2,5-dione | 569 |
| 38 | 3-[1-[3-(dimethylamino)propyl]-1H-indol-3-yl]-4-(1H-indazol-3-yl)-1H-pyrrole-2,5-dione | 414 |
| 62 | 3-[1-[3-(dimethylamino)propyl]-1H-indazol-3-yl]-4-[1-(2,5-dimethyl-3-pyridinyl)-1H-indol-3-yl]-1H-pyrrole-2,5-dione | 519 |
| 63 | 3-[1-[3-(dimethylamino)propyl]-1H-indazol-3-yl]-4-[1-(6-methoxy-2-naphthalenyl)-1H-indol-3-yl]-1H-pyrrole-2,5-dione | 570 |
| 64 | 3-[1-[3-(dimethylamino)propyl]-1H-indazol-3-yl]-4-[1-(6-hydroxy-2-naphthalenyl)-1H-indol-3-yl]-1H-pyrrole-2,5-dione | 556 |
| 65 | 3-[1-[3-(dimethylamino)propyl]-1H-indazol-3-yl]-4-[1-(6-quinolinyl)-1H-indol-3-yl]-1H-pyrrole-2,5-dione | 541 |
| 93 | 3-(1-benzo[b]thien-3-yl-1H-indol-3-yl)-4-[1-[4-(dimethylamino)butyl]-1H-indazol-3-yl]-1H-pyrrole-2,5-dione | 560 |
| 97 | 3-[1-[4-(dimethylamino)butyl]-1H-indazol-3-yl]-4-[1-(2-naphthalenyl)-1H-indol-3-yl]-1H-pyrrole-2,5-dione | 554 |
| 101 | 3-[1-[2-(dimethylamino)ethyl]-1H-indazol-3-yl]-4-[1-(2-naphthalenyl)-1H-indol-3-yl]-1H-pyrrole-2,5-dione | 526 |
| 103 | 3-(1-benzo[b]thien-3-yl-1H-indol-3-yl)-4-[1-[2-(dimethylamino)ethyl]-1H-indazol-3-yl]-1H-pyrrole-2,5-dione | 532 |

EXAMPLE 2

3-[5-chloro-1-[3-(dimethylamino)-2-hydroxypropyl]-1H-indazol-3-yl]-4-(1-ethenyl-1H-indol-3-yl)-1H-pyrrole-2,5-dione (Compound 4)

A suspension of 10.0 g (0.053 mole) of Compound 2a in a dichloromethane:methanol 6:1 mixture (350 mL) was stirred and cooled in an ice bath while adding 79 mL of a 2.0 M solution of TMSCHN$_2$ in hexane dropwise over a 1 hr period. The mixture was allowed to warm to rt and stirring continued over night. The resulting light yellow solid was filtered and washed with ether to yield Compound 2b (7.5 g, 70%). $^1$H NMR (DMSO-d$_6$) δ 12.5 (s, 1H), 8.45 (d, 1H), 8 2 (d, 1H), 7.55 (d, 1H), 7.3 (m, 2H), 3.95 (s, 3H).

Compound 2b (4.0 g, 0.0197 mole) and 1,2-dibromoethane (18.5 g, 0.0985 mole) were combined in anhydrous DMF (80 mL) and treated with cesium carbonate (12.8 g, 0.0394 mole). The mixture was stirred under an atmosphere of argon at rt for 1 h. The temperature was raised to 50° C. for 4 h, then the mixture was stirred at rt over night. The resulting white solids were removed by filtration. The filtrate was partitioned between 600 mL of ether and 300 mL of water. The organic layer was washed with water (3×) and brine, then dried over anhydrous sodium sulfate. The solvent was removed in vacuo and the resulting oily residue triturated with hexane to give a crude solid product. The crude solid was recrystallized from ethyl acetate/hexane and flash chromatographed on silica eluted with ethyl acetate/hexane to give Compound 2c (5.5 g, 47%).

Compound 2d (48 g, 0.22 mole), ammonium acetate (25.4 g, 0.33 mole) and malonic acid (22.9 g, 0.22 mole) in absolute ethanol (200 mL) were heated to reflux for a period of 9 h while stirring under an atmosphere of argon. The hot suspension was filtered and the solids were washed with ethanol followed by ether to give a tan solid (21.0 g, 0.086 mole). The tan solid was dissolved in 5% aqueous sodium hydroxide (125 mL) then treated with hydrazine monohydrate (4.8 g, 0.095 mole). The resulting mixture was warmed to 80° C., Raney-Nickel (about 70 mg) was then added cautiously to the hot solution in two portions while stirring. The reaction mixture temperature rose to about 90° C. and gas evolution was noted. Heating was continued for another 20 min until the gas evolution stopped and then the mixture cooled to rt. The solids were removed by filtration and the filtrate adjusted to pH 2 with 6N hydrochloric acid to give a golden solid. The solid was filtered, washed with water and air dried to give Compound 2e (14.6 g, 81%) as a light tan solid. $^1$H NMR (DMSO-d$_6$) δ 13.1 (s, 1H), 7.85 (s, 1H), 7.55 (d, 1H), 7.35 (d, 1H), 4.0 (s, 2H). ES-MS m/z 211 (MH$^+$).

A suspension of 25 g of "Rink resin" in a mixture of anhydrous DMF (120 mL) and piperidine (30 g) was stirred at rt for 2 h. The deprotected resin was washed sequentially with DMF, dichloromethane, methanol and DMF. The resulting resin was suspended in of DMF (150 mL) and treated with Compound 2e (4.41 g, 0.021 mole) followed with HOBT (3.54 g, 0.026 mole) and DCC (5.36 g, 0.026 mole). The mixture was stirred at rt for 24 hrs and the resin filtered and washed with DMF. The resin was suspended in fresh DMF (150 mL) then treated again with Compound 2e (1.0 g, 0.0048 mole), HOBT (0.88 g, 0.0066 mole) and DCC (1.34 g, 0.0065 mole) and stirred at rt over night under argon. The resulting resin was washed as before to produce the Resin 2f (26.3 g). ES-MS m/Z 210 (MH$^+$) of TFA cleaved sample.

A suspension of Resin 2f (13 g) in DMF (100 mL) was treated with epichlorohydrin (6.0 g, 0.065 mole) and cesium carbonate (4.23 g, 0.046 mole) and stirred under argon at 70° C. for 4 h, then at rt over night. The reaction mixture was filtered and the crude resin washed sequentially with DMF, water, methanol, dichloromethane and ether to give Resin 2g (12.7 g). ES-MS m/z 266 (MH$^+$) of the TFA cleaved sample.

A suspension of Resin 2g (2.0 g) in a 3:1 mixture of ethanol and THF (12 mL) was treated with a 2N solution of dimethylamine (4 mL) in THF and stirred at 50° C. under argon for 1.5 h, then stirred over night at rt. The resulting resin was washed successively with methanol, dichloromethane and ether to produce 2.2 g of resin. The resin was stirred at rt for 1.5 h in a 3:7:0.5 mixture of TFA, dichloromethane and anisole (20 mL). The cleaved resin was filtered and washed with a 30% TFA solution in dichloromethane. The combined filtrates were concentrated in vacuo and the residue triturated with ether to give crude Compound 2h (400 mg) as a hygroscopic solid. ES-MS m/z 311 (MH$^+$).

Compound 2h (400 mg. ca. 0.9 mmol) and Compound 2c (418 mg, 1.35 mmol) were combined in anhydrous THF (3 mL) and the mixture was stirred under argon and cooled in an ice bath while treating dropwise with 5 mL of 1N potassium t-butoxide in THF. The mixture was stirred an additional 5 min in an ice bath, then at rt for three h. The mixture was diluted with ethyl acetate (100 mL) and washed with 10% sodium carbonate solution (30 mL) followed by a brine wash and drying over anhydrous sodium sulfate. The dried solution was filtered and concentrated in vacuo to give the crude product as a bright orange glass. Purification by flash column chromatography on silica (eluting with a 92:7:1 mixture of DCM:methanol:ammonium hydroxide) gave Compound 4 (110 mg, 25%) as an orange solid. $^1$H NMR (CDCl$_3$) δ 8.35 (s, 1H), 7.8 (s, 1H), 7.6–7.1 (m, 6H), 6.8 (t, 1H), 6.35 (d, 1H), 5.45 (d, 1H), 5.0 (d, 1H), 4.3 (m, 3H), 3.7 (m, 1H). 2.4–2.05 (m, 8H). ES-MS m/z 490 (MH$^+$).

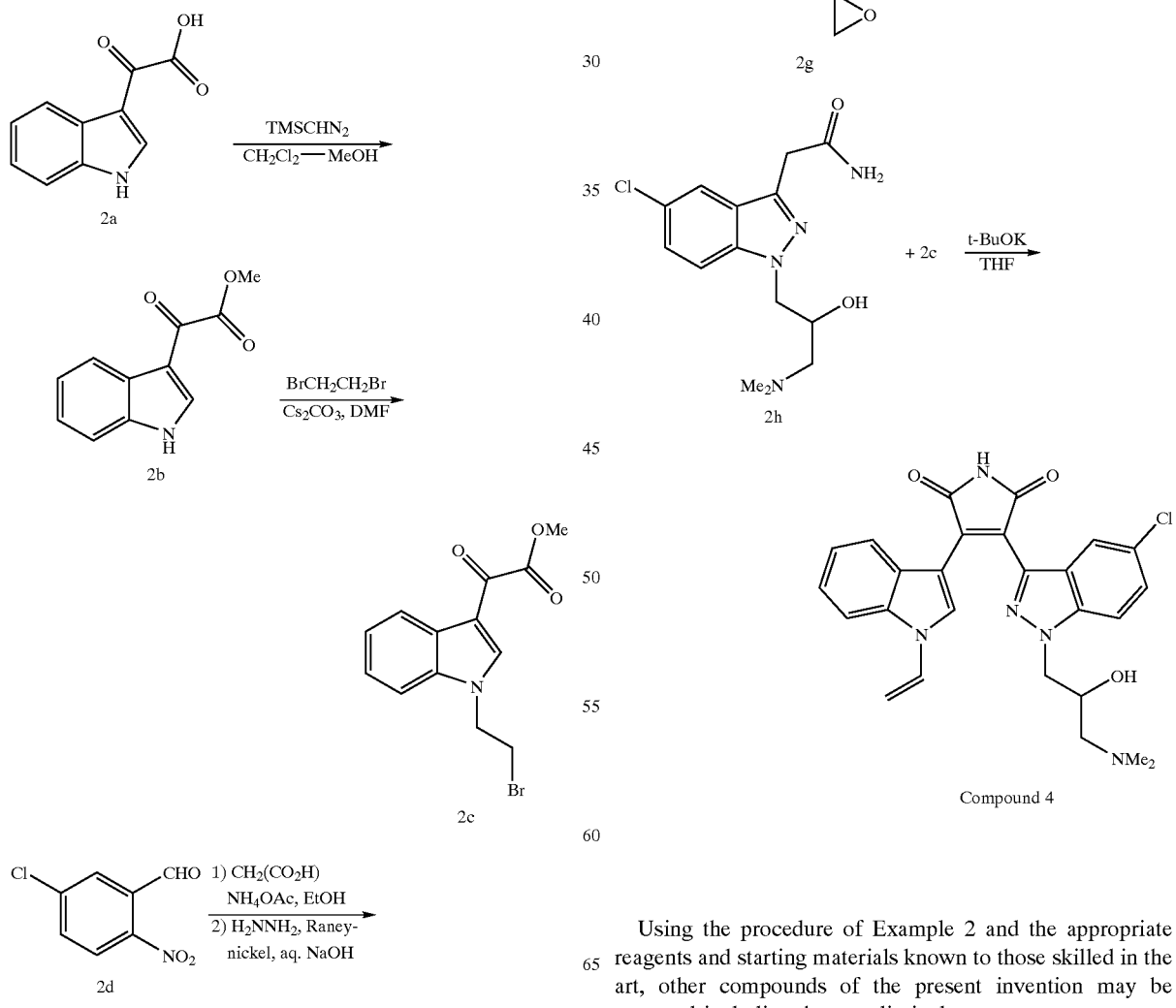

Using the procedure of Example 2 and the appropriate reagents and starting materials known to those skilled in the art, other compounds of the present invention may be prepared including, but not limited to:

| Cpd | Name | ES-MS m/z (MH+) |
|---|---|---|
| 1 | 3-[1-[3-(dimethylamino)-2-hydroxypropyl]-1H-indazol-3-yl]-4-(1-ethenyl-1H-indol-3-yl)-1H-pyrrole-2,5-dione | 446 |
| 2 | 3-(1-ethenyl-1H-indol-3-yl)-4-[1-[2-hydroxy-3-(methylamino)propyl]-1H-indazol-3-yl]-1H-pyrrole-2,5-dione | 442 |

EXAMPLE 3

3-[5-chloro-1-[3-(dimethylamino)-2-hydroxypropyl]-1H-indazol-3-yl]-4-(1-methyl-1H-indol-3-yl)-1H-pyrrole-2,5-dione (Compound 40)

Compound 2b (406 mg, 0.002 mole), iodomethane (1.4 g, 0.01 mole) and cesium carbonate (1.3 g, 0.004 mole) were combined in anhydrous DMF (5 mL) and stirred at 30° C. for 4 h under an atmosphere of argon. The reaction mixture was then partitioned with ether (300 mL) and water (3×50 mL). The organic layer was dried over anhydrous sodium sulfate and concentrated in vacuo to give Compound 3a (434 mg, 100%) as an oily product that crystallized upon standing. $^1$H NMR (CDCl$_3$) δ 8.45 (m, 1H), 8.35 (s, 1H), 7.35 (m, 2H), 7.25 (m, 1H), 4.0 (s, 3H), 3.9 (s, 3H).

Compound 2h (300 mg, 0.0007 mole) and Compound 3a (230 mg, 0.0011 mole) were combined in anhydrous THF (3 mL). The mixture was cooled in an ice bath and stirred under argon while adding a 1N solution of potassium t-butoxide (4.2 mL) in THF dropwise. The mixture was allowed to warm to rt and stirred for 3 h. The mixture was then diluted with ethyl acetate (150 mL) and washed with a 15% sodium carbonate solution followed by brine. The organic layer was dried over anhydrous sodium sulfate and concentrated in vacuo to give Compound 40 as a Crude product. Compound 40 was purified via flash column chromatography on silica (eluting with a 92:7:1 mixture of dichloromethane:methanol:ammonia) to give Compound 40 (85 mg) as an orange glass. ES-MS m/z 478 (MH+). $^1$H NMR (CDCl$_3$) δ 8.15 (s, 1H), 7.75 (s, 1H), 7.55 (d, 1H), 7.45–7.3 (m, 3H), 7.15 (t, 1H), 6.7 (t, 1H), 6.15 (a, 1H), 4.2 (q, 2H), 3.9 (s, 3H), 3.75 (m, 1H), 2.3–2.2 (m, 2H), 2.15 (s, 3H), 2.1 (t, 2H). Anal. Calc'd for $C_{25}H_{24}ClN_5O_3$: C, 62.83; H, 5.06: N, 14.65. Found: C, 61.45; H, 5.13; N, 14.75.

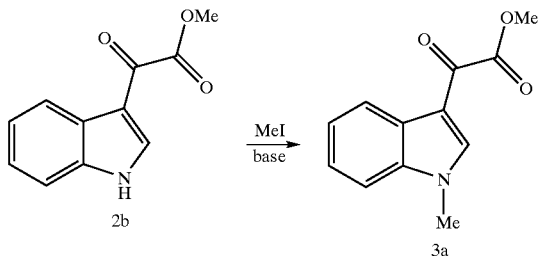

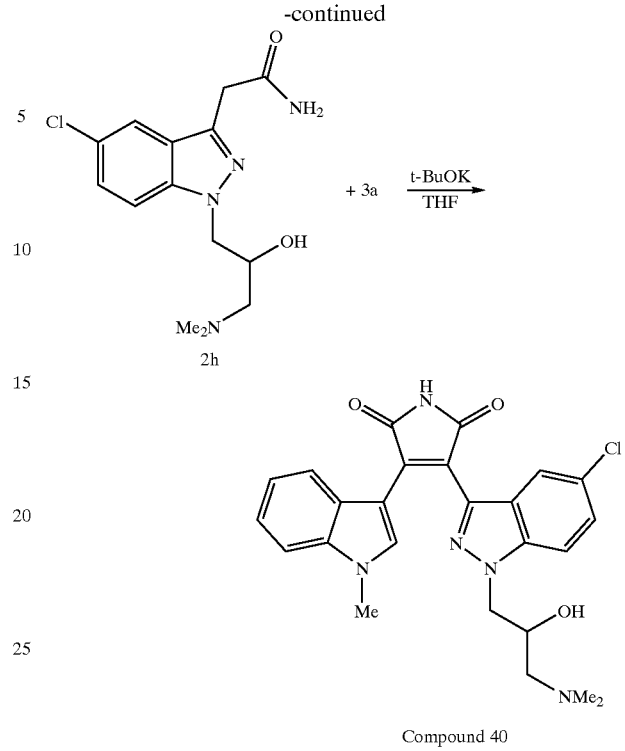

Compound 40

Using the procedure of Example 3 and the appropriate reagents and starting materials known to those skilled in the art, other compounds of the present invention may be prepared including, but not limited to:

| Cpd | Name | ES-MS m/z (MH+) |
|---|---|---|
| 39 | 3-[1-[3-(dimethylamino)-2-hydroxypropyl]-1H-indazol-3-yl]-4-(1H-indol-3-yl)-1H-pyrrole-2,5-dione | 430 |
| 41 | 3-[1-[3-(dimethylamino)-2-hydroxypropyl]-1H-indazol-3-yl]-4-(1-methyl-1H-indol-3-yl)-1H-pyrrole-2,5-dione | 444 |

EXAMPLE 4

3-(5-chloro-1-ethenyl-1H-indol-3-yl)-4-[1-[3-(dimethylamino)propyl]-1H-indazol-3-yl]-1H-pyrrole-2,5-dione (Compound 6)

3-(5-chloro-1-ethenyl-1H-indol-3-yl)-4-[2-[2-(dimethylamino)ethyl]-2H-indazol-3-10 yl]-1H-pyrrole-2,5-dione (Compound 29)

A 5-chloroindole Compound 4a (7.7 g, 0.057 mole) in ether (80 mL) was cooled in an ice bath and treated dropwise with oxalyl chloride (6.5 g, 0.051 mole) while stirring under argon. The resulting yellow slurry was stirred at 5° C. for 30 min, then cooled to −65° C. Sodium methoxide (5.5 gm, 0.1 mole) in anhydrous methanol (50 mL) was added dropwise to the cold mixture over a 30 min period. The mixture was allowed to warm to rt and was then quenched by dropwise addition of water (25 mL). The mixture was stirred for 5 min and the resulting crude light yellow solid was filtered and washed with water. The solid was suspended in ether (200 mL), then filtered and washed with ether to yield Compound 4b (8.0 g, 68%) as a light yellow solid. $^1$H NMR (DMSO-d$_6$) δ 8.55 (d, 1H), 8.15 (s, 1H), 7.55 (d, 1H), 7.3 (d, 1H), 3.9 (s, 3H).

A mixture of Compound 4b (2.37 g, 0.01 mole) and 1,2-dibromoethane (9.4 g, 0.05 mole) in anhydrous DMF (25 mL) was stirred at rt under argon and treated with cesium carbonate (6.5 g, 0.02 mole). The mixture was heated to 30° C. for 4 h then stirred over night at rt. The white solids were filtered and partitioned between ether (300 mL) and water (3×100 mL), then a brine solution (50 mL). The organic layer was dried over anhydrous sodium carbonate and concentrated in vacuo to give a crude yellow oil. The crude oil was triturated with hexane to produce a crude solid. The solid was then flash chromatographed on silica with 1:1 ethyl acetate:hexane to give Compound 4c (1.9 g, 56%) as a light yellow solid. $^1$H NMR (DMSO-d$_6$) δ 8.65 (s, 1H), 8.2 (s, 1H), 7.8(d, 1H), 7.35 (d, 1H), 4.8 (t. 2H), 3.95 (t, 2H), 3.9 (s, 3H).

A mixture of Compound 1e (prepared in Example 1) (0.86 g, 0.0049 mole), potassium carbonate (4.1 g, 0.029 mole) and N,N-dimethyl-3-chloropropylamine hydrochloride (3.87 g, 0.0245 mole) in anhydrous DMF (25 mL) was warmed to 70° C. and stirred under argon for 4 h. After stirring over night at rt, the mixture was diluted with brine (50 mL) and extracted with ethyl acetate (3×150 mL). The organic layer was dried over anhydrous sodium sulfate and concentrated in vacuo to give a tan solid Compound 4d (400 mg, 32%) as a 9:1 mixture of two isomeric products. Evaluation of the $^1$H NMR of the mixture concluded that the N-1 substituted isomer was the major component. Major component: $^1$H NMR (DMSO-d$_6$) δ 7.9–7.1 (m, 6H), 4.45 (t, 2H), 3.75 (s, 2H), 3.1 (m, 2H), 2.75 (m, 6H), 2.18 (m, 2H); ES-MS m/z 261 (MH$^+$). Minor component: $^1$H NMR (DMSO-d$_6$) δ 7.9–7.1 (m, 6H), 4.49 (t, 2H), 4.05 (s, 2H), 3.3 (m, 2H), 3.1 (s, 6H), 2.0–2.3 (m, 2H); ES-MS m/z 261 (MH$^+$).

Compound 4d (208 mg, 0.0008 mole) and Compound 4c (413 mg, 0.0012 mole) were combined in anhydrous THF (3 mL) and the mixture was stirred under argon while cooling in an ice bath. The mixture was then treated dropwise with a 1N solution of potassium t-butoxide in THF (4.8 mL) over a 5 min period. The mixture was allowed to warm to rt and stirring continued another 5 h. The dark reaction mixture was then diluted with ethyl acetate (100 mL) and washed with a 10% sodium carbonate solution (10 mL) followed by brine (2×10 mL). The organic layer was dried over anhydrous sodium sulfate, filtered and concentrated in vacuo to give a crude product (380 mg) containing two major components. Minor impurities were removed by flash column chromatography on silica (eluting with a 9:1 mixture of dichloromethane:methanol) to give of a 9:1 mixture of Compound 6 and Compound 29, respectively (200 mg, 53%). Separation of a 40 mg sample of the isomeric indazoles was accomplished by thick layer (200μ) plate chromatography on silica eluted with an 85:13:2 mixture of chloroform:methanol:ammonia to give Compound 6 (22 mg) and Compound 29 (5 mg). For Compound 6: $^1$H MNR (CDCl$_3$) δ 8.35 (s, 1H), 7.75 (d, 1H), 7.65 (d, 1H), 7.6–7.05 (m, 5H), 6.25 (s, 1H), 5,45 (d, 1H), 5.05 (d, 1H), 4.4 (t, 2H), 2.25 (t, 2H), 2.20 (s, 6H), 1.85 (t, 2H); ES-MS m/z 474 (MH$^+$). For Compound 29: $^1$H NMR (CDCl$_3$) δ 8.15 (s, 1H), 7.7 (d, 1H), 7.3–6.8 (m, 6H), 5.8 (s, 1H), 5.3 (d, 1H), 4.9 (d, 1H), 4.65–4.2 (m, 2H), 2.6–2.2 (m, 8H), 1.9 (t, 2H); ES-MS m/z 474 (MH$^+$).

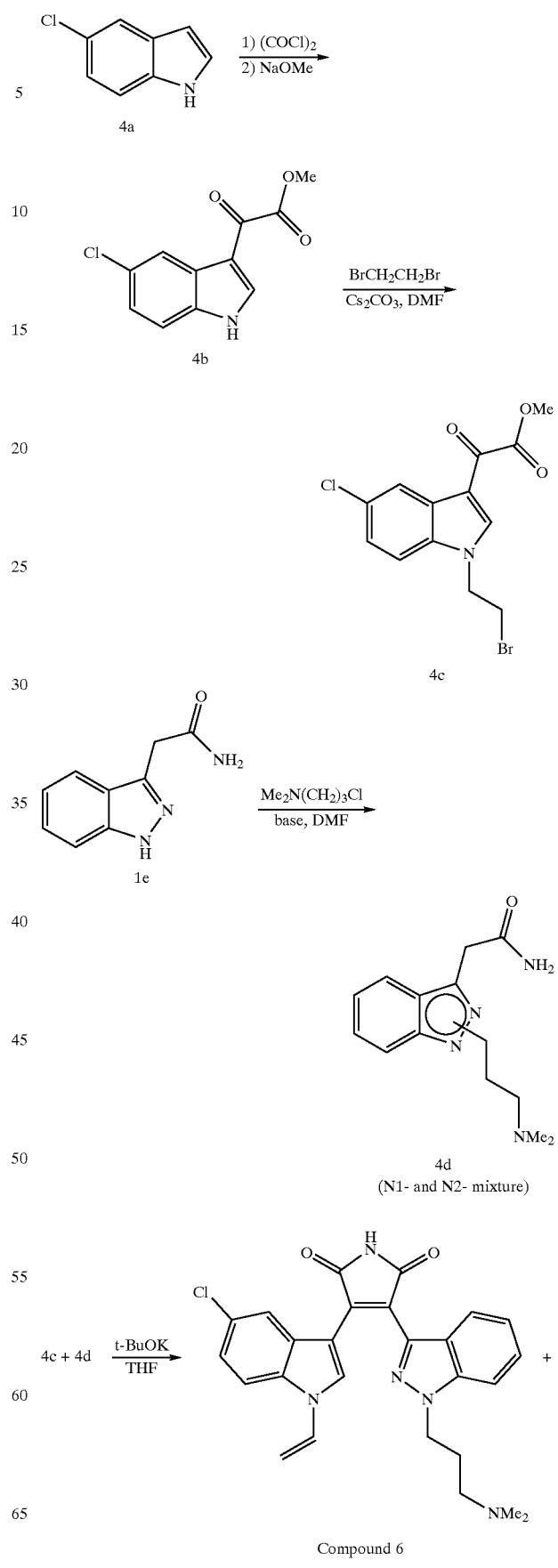

-continued

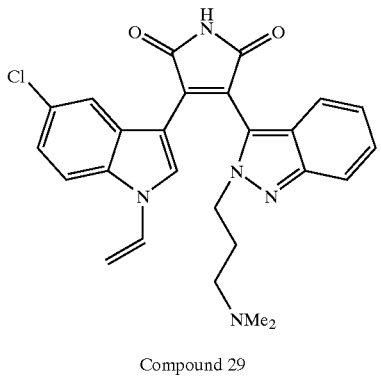

Compound 29

Using the procedure of Example 4 and the appropriate reagents and starting materials known to those skilled in the art, other compounds of the present invention may be prepared including, but not limited to:

| Cpd | Name | ES-MS m/z (MH+) |
|---|---|---|
| 3 | 3-[1-[3-(dimethylamino)propyl]-1H-indazol-3-yl]-4-(1-ethenyl-1H-indol-3-yl)-1H-pyrrole-2,5-dione | 440 |
| 5 | 3-[5-chloro-1-[3-(dimethylamino)propyl]-1H-indazol-3-yl]-4-(1-ethenyl-1H-indol-3-yl)-1H-pyrrole-2,5-dione | 474 |
| 28 | 3-[2-[2-(dimethylamino)ethyl]-2H-indazol-3-yl]-4-(1-ethenyl-1H-indol-3-yl)-1H-pyrrole-2,5-dione | 440 |
| 120 | 3-(5-chloro-2-ethyl-2H-indazol-3-yl)-4-[1-[3-(4-morpholinyl)propyl]-1H-indol-3-yl]-1H-pyrrole-2,5-dione | 518 |
| 121 | 3-[2-(3-hydroxypropyl)-2H-indazol-3-yl]-4-[1-(3-pyridinyl)-1H-indol-3-yl]-1H-pyrrole-2,5-dione | 464 |
| 122 | 3-[2-[2-(dimethylamino)ethyl]-2H-indazol-3-yl]-4-[1-(2-naphthalenyl)-1H-indol-3-yl]-1H-pyrrole-2,5-dione | 526 |
| 123 | 3-(1-benzo[b]thien-3-yl-1H-indol-3-yl)-4-[2-[2-(dimethylamino)ethyl]-2H-indazol-3-yl]-1H-pyrrole-2,5-dione | 532 |
| 124 | 3-(5-chloro-1-methyl-1H-indol-3-yl)-4-[2-(3-hydroxypropyl)-2H-indazol-3-yl]-1H-pyrrole-2,5-dione | 435 |

EXAMPLE 5

3-[1-[3-(dimethylamino)propyl]-1H-indazol-3-yl]4-(1-methyl-1H-indol-3-yl)-1H-pyrrole-2,5-dione (Compound 42)

3-[2-[3-(dimethylamino)propyl]-2H-indazol-3-yl]4-(1-methyl-1H-indol-3-yl)-1H-pyrrole-2,5-dione (Compound 56)

Over a 10 min period, a 1.0 N solution of potassium t-butoxide in THF (2.2 mL, 2.2 mmol) was added dropwise to a suspension of Compound 3a (135 mg, 0.63 mmol) and Compound 4d (115 mg, 0.44 mmol) in anhydrous THF (1 mL) cooled to 0° C. The mixture was stirred at 0° C. for 10 min and rt for 3 h. The resulting dark reaction mixture was then diluted with ethyl acetate 50 mL of and washed with water and brine, then dried over Na$_2$SO$_4$ and concentrated in vacuo. The residue was separated by prep. TLC (CH$_2$Cl$_2$:MeOH:NH$_4$OH; 85:13:2) to afford two isomers. Compound 42 (110 mg, 58% yield) and Compound 56 (8 mg, 4% yield). Compound 42 was dissolved in MeOH and 1.0 N HCl in Et$_2$O was added. The volatiles were evaporated in vacuo to give the HCl salt of Compound 42 (120 mg) as a red-orange solid. For Compound 42: $^1$H NMR (CD$_3$OD) δ 8.10 (s, 1H), 7.62 (d, J=8.6 Hz, 1H), 7.41–7.34 (m, 2H), 7.27 (d, J=8.3 Hz, 1H), 7.07 (t, J=7.3, 7.9 Hz, 1H), 6.92 (t, J=7.3, 7.8 Hz, 1H), 6.58 (t, J=7.6 Hz, 1H), 6.23 (d, J=8.1 Hz, 1H), 4.59 (t, J=5.8 Hz, 2H), 3.91 (s, 3H), 3.19 (t, J=6.9 Hz, 2H), 2.80 (s, 6H), 2.29 (m, 2H); ES-MS m/z 428 (MH$^+$). Anal. calcd. for C$_{25}$H$_{25}$NO$_2$.1.25HCl.1.10H$_2$O: C, 60.92; H, 5.82; N, 14.21; Cl, 8.99; KF, 4.02. Found: C, 61.13; H, 5.70; N, 14.16; Cl, 9.15; KF, 3.92. For Compound 56 (free base): $^1$H NMR (CD$_3$OD) δ 8.29 (s, 1H), 7.63 (d, J=8.2 Hz, 1H), 7.44–7.30 (m, 3H), 7.08–7.00 (m, 2H), 6.54 (t, J=7.8 Hz, 1H), 5.81 (d, J=7.5 Hz, 1H), 4.17 (m, 1H), 4.08 (m, 1H), 3.90 (s, 3H), 2.20 (m, 3H), 2.13 (s, 6H), 1.89 (m, 1H); ES-MS m/z428 (MH$^+$).

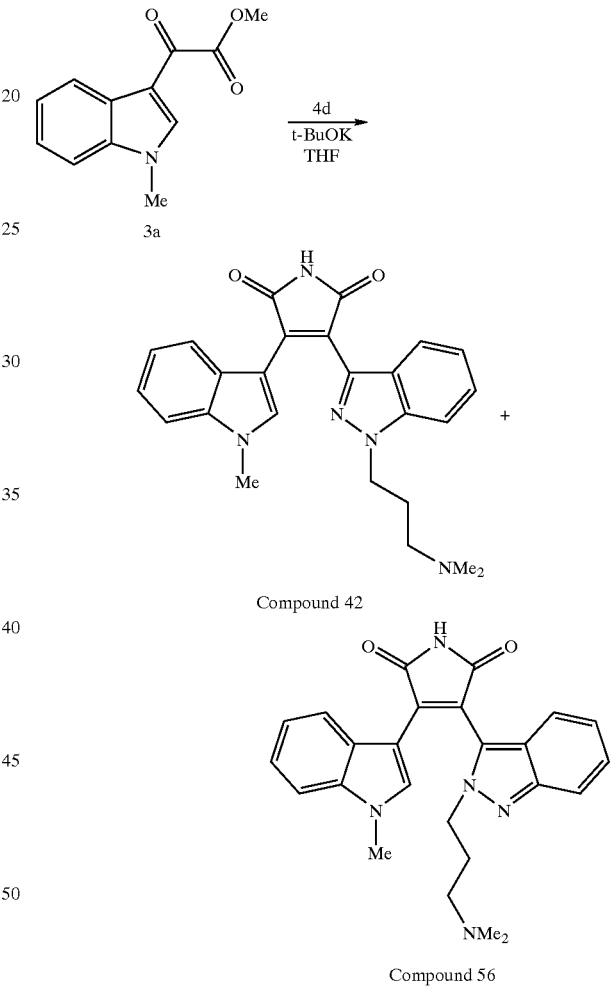

Compound 42

Compound 56

EXAMPLE 6

3-[1-[3-(dimethylamino)propyl]-1H-indazol-3-yl]-4-[1-(3-pyridinylmethyl)-1H-indol-3-yl]-1H-pyrrole-2,5-dione (Compound 26)

Compound 2b (203 2 mg, 0.001 mole) and cesium carbonate (1.3 g, 0.004 mole) were combined in anhydrous DMF (5 mL). The mixture was stirred under argon at 30° C. for 1 h, then 3-bromomethyl pyridine hydrobromide (379 mg, 0.0015 mole) was added. The reaction mixture was stirred for an additional 6 h and was then diluted with of ether (200 mL) and washed with brine (2×50 mL). The organic layer was separated, then dried over anhydrous sodium sulfate and concentrated in vacuo to give Compound 6a (275 mg, 94%) as a brown oil. $^1$H NMR (CDCl$_3$) δ 8.6 (m, 2H): 8.45 (m, 2H), 7.5–7.25 (m, 5H), 5.4 (s, 2H), 3.95 (s, 3H). ES-MS m/z 295 (MH$^+$).

Compound 6a (275 mg 0.0009 mole) and Compound 1f (162 mg, 0.006 mole) were combined in anhydrous THF (10 mL). The mixture was stirred under argon and cooled in an ice bath while 1N potassium t-butoxide in THF (3.6 mL) was added dropwise. The mixture was stirred an additional 5 min in an ice bath, then at rt over night. The dark mixture was then concentrated in vacuo and flash chromatographed on silica (using a 85:13:2 mixture of dichloromethane:methanol:ammonium hydroxide) to yield Compound 26 (104 mg, 355%) as an orange solid. Compound 26 was dissolved in water (5 mL) and adjusted to pH~2 with 1N hydrochloric acid solution. The solution was freeze-dried overnight to give the hydrochloride salt. $^1$H NMR (DMSO-d$_6$) δ 8.8 (m, 2H), 8.4 (s, 1H), 8.1 (d, 1H), 7.85 (m, 1H), 7.75 (d, 1H), 7.6–7.35 (m, 3H), 7.2 (m, 2H), 6.75 (t, 1H), 6.3 (d, 1H), 5.75 (s, 2H), 4.45 (t, 2H), 3.0 (m, 2H), 2.65 (s, 6H), 2.05 (m, 2H). ES-MS m/z 505 (MH$^+$).

Using the procedure of Example 6 and the appropriate reagents and starting materials known to those skilled in the art, other compounds of the present invention may be prepared including, but not limited to:

| Cpd | Name | ES-MS m/z (MH$^+$) |
|---|---|---|
| 7 | 3-[1-[3-(dimethylamino)propyl]-1H-indazol-3-yl]-4-[1-(2-propenyl)-1H-indol-3-yl]-1H-pyrrole-2,5-dione | 454 |
| 66 | 3-[1-[3-(dimethylamino)propyl]-1H-indazol-3-yl]-4-[1-(1-naphthalenylmethyl)-1H-indol-3-yl]-1H-pyrrole-2,5-dione | 554 |
| 67 | 3-[1-[3-(dimethylamino)propyl]-1H-indazol-3-yl]-4-[1-(2-quinolinylmethyl)-1H-indol-3-yl]-1H-pyrrole-2,5-dione | 555 |
| 71 | 3-[1-[(2,6-dichlorophenyl)methyl]-1H-indol-3-yl]-4-[1-[3-(dimethylamino)propyl]-1H-indazol-3-yl]-1H-pyrrole-2,5-dione | 572 |
| 73 | 3-[1-[(5-chlorobenzo[b]thien-3-yl)methyl]-1H-indol-3-yl]-4-[1-[3-(dimethylamino)propyl]-1H-indazol-3-yl]-1H-pyrrole-2,5-dione | 594 |

EXAMPLE 7

3-chloro-1-ethyl-1H-indol-3-yl)-4-[1-[3-(dimethylamino)propyl]-1H-indazol-3-yl]-1H-pyrrole-2,5-dione (Compound 46)

Compound 4b (119.2 mg, 0.0005 mole) and cesium carbonate (326 mg, 0.001 mole) were combined in anhydrous DMF (5 mL) and the mixture was stirred at 30° C. under argon for 1 h. Iodoethane was then added dropwise and stirring continued at 30° C. to rt over night. The reaction mixture was then diluted with ether (100 mL) and partitioned with water (25 mL). The organic layer was separated and the aqueous layer extracted with ether (50 mL). The combined organic layers were washed with brine, then dried over anhydrous sodium sulfate and concentrated in vacuo to give Compound 7a (110 mg, 81%) as a white solid.

Compound 1f (prepared in Example 1) (110 mg, 0.0004 mole) and Compound 7a (70 mg, 0.00027 mole) were combined in anhydrous THF (3 mL) and the mixture was stirred in an ice bath under argon. A 1N solution of potassium t-butoxide in THF (1.6 mL, 0.0016 mole) was added dropwise while stirring under argon. The mixture was stirred an additional 3 h at rt and then evaporated in vacuo at rt to give the crude product. The crude product was purified via thick layer (2000μ) chromatography on silica (eluted with dichloromethane:2% methanol) to give Compound 46 (18 mg) as an orange glass. ES-MS m/z 476 (MH$^+$). $^1$H NMR (CDCl$_3$) δ 8.15 (s, 1H), 7.35 (d, 1H), 7.55 (d, 1H), 7.35 (t, 1H), 7.25 (d, 1H), 7.15 (t, 1H), 7.05 (d, 1H), 6.15 (s, 1H), 4.4 (t, 2H), 4.15 (q, 2H), 2.25 (q, 2H), 2.2 (s, 6H), 1.95 (m, 2H), 1.5 (t, 3H).

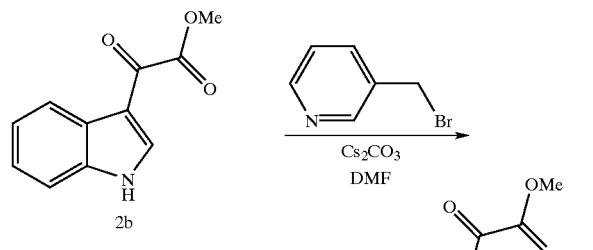

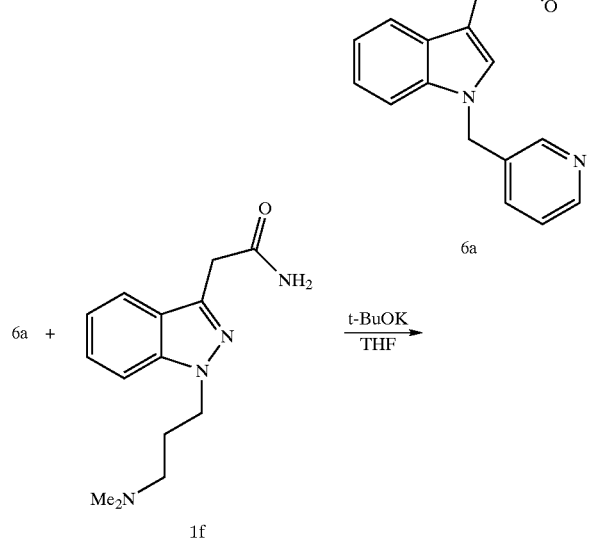

Compound 26

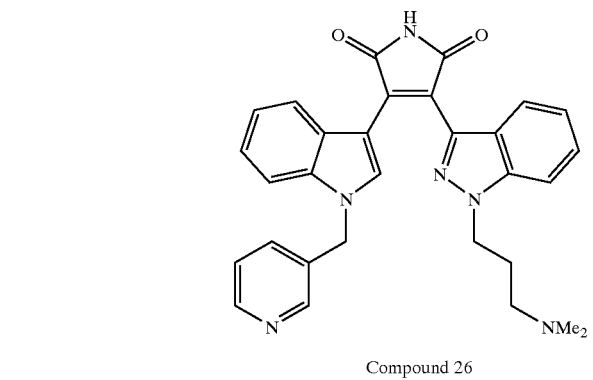

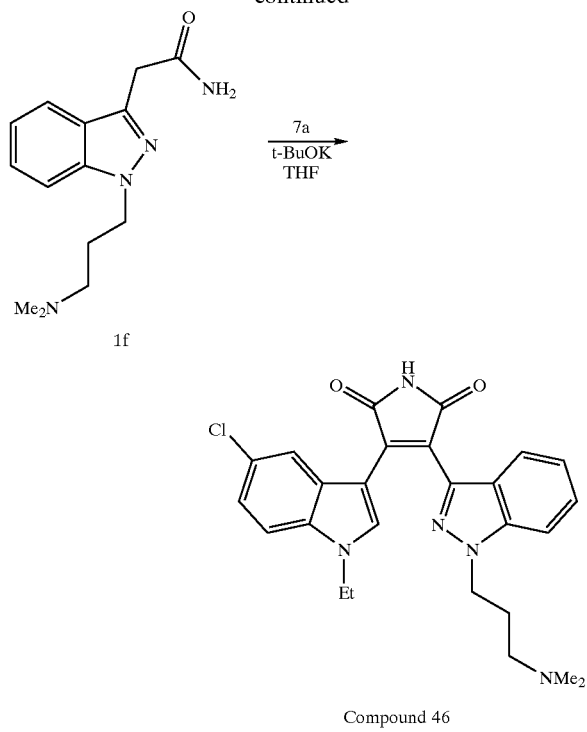

Using the procedure of Example 7 and the appropriate reagents and starting materials known to those skilled in the art, other compounds of the present invention may be prepared including, but not limited to:

| Cpd | Name | ES-MS m/z (MH+) |
|---|---|---|
| 43 | 3-(5-chloro-1-methyl-1H-indol-3-yl)-4-[1-[3-(dimethylamino)propyl]-1H-indazol-3-yl]-1H-pyrrole-2,5-dione | 462 |
| 44 | 3-[1-[3-(dimethylamino)propyl]-1H-indazol-3-yl]-4-(1-ethyl-1H-indol-3-yl)-1H-pyrrole-2,5-dione | 442 |
| 47 | 3-(5-chloro-1H-indol-3-yl)-4-[1-[3-(dimethylamino)propyl]-1H-indazol-3-yl]-1H-pyrrole-2,5-dione | 448 |
| 49 | 3-(4-chloro-1H-indol-3-yl)-4-[1-[3-(dimethylamino)propyl]-1H-indazol-3-yl]-1H-pyrrole-2,5-dione | 448 |
| 50 | 3-[5-chloro-1-(1-methylethyl)-1H-indol-3-yl]-4-[1-[3-(dimethylamino)propyl]-1H-indazol-3-yl]-1H-pyrrole-2,5-dione | 490 |
| 52 | 3-[1-[3-(dimethylamino)propyl]-1H-indazol-3-yl]-4-[1-(2-hydroxyethyl)-1H-indol-3-yl]-1H-pyrrole-2,5-dione | 458 |
| 55 | 3-[1-[3-(dimethylamino)propyl]-1H-indazol-3-yl]-4-(1H-indol-3-yl)-1H-pyrrole-2,5-dione | 414 |
| 69 | 3-(1-ethyl-1H-indol-3-yl)-4-[1-[3-(4-morpholinyl)propyl]-1H-indazol-3-yl]-1H-pyrrole-2,5-dione | 518 |
| 83 | 3-[1-[2-[2-(methylamino)ethoxy]ethyl]-1H-indazol-3-yl]-4-[1-[2-[2-(methylamino)ethoxy]ethyl]-1H-indol-3-yl]-1H-pyrrole-2,5-dione | 531 |

EXAMPLE 8
3-(5-chloro-1-phenyl-1H-indol-3-yl)-4-[1-[3-(dimethylamino)propyl]-1H-indazol-3-yl]-1H-pyrrole-2,5-dione (Compound 48)

The indole Compound 4a (see Example 4) (3.02 g, 20 mmol) and bromobenzene (3.14 g, 20 mmol) were dissolved in DMF (10 mL). Potassium carbonate (2.76 g, 20 mmol) and CuO (130 mg, 1.6 mmol) were added and the reaction was refluxed under argon for 16 h. The reaction was cooled to rt and partitioned between DCM (100 mL) and water (100 mL). The organic layer was washed with water (3×50 mL) and brine (2×50 mL), then dried ($Na_2SO_4$) and evaporated in vacuo to a brown oil. The oil was purified via flash column chromatography (ethyl acetate:hexane; 1:10) to give Compound 8a (2.56 g, 56%) as a colorless oil.

Oxalyl chloride (0.52 g, 4.1 mmol) was added to the indole Compound 821 (0.91 g, 4.0 mmol) in diethyl ether (8 mL) while the mixture was cooled in an ice bath. The mixture was then stirred at ambient temperature for 16 h, then cooled to −65° C. Sodium methoxide (0.46 g, 8.0 mmol) in methanol 10 mL) was added slowly and the reaction was allowed to come to rt. Water (5 mL) was added and the mixture was stirred for 30 min, then a light yellow solid Compound 8b (1.04 g, 83%) was filtered. $^1H$ NMR ($CDCl_3$) δ 8.60 (s, 1H), 8.55 (s, 1H), 7.65–7.25 (m, 7H), 3.98 (s, 3H).

The ester Compound 8b (56 mg, 0.18 mmol) and amide Compound 1f (40 mg, 0.15 mmol, prepared in Example 1) were combined in dry THF (4 mL) under argon and cooled in an ice bath as 1M potassium t-butoxide in THF (0.60 mL, 0.60 mmol) was added with stirring over a 2 min period. After stirring for 2 h at rt, the reaction was quenched by slow addition of 12 M HCl (0.25 mL, 3 mmol), stirred for 15 min and then partitioned between chloroform and saturated $NaHCO_3$. The organic solution was washed with saturated $NaHCO_3$ and brine, then dried ($Na_2SO_4$) and evaporated in vacuo to a flaky solid. The solid was then purified by preparative thin layer chromatography (EtOAc:MeOH:$NH_4OH$; 80:16:2) to afford Compound 48 (26 mg, 33%) as a flaky yellow solid. $^1H$ NMR ($CDCl_3$) δ 8.3 (s, 1H), 7.75 (d, J=7 Hz, 1H), 7.60–7.30 (m, 8H), 7.20 (m, 1H), 7.08 (d, J=7 Hz, 1H), 6.28 (s, 1H), 4.43 (m, 2H), 2.37 (m, 2H), 2.25 (s, 6H), 2.01 (m, 2H). ES-MS m/z 524 (MH+).

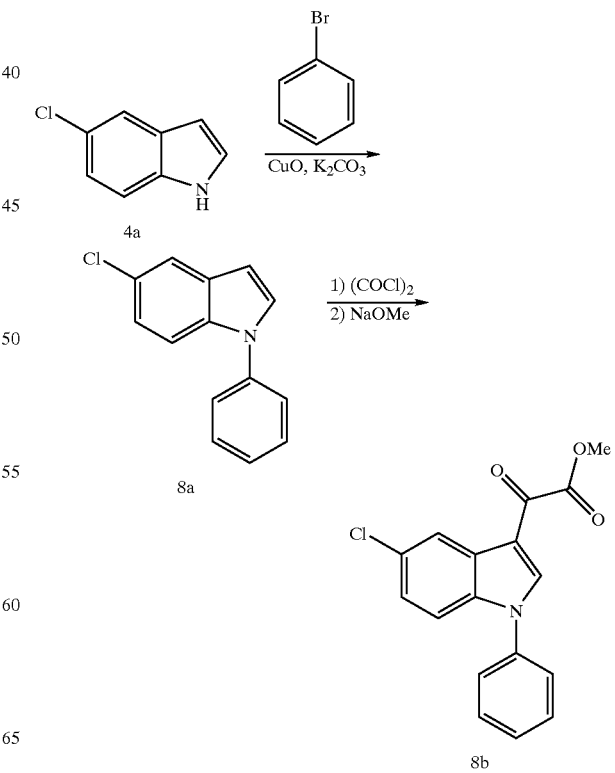

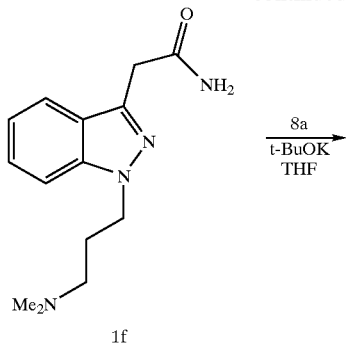

Using the procedure of Example 8 and the appropriate reagents and starting materials known to those skilled in the art, other compounds of the present invention may be prepared including, but not limited to:

| Cpd | Name | ES-MS m/z (MH+) |
|---|---|---|
| 45 | 3-[1-[3-(dimethylamino)propyl]-1H-indazol-3-yl]-4-(1-phenyl-1H-indol-3-yl)-1H-pyrrole-2,5-dione | 490 |
| 53 | 3-[1-[3-(dimethylamino)propyl]-1H-indazol-3-yl]-4-[1-(2-methylphenyl)-1H-indol-3-yl]-1H-pyrrole-2,5-dione | 504 |
| 54 | 3-[1-(3-bromophenyl)-1H-indol-3-yl]-4-[1-[3-(dimethylamino)propyl]-1H-indazol-3-yl]-1H-pyrrole-2,5-dione | 568 |

EXAMPLE 9

3-[1-[3-(dimethylamino)propyl]-1H-indazol-3-yl]-4-[1-(2-propenyl)-1H-indazol-3-yl]-1H-pyrrole-2,5-dione (Compound 30)

3-[1-[3-(dimethylamino)propyl]-1H-indazol-3-yl]-4-(1H-indazol-3-yl)-1H-pyrrole-2,5-dione (Compound 57)

3,4-bis[1-[3-(dimethylamino)propyl]-1H-indazol-3-yl]-1H-pyrrole-2,5-dione (Compound 58)

Iodine (21.3 g, 84.0 mmol) was added to indazole Compound 9a (4.95 g, 42.0 mmol) in DMF (80 mL) followed by KOH (8.84 g, 158 mmol). The reaction mixture was stirred at rt for 1 h and was poured into 10% NaHCO₃ (260 mL), then extracted with Et₂O (2×200 mL). The combined extracts were washed with water (100 mL) and brine (100 mL), then dried (Na₂SO₄) and evaporated in vacuo to give Compound 9b (10.0 g) as a colorless solid. EtMgBr (3.0 M in Et₂O, 6.0 mL, 18.0 mmol) was added dropwise over a period of 10 min to a solution of indazole Compound 9b (1.22 g, 5.0 mmol) in THF (45 mL) cooled to 0° C. The reaction mixture was then stirred at 0° C. for 20 min and a solution of Me₃SnCl (2.4 g, 12.0 mmol) in THF (5 mL) was added dropwise over a 10 min. period. The mixture was stirred at 0° C. for 15 min hten at rt for 10 min. Saturated NH₄Cl (40 mL) was added followed by EtOAc (150 mL) and water (20 mL). The organic layer was separated, washed with water (40 mL) and brine (40 mL), then dried (Na₂SO₄) and evaporated in vacuo to afford Compound 9c (1.35 g) as a light yellow solid.

Compound 9c (1.07 g, 3.8 mmol) was combined with 1-benzyl-3,4-dibromomaleimde Compound 9d (438 mg, 1.27 mmol, prepared as described in G. Xie, et al., *Tetrahedron Lett.*, 1994, 35, 5555) and LiCl (215 mg, 5.08 mmol) in toluene (25 mL) under argon and Pd(PPh₃)₂Cl₂ (178 mg, 0.25 mmol) was added. The reaction mixture was stirred at 90° C. for 20 h and then diluted with EtOAc (150 mL), washed with water (60 mL) and brine (60 mL), then dried (Na₂SO₄) and evaporated. The residue was separated by flash column chromatography (DCM:MeOH; 97:3) to afford Compound 9e (430 mg) as a red-orange solid. ¹H NMR (DMSO) δ 7.55 (d, J=8.1 Hz, 2H), 7.40–7.28 (m, 9H), 6.98 (t, J=7.3 Hz, 2H), 4.84 (s, 2H). ES-MS m/z 420 (MH⁺).

A mixture of Compound 9e (126 mg, 0.30 mmol) and K₂CO₃ (166 mg, 1.20 mmol) in DMF (6 mL) was stirred at rt for 5 min and then 3-dimethylaminopropylchloride hydrochloride (47 mg, 0.30 mmol) was added portionwise. After stirring at 60° C. for 16 h, half of the reaction mixture was transferred to a separate round bottom flask and treated with allyl chloride (17 mg, 0.22 mmol). The resulting mixture was stirred at 60° C. for 4 h, then diluted with EtOAc (60 mL), washed with water (30 mL) and brine (20 mL), then dried (Na₂SO₄) and evaporated in vacuo to give Compound 9f as a mixture of three products. The Compound 9f mixture was dissolved in EtOH (5 mL) and KOH (84 mg, 1.5 mmol) was added. After stirring at 80° C. for 16 h, the reaction mixture was diluted with water (10 mL), acidified with 10% citric acid (10 mL) and extracted with EtOAc (40 mL). The aqueous solution was evaporated in vacuo and the resulting residue was combined with neat NH₄OAc (10 g) and stirred at 140° C. for 1.5 h. The mixture was cooled to rt, dissolved in water (30 mL), made basic with 3N NaOH to pH 10 and extracted with EtOAc (3×50 mL). The combined extracts were washed with water and brine, then dried (Na₂SO₄) and evaporated in vacuo. The residue was separated by preparative TLC (DCM:EtOAc:MeOH:NH₄OH; 3–0:70:20:3) to afford Compound 30 (2.2 mg). Compound 57 (1.0 mg) and Compound 58 (4.5 mg) were also isolated. For Compound 30: yellow-orange solid, ¹H NMR (CDCl₃) δ 7.46 (d, J=8.5 Hz, 1H), 7.38–7.20 (m, 4H), 7.07 (d, J=8.3 Hz, 1H), 6.98–6.88 (m, 2H), 5.93 (m, 1H), 5.21–5.08 (m, 2H), 5.04 (d, J=5.5 Hz, 2H), 4.42 (t, J=6.9 Hz, 2H), 2.15 (s, 6H), 2.13 (m, 2,H), 1.88 (t, J=6.8 Hz, 2H). ES-MS m/z 455 (MH⁺). For Compound 57: yellow-orange solid, ES-MS m/z 415 (MH⁺). For Compound 58: yellow-orange solid, ¹H NMR (CDCl₃) δ 7.46 (d, J=8.6 Hz, 2H), 7.28 (m, 2H), 7.14 (d, J=8.2 Hz, 2H), 6.92 (t, J=8.2 Hz, 2H), 4.45 (t, J=6.8 Hz, 4H), 2.26 (t, J=6.8 Hz, 4H), 2.21 (s, 12H), 1.97 (t, J=6.8 Hz, 4H). ES-MS m/z 500 (MH⁺).

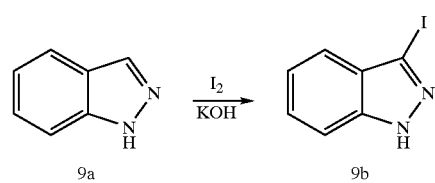
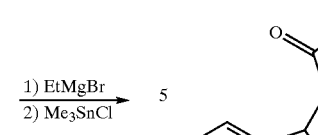
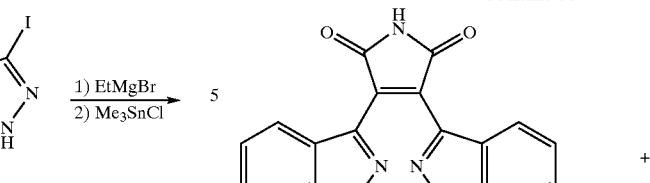
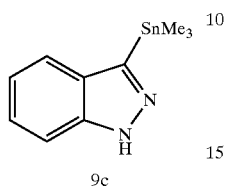
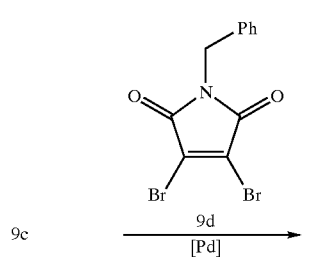
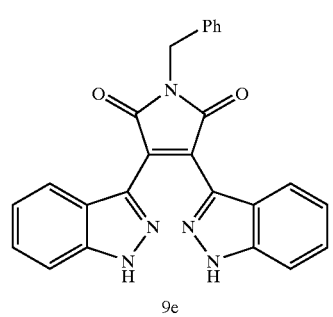
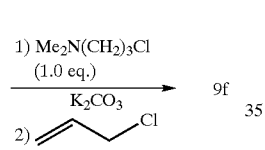
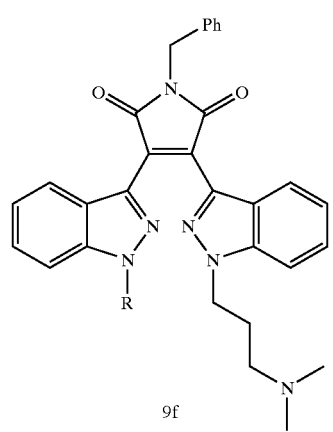
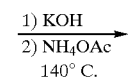
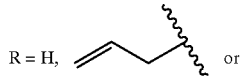
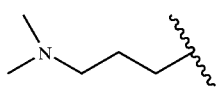

Compound 30, 57 and 58

EXAMPLE 10

3-[1-[3-(dimethylamino)propyl]-1H-indazol-3-yl]-1,5-dihydro-4-[1-(2-thienyl)-1H-indol-3-yl]-2H-pyrrol-2-one (Compound 36)

4-[1-[3-(dimethylamino)propyl]-1H-indazol-3-yl]-1,5-dihydro-3-[1-(2-thienyl)-1H-indol-3-yl]-2H-pyrrol-2-one (Compound 37)

Compound 9 (0.85 g, 1.7 mmol) (prepared using the procedure of Example 12) in THF (75 mL) was cooled in an ice bath as 1M LAH in diethyl ether (10.5 mL, 10.5 mmol) was added over a 5 min period. The reaction mixture was stirred at rt for 6 hr, then cooled in an ice bath as water (25 mL) was cautiously added with vigorous stirring. The solution was made acidic (pH 2.0) with addition of 2N HCl and stirred at rt for 10 min. Saturated sodium bicarbonate was added until the pH was greater than 9.0. The solution was then extracted with ethyl acetate. The organic extract was washed with brine (2×), then dried (K$_2$CO$_3$) and evaporated in vacuo to a yellow solid (0.90 g). The material was purified by flash column chromatography on 200 g of silica gel (eluting with ethyl acetate:methanol:ammonium hydroxide; 80:20:2). The impure faster eluting lactam Compound 36 (200 mg) was collected first, then the slower isomer Compound 37 (80 mg). The first lactam was flash column chromatographed a second time (50 g silica) to afford Compound 36 (60 mg): $^1$H NMR (CDCl$_3$) δ 7.70 (s, 1H), 7.55 (d, J=8 Hz, 1H), 7.40 (d, J=8 Hz, 1H), 7.30–6.75 (m, 9H), 4.67 (s, 2H), 4.45 (m, 2H), 2.25 (m, 2H), 2.20 (s, 6H), 2.05 (m, 2H); ES-MS m/z 482 (MH$^+$). The second lactam was purified by preparative thin layer chromatography (DCM:methanol:ammonium hydroxide; 80:16:1) to afford Compound 37 (25 mg): $^1$H NMR (CDCl$_3$) δ 7.78 (s, 1H), 7.75 (d, J=8 Hz. 1H), 7.50–6.90 (m, 10H), 4.73 (s, 2H), 4.43 (m, 2H), 2.25 (m, 2H), 2.20 (s, 6H), 2.05 (m, 2H); ES-MS m/z 482 (MH$^+$).

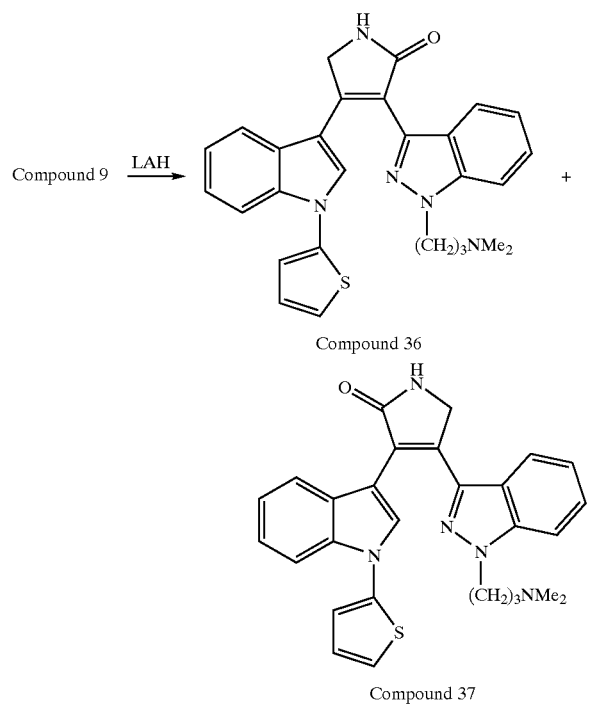

Compound 9 →(LAH) Compound 36 + Compound 37

EXAMPLE 11

3-[1-[3-(dimethylamino)propyl]-1H-indazol-3-yl]-4-[1-(2-naphthalenyl)-1H-indol-3-yl]-1H-pyrrole-2,5-dione (Compound 14)

Following the procedure of Example 1, using 2-bromonaphthalene in place of 3-bromopyridine, a 1-(2-naphthalenyl)-indol-3-yl glyoxylic methyl ester analog of Compound 1c was filtered off as a light yellow solid (1.23 g, 94%). $^1$H NMR (CDCl$_3$) δ 8.68 (s, 1H), 8.55 (d, J=7 Hz, 1H), 8.0 (m, 4H), 7.6 (m, 4H), 7.38 (m, 2H), 3.98 (s, 3H).

The 1-(2-naphthalenyl)-indol-3-yl glyoxylic methyl ester (1.18 g, 3.6 mmol) and amide Compound 1f (0.78 g, 3.0 mmol) were combined in dry THF (20 mL) under argon and cooled with an ice bath as 1M potassium t-butoxide in THF (12 mL, 12 mmol) was added with stirring over an 8 min period. After 1.1 h stirring, the reaction was quenched in an ice bath, 12 N HCl (5.0 mL, 60 mmol) was slowly added over a 3 min period. The mixture was stirred for 15 min and then partitioned between chloroform (125 mL) and saturated NaHCO$_3$. The organic solution was washed with saturated NaHCO$_3$ and brine then dried (Na$_2$SO$_4$) and evaporated in vacuo to a flaky solid. The solid was then purified by flash column chromatography (80:16:2 ethyl acetate:MeOH:NH$_4$OH) to afford Compound 14 (1.32 g, 82%) as an orange flaky solid. Compound 14 was crystallized from ethyl acetate:methanol (10:1, 10 mL) as an orange solid (1.02 g), The solid was then dissolved in DCM (20 mL) containing methanol (5 mL). 1 N HCl in diethyl ether (3.0 mL, 3.0 mmol) was added. The solution was evaporated in vacuo to give Compound 14 (1.31 g) as a red solid. Compound 14 was dissolved in water (100 mL) with slight warming, then frozen and lyophilized to give the hydrochloride salt. $^1$H NMR (DMSO) δ 8.44 (s, 1H), 8.22 (s, 1H), 8.19 (m, 1H), 8.09 (m, 2H), 7.84–7.60 (m, 6H), 7.47 (dd, 1H, J=7.5, 7.6 Hz), 7.18 (dd, 2H, J=7.5, 7.7 Hz), 6.86 (dd, 1H, J=7.5, 7.6 Hz), 6.47 (d, 1H, J=8.3 Hz), 4.49 (t, 2H, J=6.8 Hz), 2.93 (m, 2H), 2.57 (s, 6H), 2.03 (m, 2H). ES-MS m/z 540 (MH$^+$). Anal. Calcd. for C$_{34}$H$_{29}$N$_5$O$_2$.2.0H$_2$O.1.5HCl: C, 64.78; H, 5.51; N, 11.11; KF, 5.71. Found: C, 65.15; H, 5.51; N, 11.29; KF, 6.19.

EXAMPLE 12

3-[1-[3-(dimethylamino)propyl]-1H-indazol-3-yl]-4-[1-(2-thienyl)-1H-indol-3-yl]-1H-pyrrole-2,5-dione (Compound 9)

Following the procedure of Example 1, using 2-bromothiophene in place of 3-bromopyridine, a 1-(2-thienyl)-indol-3-yl glyoxylic methyl ester analog of Compound 1c was prepared. $^1$H NMR (CDCl$_3$) δ 8.55 (s, 1H), 8.47 (m, 1H), 7.55 (m, 1H), 7.40 (m, 2H), 7.33 (dd, J=1.4, 5.5 Hz, 1H), 7.22 (dd, J=1.4, 3.7 Hz, 1H), 7.12 (dd, J=3.7, 5.5 Hz, 1H), 3.97 (s, 3H).

The 1-(2-thienyl)-indol-3-yl glyoxylic methyl ester (787 mg, 2.76 mmol) and amide Compound 1f (600 mg, 2.3 mmol) were combined in dry THF (10 mL) under argon and cooled in an ice bath as 1M potassium t-butoxide in THF (9.2 mL, 9.2 mmol) was added with stirring over a 20 min period. After 1 h, the reaction was quenched in an ice bath, 12 N HCl (3.5 mL, 42 mmol) was slowly added over a 3 min period. The mixture was stirred for an additional 5 min and then partitioned between chloroform:2-propanol (10:1, 200 mL) and saturated NaHCO$_3$. The organic solution was washed with brine, then dried (Na$_2$SO$_4$) and evaporated in vacuo to a flaky solid (1.1 g, 98%). The solid was purified by flash column chromatography (90:9:1; DCM:MeOH:NH$_4$OH) to afford Compound 9 (0.84 g, 69%) as an orange flaky solid. A portion of Compound 9 was dissolved in excess dilute HCl, then frozen and lyophilized to give the hydrochloride salt. $^1$H NMR (DMSO) δ 8.26 (s, 1H), 8.76 (m, 2H), 7.62 (m, 2H), 7.44 (m, 2H), 7.20 (m, 3H), 6.86 (dd, J=7.5, 7.7 Hz, 1H), 6.47 (d, J=8.0 Hz, 1H), 4.45 (dd, J=6.9, 7.0 Hz, 2H), 2.90 (m, 2H), 2.50 (s, 6H), 1.99 (m, 2H). ES-MS m/z 496 (MH$^+$). Anal. Calcd. for C$_{28}$H$_{25}$N$_5$O$_2$S.HCl.1.5H$_2$O (495.6/559.08): C, 60.15; H, 5.22; N, 12.53; H$_2$O, 4.83. Found: C, 59.87; H, 4.96; N, 12.45; H$_2$O, 4.39.

EXAMPLE 13

3-(4-chloro-1-ethenyl-1H-indol-3-yl)-4-[1-[3-(dimethylamino)propyl]-1H-indazol-3-yl]-1H-pyrrole-2,5-dione (Compound 10)

Following the procedure of Example 4, using 4-chloroindole Compound 13a in place of the 5-chloroindole Compound 4a, a mixture of Compound 13a (2.0 g, 0.013 mole) in ether (50 mL) was cooled in an ice bath and treated dropwise with 1.66 g (0.013 mole) of oxalyl chloride while stirring under argon. The resulting yellow slurry was stirred at 5° C. for 30 min then cooled to −65° C. A solution of sodium methoxide (1.42 g, 0.026 mole) in anhydrous methanol (25 mL) was added dropwise to the cold mixture over a 30 min period then the mixture was allowed to warm to rt. The mixture was then quenched by dropwise addition of water (20 mL), stirred for 5 min and the resulting two phase mixture was separated. The water layer was washed with 30 mL of ether. The combined ether extracts were washed with brine and dried over anhydrous potassium carbonate. The solvent was removed in vacuo to give Compound 13b (2.6 g) that gradually crystallized. The crude product was used in the next step without further purification. A mixture of Compound 13b (1.0 g, 0.0042 mole) and 1,2-dibromoethane (3.9 g, 0.021 mole) in anhydrous DMF (20 mL) was stirred at rt under argon and treated with cesium carbonate (2.74 g, 0.0084 mole). The mixture was heated to 50° C. for 4 h then stirred over night at rt. The white solids were filtered and washed with ethyl acetate (150 mL). The filtrate was partitioned with three portions of water then one portion of brine. The organic layer was separated, then dried over anhydrous sodium sulfate and concentrated in vacuo to give a 60/40 mixture of Compound 13c and Compound 13d (162 mg) as a light yellow oil. The oil was used in the next step without further purification.

The ester Compound 13c and Compound 13d (150 mg, as a mixture) and amide Compound 1f (84 mg, 0.0003 mole) were combined in dry THF (5 mL) under argon and cooled in an ice bath as 1M potassium t-butoxide in THF (1.8 mL) was added dropwise with stirring over a 5 min period. The mixture was stirred at rt for 2 h then spotted on a 2000μ silica prep plate and eluted with a 85:13:2 mixture of ethyl acetate:methanol:ammonia. The spot containing the product was scraped and washed free of the silica with a 90:10 mixture of chloroform:methanol. The solvent was removed in vacuo to give Compound 10 as a bright orange solid. ES-MS m/z 474 (MH+).

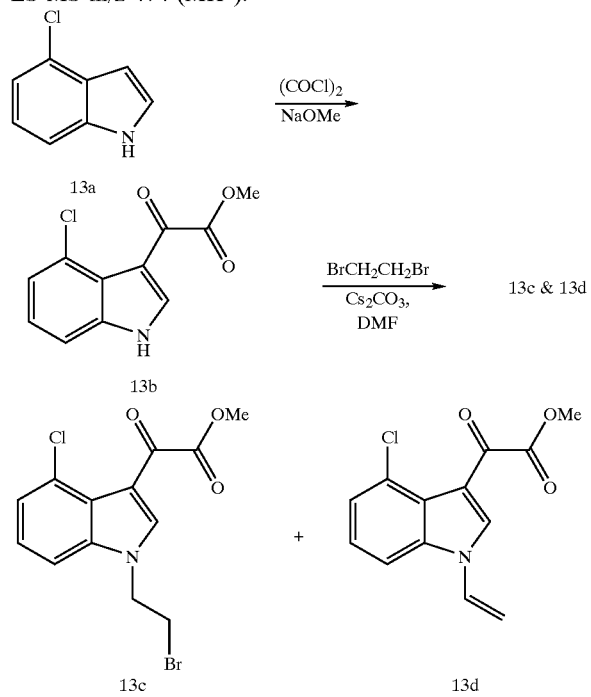

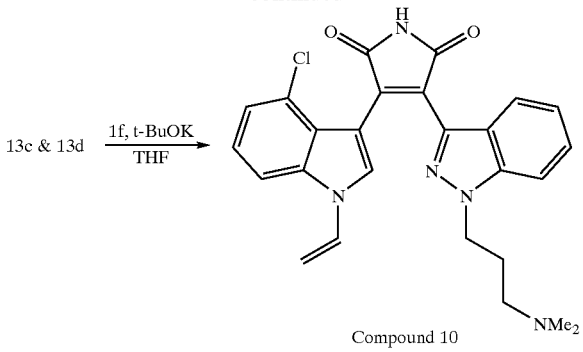

Compound 10

EXAMPLE 14

3-[1-[3-(dimethylamino)propyl]-1H-indazol-3-yl-4-(1-ethyl-5-methyl-1H-indol-3-yl)-1H-pyrrole-2,5-dione (Compound 51)

Following the procedure of Example 4, using 5-methylindole in place of 5-chloroindole, 5-methylindole (2.0 g, 0.0152 mole) in a mixture with ether (50 mL) was cooled in an ice bath and treated dropwise with oxalyl chloride (1.96 g, 0.0154 mole) while stirring under argon. The resulting yellow slurry was stirred at 5° C. For 30 min then cooled to −65° C. A solution of sodium methoxide (1.7 g, 0.031 mole) in anhydrous methanol (25 mL) was added dropwise to the cold mixture over a 30 min period, then the mixture was allowed to warm to rt. The mixture was then cooled in an ice bath, quenched by dropwise addition of water (50 mL) and stirred for 5 min. The resulting three phase mixture was filtered and the solids were washed with water then air dried to give a 5-methylindole methyl ester analog of Compound 4b (2.8 g). The crude product was used in the next step without further purification.

Following the procedure of Example 7, a mixture of the 5-methylindole methyl ester (217 mg, 0.001 mole) and cesium carbonate (650 mg, 0.002 mole) in anhydrous DMF (10 mL) was stirred at 30° C. under argon for 1 h. Iodoethane (780 mg, 0.005 mole) was then added dropwise and stirring continued at 25–30° C. overnight. The reaction mixture was then diluted with ether (150 mL) and partitioned with water (25 mL). The organic layer was separated and the aqueous layer extracted with ether (50 mL). The combined organic layers were washed with brine, then dried over anhydrous sodium sulfate and concentrated in vacuo to give a N-ethyl substituted 5-methylindole methyl ester analog of Compound 7a (233 mg) as a clear oil. The oil was used in the next step without further purification.

A mixture of Compound 1f (see Example 1) (35 mg, 0.13 mmol) and the N-ethyl substituted 5-methylindole methyl ester (50 mg, 0.2 mmol) in anhydrous THF (5 mL) was stirred in an ice bath under argon. Then a 1N solution of potassium t-butoxide in THF (0.8 mL, 0.0008 mole) was added dropwise while stirring under argon. The mixture was stirred for an additional 3 h at rt and then evaporated in vacuo at rt to give the crude product. The crude product was purified via preparative TLC, eluted with an 85:13:2 mixture of dichloromethane:methanol:ammonia to give of Compound 51 (1.5 mg) as an orange glass. ES-MS m/z 456 (MH+).

Using the procedure of Example 14 and the appropriate reagents and starting materials known to those skilled in the art, other compounds of the present invention may be prepared including, but not limited to:

| Cpd | Name | ES-MS m/z (MH+) |
|---|---|---|
| 81 | 3-[1-[3-(dimethylamino)propyl]-1H-indazol-3-yl]-4-(1-ethyl-5-methoxy-1H-indol-3-yl)-1H-pyrrole-2,5-dione | 472 |
| 86 | 3-(5-chloro-1-ethyl-1H-indazol-3-yl)-4-[1-[3-(4-morpholinyl)propyl]-1H-indol-3-yl]-1H-pyrrole-2,5-dione | 518 |
| 87 | 3-(5-chloro-1-ethyl-1H-indazol-3-yl)-4-[1-[3-(4-methyl-1-piperazinyl)propyl]-1H-indol-3-yl]-1H-pyrrole-2,5-dione | 531 |
| 96 | 3-(5-chloro-1-ethyl-1H-indazol-3-yl)-4-[1-[3-(1-pyrrolidinyl)propyl[-1H-indol-3-yl]-1H-pyrrole-2,5-dione | 502 |

EXAMPLE 15

3-[1-[3-(dimethylamino)propyl]-1H-indazol-3-yl]-4-[1-(1-naphthalenyl)-1H-indol-3-yl]-1H-pyrrole-2,5-dione (Compound 15)

Following the procedure of Example 1, using 1-bromonaphthalene in place of 3-bromopyridine, a 1-(1-naphthyl)-indol-3-yl glyoxylic methyl ester analog of Compound 1c was prepared. $^1$H NMR (CDCl$_3$) δ 8.60 (s, 1H), 8.56 (d, J=8.0 Hz, 1H), 8.05 (m, 3H), 7.65 (m, 4H), 7.40–7.20 (m, 2H), 7.01 (m, 1H), 3.97 (s, 3H).

The 1-(1-naphthyl)-indol-3-yl glyoxylic methyl ester (59 mg, 0.18 mmol) and amide Compound 1f (40 mg, 0.15 mmol) were combined in THF (2.0 mL) with 1M potassium t-butoxide in THF (0.60 mL, 0.60 mmol) at 0° C. to afford an orange solid (90 mg). The solid was purified using preparative silica TLC plates (1500μ; EtOAc: MeOH:NH$_4$OH; 40:8:1) to give Compound 15 (37 mg, 46%) as an orange solid. ES-MS m/z 540 (MH+). $^1$H NMR (CDCl$_3$) δ 8.30 (s, 1H), 7.99 (m, 2H), 7.74 (d, J=8.2 Hz, 1H), 7.55 (m, 4H), 7.41 (m, 3H), 7.14 (dd, J=7.4, 7.5 Hz, 1H), 6.95 (m, 2H), 6.79 (dd, J=7.0, 8.0 Hz, 1H), 6.61 (d, J=8.0 Hz, 1H), 4.41 (dd, J=6.9, 7.0 Hz, 2H), 2.15 (m, 2H), 2.12 (s, 6H), 1.88 (m, 2H).

EXAMPLE 16

3-[1-[3-(dimethylamino)propyl]-1H-indazol-3-yl]-4-[1-(4-isoquinolinyl)-1H-indol-3-yl]-1H-pyrrole-2,5-dione (Compound 16)

Following the procedure of Example 1, using 4-bromoisoquinoline in place of 3-bromopyridine, a 1-(4-isoquinolinyl)-indol-3-yl glyoxylic methyl ester analog of Compound 1c was prepared. $^1$H NMR (CDCl$_3$) δ 9.45 (s, 1H), 8.70 (s, 1H), 8.63 (s, 1H), 8.58 (d, J=7.9 Hz, 1H), 8.19 (m, 1H), 7.75 (m, 2H), 7.50 (m, 2H), 7.29 (m, 1H), 7.02 (d, J=8.3 Hz, 1H), 3.96 (s, 3H).

The 1-(4-isoquinolinyl)-indol-3-yl glyoxylic methyl ester (175 mg, 0.53 mmol) and amide Compound 1f (117 mg, 0.45 mmol) were combined in THF (5.0 mL) with 1M potassium t-butoxide in THF (1.80 mL, 1.80 mmol) at 0° C. to afford an orange solid (250 mg). The solid was purified using flash column chromatography (EtOAc:MeOH: NH$_4$OH; 40:4:1) to give Compound 16 (100 mg, 41%) as an orange solid. Compound 16 was dissolved in aqueous HCl, then frozen and lyophilized to the hydrochloride salt (115 mg, 40%). ES-MS m/z 541 (MH+). $^1$H NMR (DMSO) δ 9.60 (s, 1H), 8.95 (s, 1H), 8.40 (d, J=8.0 Hz, 1H), 8.28 (s, 1H), 7.85 (m, 3H), 7.65 (d, J=8.2 Hz, 1H), 7.48 (m, 1H), 7.18 (m, 3H), 7.0 (m, 1H), 6.91 (m, 1H), 6.68 (d, J=8.0 Hz, 1H), 4.52 (m, 2H), 3.0 (m, 2H), 2.61 (s, 6H), 2 10 (m, 2H).

EXAMPLE 17

3-[5-chloro-2-methyl-1-(3-pyridinyl)-1H-indol-3-yl]-4-[1-[3-(dimethylamino)propyl]-1H-indazol-3-yl]-1H-pyrrole-2,5-dione (Compound 20)

Following the procedure of Example 1, using 2-Me-5-Cl-indole (2.00 g, 17.1 mmol) in place of indole Compound 1a, a 1-(3-pyridinyl)-5-chloro-2-methyl-indol-3-yl glyoxylic methyl ester analog of Compound 1c (2.6 g) was obtained as in amber gum. The product was used in the next step without further purification.

The 1-(3-pyridinyl)-5-chloro-2-methyl-indol-3-yl glyoxylic methyl ester (492 mg, 0.0015 mole) and amide Compound 1f (260 mg, 0.001 mole) were combined in dry THF (10 mL) under argon and cooled in an ice bath as 1M potassium t-butoxide in THF (6 mL) was added with stirring over a 20 min period. After 4 h, the reaction stripped in vacuo to give a dark residue. The residue was purified by flash column chromatography on silica using an 85:13:2 mixture of methylene chloride:methanol:ammonia to elute the product. The eluant was stripped in vacuo to afford Compound 20 (0.26 g) as an orange flaky solid. Compound 20 was dissolved in one equivalent of dilute HCl, then frozen and lyophilized to give the hydrochloride salt. $^1$H NMR (DMSO-d$_6$) δ 8.80 (d, 1H), 8.60 (s, 1H), 7.95 (d, 1H), 7.80–7.70 (m, 2H), 7.35 (t, 1H), 7.30–7.20 (m, 2H), 7.10–7.00 (m, 3H), 4.60–4.50 (t, 2H), 3.15–3.00 (m, 2H), 2.65 (2s, 6H), 2.20–2.00 (m, 2H), 1.80 (s, 3H). ES-MS m/z 539 (MH+).

EXAMPLE 18

3-[1-[3-(dimethylamino)propyl]-1H-indazol-3-yl]-4-[1-(5-pyrimidinyl)-1H-indol-3-yl]-1H-pyrrole-2,5-dione (Compound 34)

Following the procedure of Example 1, using 5-bromopyrimidine (2.72 g, 17.1 mmol) in place of 3-bromopyridine, a 1-(5-pyrimidinyl)-indol-3-yl glyoxylic methyl ester analog of Compound 1c was obtained as a yellow solid (260 mg, 25%). $^1$H NMR (CDCl$_3$) δ 9.36 (s, 1H), 9.04 (s, 2H), 8.62 (s, 1H), 8.56–8.53 (m, 1H), 7.49–7.42 (m, 3H), 3.91 (s, 3H). ES-MS m/z 282 (MH+).

The 1-(5-pyrimidinyl)-indol-3-yl glyoxylic methyl ester (219 mg, 0.78 mmol) and amide Compound 1f (150 mg, 0.58 mmol) were combined in dry THF (15 mL) under nitrogen and cooled in an ice bath as 1M potassium t-butoxide in THF (2.3 mL, 2.3,mmol) was added with stirring over a 5 min period. After 2 h, the reaction was quenched in an ice bath 12N HCl (0.97) was slowly added and the mixture was stirred for 15 min. The reaction was diluted with chloroform (43 mL) and washed with saturated NaHCO$_3$ (2×15 mL) and brine (15 mL), then dried (K$_2$CO$_3$) and evaporated in vacuo to a solid. The solid was purified by flash column chromatography (91:7:2; DCM:MeOH: NH$_4$OH) to afford Compound 34 (0.069 g, 24%) as a red solid. The product was dissolved in 1N HCl:CH$_3$CN (2:1), then frozen and lyophilized to give the hydrochloride salt. $^1$H NMR (DMSO-d$_6$) δ 9.31 (s, 1H), 9.21 (s, 2H), 8.45 (s, 1H), 7.81 (dd, J=8.53, 8.25 Hz, 2H), 7.59 (d, J=8.36 Hz, 1H), 7.49–7.41 (m, 2H), 7.24–7.16 (m, 2H), 6.88 (t, J=7.76 Hz, 1H), 6.49 (d, J=7.95 Hz, 1H), 4.46 (t, J=6.83, 6.99 Hz, 2H), 3.09–2.93 (m, 2H) 2.60 (s, 6H), 2.29–1.91 (m, 2H). ES-MS m/z 492 (MH+). Anal. Calcd. For $C_{28}H_{25}N_7O_2 \cdot 1.73HCl \cdot 1.89H_2O$ (491.54/588.67): C, 57.13; H, 5.23; N, 16.66; Cl, 10.42; KF, 5.79. Found: C, 56.76; H, 5.50; N, 17.43; Cl, 9.99; KF, 5.43.

EXAMPLE 19

3-[1-[3-(dimethylamino)propyl]-1H-indol-3-yl]-4-[1-(3-pyridinyl)-1H-indazol-3-yl]-1H-pyrrole-2,5-dione (Compound 59)

The indol-3-yl-glyoxylic methyl ester (0.50 g, 2.46 mmol) Compound 2b and 3-dimethylamino propyl chloride hydrochloride (0.44 g, 2.78 mmol) were combined in DMF (5 mL) and cooled to 0° C. as 95% NaH (135 mg, 5.34 mmol) was added. The reaction vessel was placed in an oilbath at 55° C. for 20 h and then cooled to ambient temperature. The solution was diluted with DCM (30 mL), washed with water, 3 times with saturated NaHCO₃ and once with brine, then dried (K₂CO₃) and evaporated in vacuo to give an oil (0.44 g, 62%). The oil was purified via flash column (DCM:MeOH; 10:1) to afford Compound 19a. ES-MS m/z 289 (MH⁺).

Following the procedure for converting Compound 1a to Compound 1b, the indazole Compound 1e (350 mg, 2.0 mmol) was combined with 3-bromopyridine (332 mg. 2.1 mmol) to give a crude product Compound 19b (410 mg). Compound 19b was purified by flash column chromatography (DCM:MeOH; 10:1) to a tan solid. ES-MS m/z 253 (MH⁺). ¹H NMR (CDCl₃) δ 9.1 (s, 1H), 8.62 (d, J=2 Hz, 1H), 8.1 (d, J=8.0 Hz, 1H), 7.75 (m, 2H), 7.50 (m, 2H), 7.34 (m, 1H), 4.10 (s, 2H).

Following the procedure of Example 1, the ester Compound 19a (55 mg, 0.19 mmol) and the amide Compound 19b (37 mg, 0.147 mmol) in THF (3 mL) were combined with 1M potassium t-butoxide in THF (0.60 mL, 0.60 mmol) at 0° C. to give a crude product Compound 59 (60 mg) as an orange solid. Compound 59 was then purified by flash column chromatography (DCM:MeOH:NH₄OH; 90:9:1) (50 mg, 69%), then dissolved in aqueous HCl, then frozen and lyophilized to the hydrochloride salt. ES-MS m/z 491 (MH⁺). ¹H NMR (DMSO) δ 8.54 (m, 2H), 8.31 (s, 1H), 7.90 (m, 3H), 7.6 (m, 3H), 7.32 (dd, J=7.4, 7.7 Hz, 1H), 7.11 (dd, J=7.3, 7.7 Hz, 1H), 6.69 (dd, J=7.4, 7.7 Hz, 1H), 6.23 (d, J=8.0 Hz, 1H), 4.42 (m, 2H), 3.08 (m, 2H), 2.73/2.75 (2 s, 6H), 2.21 (m, 2H).

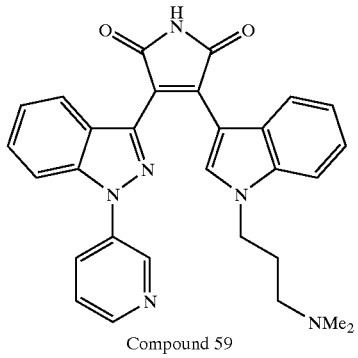

Compound 59

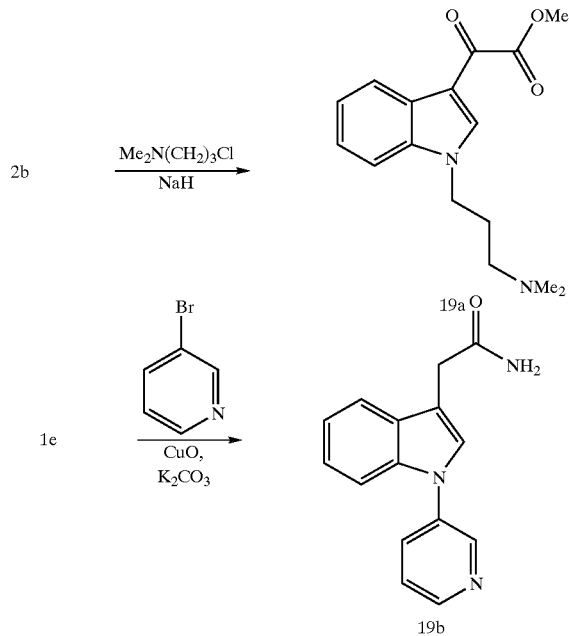

EXAMPLE 20

3-(1-benzo[b]thien-3-yl -1H-indol-3-yl)-4-[1-[3-(dimethylamino)propyl]-1H-indazol-3-yl]-1H-pyrrole-2,5-dione (Compound 60)

Following the procedure of Example 1, using 3-bromobenzo[b]thiophene (3.64 g, 17.1 mmol) in place of 3-bromopyridine, a 1-(3-benzo[b]thienyl)-indol-3-yl glyoxylic methyl ester analog of Compound 1c was obtained as a yellow solid (0.97 g, 69%). ¹H NMR (CDCl₃) δ 8.55 (s, 1H), 8.47 (d, J=7.9 Hz, 1H), 7.91 (d, J=2.7 Hz, 1H), 7.60 (s, 1H), 7.44–7.18 (m, 6H), 3.89 (s, 3H). ES-MS m/z 336 (MH⁺).

The 1-(3-benzo[b]thienyl)-indol-3-yl glyoxylic methyl ester (272 mg, 0.81 mmol) and amide Compound 1f (150 mg, 0.58 mmol) were combined in dry THF (8 mL) under nitrogen and cooled in an ice bath as 1M potassium t-butoxide in THF (2.3 mL, 2.3 mmol) was added with stirring over a 15 min period. The reaction was warmed to rt and stirred at rt for 3 h. The reaction was diluted with ethyl acetate (138 mL) and washed with water (2×28 mL), saturated NaHCO₃ (56 mL) and brine (56 mL), then dried (Na₂SO₄) and evaporated in vacuo to provide a solid. The solid was purified by flash column chromatography (97.5:0.5:2; DCM:MeOH:NH₄OH) to afford Compound 60 (0.12 g, 40%) as a red solid. Compound 60 was dissolved in 1N HCl:CH₃CN (2:1), then frozen and lyophilized to give the hydrochloride salt. ¹H NMR (free base, CDCl₃) δ 8.29 (s, 1H), 7.94 (d, J=8.0 Hz, 1H), 7.75 (d, J=8.2 Hz, 1H), 7.60 (s, 1H), 7.55–7.35 (m, 5H), 7.23–7.04 (m, 3H), 6.80 (t, J=7.2 Hz, 1H), 6.57 (d, J=8.0 Hz, 1H), 4.40 (t, J=6.94 Hz, 2H), 2.26–2.13 (m, 8H), 1.89–1.62 (m, 2H). ES-MS m/z 546 (MH⁺). Anal. Calcd. For $C_{32}H_{27}N_5O_2S \cdot 1.03HCl \cdot 1.75H_2O$ (545.66/614.74): C, 62.53; H, 5.17; N. 11.40; Cl, 5.95; KF, 5.13. Found: C, 62.32; H, 4.98; N, 11.53; Cl, 5.93; KF, 5.11.

EXAMPLE 21

3-(1-[1,1'-biphenyl]-3-yl-1H-indol-3-yl)-4-[1-[3-(dimethylamino)propyl]-1H-indazol-3-yl]-1H-pyrrole-2,5-dione (Compound 61)

Following the procedure of Example 1, using 3-bromobiphenyl (2.13 mL, 12.8 mmol) in place of 3-bromopyridine, a 1-(3-phenyl-phenyl)-indol-3-yl glyoxylic methyl ester analog of Compound 1c was obtained as a yellow solid (1.01 g, 77%). ¹H NMR (CDCl₃) δ 8.63 (s, 1H), 8.53 (d, J=7.22 Hz, 1H), 7.75–7.62 (m, 4H), 7.55–7.33 (m, 8H), 3.97 (s, 3H). ES-MS m/z 356 (MH⁺).

The 1-(3-phenyl-phenyl)-indol-3-yl glyoxylic methyl ester (288 mg, 0.81 mmol) and amide Compound 1f (150 mg, 0.58 mmol) were combined in dry THF (8 mL) under nitrogen and cooled in an ice bath as 1M potassium t-butoxide in THF (2.3 mL, 2.3 mmol) was added with stirring over a 15 min period. The reaction was warmed to rt and stirred at rt for 2 h. The reaction was diluted with ethyl acetate (138 mL), washed with water (2×28 mL), saturated NaHCO3 (56 mL) and brine (56 mL), then dried ($Na_2SO_4$) and evaporated in vacuo to give a solid. The solid was purified by flash column chromatography (97.5:0.5:2; DCM:MeOH:$NH_4OH$) to afford Compound 61 (0.099 g, 30%) as a red solid. Compound 61 was then dissolved in 1N HCl:$CH_3CN$ (2:1), then frozen and lyophilized to give the hydrochloride salt. $^1H$ NMR (free base, $CDCl_3$) δ 8,34 (s 1H), 7.80–7.38 (m, 13H), 7.26–7.08 (m, 2H), 6.77 (t, J=7.28, 7.25 Hz, 1H), 6.46 (d, J=8.05 Hz, 1H), 4.37 (t, J=6.92, 6.96 Hz, 2H), 2.22–2.10 (m, 8H), 1.85–1.78 (m, 2H). ES-MS m/z 566 ($MH^+$). Anal. Calcd. for $C_{36}H_{31}N_5O_2 \cdot 1.14HCl \cdot 1.98H_2O$ (565.66/642.92): C, 67.26; H, 5.66; N, 10.90; Cl, 6.29; KF, 5.52. Found: C, 66.86; H, 5.62; N, 10.87; Cl, 5.50; KF, 5.19.

Using the procedure of Example 21 and the appropriate reagents and starting materials known to those skilled in the art, other compounds of the present invention may be prepared including, but not limited to:

| Cpd | Name | ES-MS m/z ($MH^+$) |
|---|---|---|
| 72 | 3-[1-[3-(dimethylamino)propyl]-1H-indazol-3-yl]-4-[1-[3-(3-thienyl)phenyl]-1H-indol-3-yl]-1H-pyrrole-2,5-dione | 572 |

EXAMPLE 22

3-[1-3-(4-morpholinyl)propyl]-1H-indazol-3-yl]-4-[1-(3-pyridinyl)-1H-indol-3-yl-1H-pyrrole-2,5-dione (Compound 68)

Following the procedure for converting Compound 1e to Compound 1f, the indazole Compound 1e (1.58 g, 9 mmol) in DMF (20 mL) was combined with 3-chloropropylmorpholine (1.62 g, 9.90 mmol) and cooled in an ice bath as 95% NaH (sodium hydride) (0.25 g, 9.90 mmol) was added portionwise over a 20 min period. The reaction was stirred at ambient temperature for 10 min and then placed in an oil bath at 55° C. for 2 h. After cooling to rt, the reaction was diluted with DCM (200 mL), washed 3 times with brine (60 mL), then dried ($K_2CO_3$) and evaporated in vacuo to give an oil (2.60 g). The oil was purified by flash column chromatography (EtOAc:MeOH:$NH_4OH$; 80:10:1) to afford a 1-[3-(morpholino)propyl]-1H-indazol-3-yl analog of Compound 1f as a white solid (1.34 g, 49%).

Following the procedure of Example 1, the 1-[3-(morpholino)propyl]-1H-indazol-3-yl (151 mg, 0.50 mmol) and ester Compound 1c (170 mg, 0.6 mmol) were stirred in THF (5 mL) at 0° C. as 1M potassium t-butoxide in THF (2.0 mL, 2.0 mmol) was added over 3 min and reaction stirred for 1 h. The reaction was quenched at 0° C. with HCl (12N, 0.90 mL), stirred for 15 min and then poured into saturated $NaHCO_3$ and extracted with chloroform. The organic solution was washed with brine, then dried ($Na_2SO_4$) and evaporated in vacuo to give an orange solid. The solid was purified via flash column chromatography (EtOAc:MeOH:$NH_4OH$; 80:8:2) to give Compound 68 (160 mg, 62%) as an orange solid. Compound 68 was dissolved in aqueous HCl, then frozen and lyophilized to the hydrochloride salt (170 mg). ES-MS m/z 533 ($MH^+$). $^1H$ NMR ($CD_3OD$, 300 MHz) δ 9.26 (s, 1H), 8.90 (m, 2H), 8.39 (s, 1H), 8.19 (m, 1H), 7.66 (m, 2H), 7.55 (d, J=8.2 Hz, 1H), 7.43 (m, 1H), 7.21 (m, 1H), 7.07 (m, 1H), 6.81 (dd, J=7.6, 7.7 Hz, 1H), 6.47 (d, J=8.0 Hz, 1H), 4.54 (dd, J=6.4, 6.4 Hz, 2H), 3.98 (m, 2H), 3.75 (m, 2H), 3.38 (m, 2H), 3.15 (m, 2H), 2.94 (m, 2H), 2.25 (m, 2H).

EXAMPLE 23

3-[1-(3-(4-morpholinyl)propyl]-1H-indazol-3-yl]-4-[1-(2-naphthalenyl)-1H-indol-3-yl]-pyrrole-2,5-dione (Compound 70)

Following the procedure of Example 1 for combining Compound 1c and Compound 1f to obtain a target compound, the 1-(2-naphthyl)-inidol-3-yl-glyoxylic methyl ester (296 mg, 0.90 mmol) analog of Compound 1c (prepared in Example 11) in THF (6.0 mL) and the 1-[3-(morpholino)propyl]-1H-indazol-3-yl (226 mg, 0.75 mmol) analog of Compound 1f (prepared in Example 22) were combined with 1M potassium t-butoxide in THF (3.0 mL, 3.0 mmol) to afford a crude product. The product was flash column purified to give Compound 70 (200 mg, 46%) as an orange solid. Compound 70 was dissolved in aqueous HCl, then frozen and lyophilized to afford the hydrochloride salt (219 mg). ES-MS m/z 582 ($MH^+$). $^1H$ NMR ($CD_3OD$, 300 MHz) δ 8.34 (s, 1H), 8.11 (d, J=8.8 Hz, 1H), 8.05 (s, 1H), 7.98 (m, 2H), 7.60 (m, 6H), 7.45 (m, 1H), 7.13 (m, 2H), 6.75 (dd, J=7.3, 7.8 Hz, 1H), 6.44 (d, J=8.1 Hz, 1H), 4.53 (dd, J=6.3, 6.4 Hz, 2H), 3.80 (m, 4H), 3.01 (m, 6H), 2.22 (m, 2H).

EXAMPLE 24

3-[1-(3-hydroxypropyl)-1H-indazol-3-yl]-4-[1-(2-naphthalenyl)-1H-indol-3-yl]-1H-pyrrole-2,5-dione (Compound 84)

The indazole Compound 1e (5 g, 28.6 mmol) was combined with a silyl-protected 3-bromo-1-propanol Compound 24a (8.33 g, 32.9 mmol) in the presence of $Cs_2CO_3$ (12.11 g, 37 mmol) in DMF (50 mL) at 68° C. for 3 h. The mixture was cooled to rt, water was added and extracted with EtOAc several times. The organic layers were combined and washed with brine, then dried ($Na_2SO_4$) and evaporated in vacuo to provide an oil. The oil was purified by flash column chromatography (95:5:0.5; DCM:MeOH:$NH_4OH$) to give an amide Compound 24b (9.9 g, 100%). $^1H$ NMR ($CDCl_3$) δ 7.65 (m, 1H), 7.38 (m, 2H), 7.13 (m, 1H), 6.53 (bd s, 1H), 5.44 (bd s, 1H), 4.44 (t, J=6.82 Hz, 2H), 3.93 (s, 2H), 3.56 (t, J=5.73 Hz. 2H), 2.08 (m, 2H), 0.89 (s, 9H), 0.01 (s, 6H). ES-MS m/z 348 ($MH^+$).

The 1-(2-naphthyl)-indol-3-yl-glyoxylic methyl ester (0.13 g, 0.40 mmol) analog of Compound 1c (prepared in Example 11) and amide Compound 24b (0.1 g, 0.29 mmol) were combined in dry THF (8 mL) under argon and cooled in an ice bath as 1M potassium t-butoxide in THF (1.4 mL, 1.4 mmol) was added with stirring over a 5 min period. After 40 min, the reaction was quenched in an ice bath while 12 N HCl (2 mL, 24 mmol) was slowly added over a 2 min period. The mixture was stirred for 5 min, made basic to slightly basic by the addition of 3N NaOH and extracted with EtOAc. The organic layers were combined and washed with saturated $NaHCO_3$ and brine, then dried ($Na_2SO_4$) and evaporated in vacuo to afford Compound 84 (72 mg, 49%) as an orange flaky solid. The solid was then purified by flash column chromatography (96:4:0.4; DCM:MeOH:$NH_4OH$).

¹H NMR (CDCl3) δ 8.34 (s, 1H), 7.93 (m, 4H), 7.79 (m, 2H), 7.68 (d, J=2.13 Hz, 1H), 7.58 (m, 3H), 7.44 (m, 1H), 7.16 (m, 2H), 6.78 (m, 1H), 6.50 (d, J=8.0 Hz, 1H), 4.47 (t, J=6.3 Hz, 2H), 3.40 (t, J=5.8 Hz, 2H), 1.89 (m, 2H). ES-MS m/z 513 (MH+).

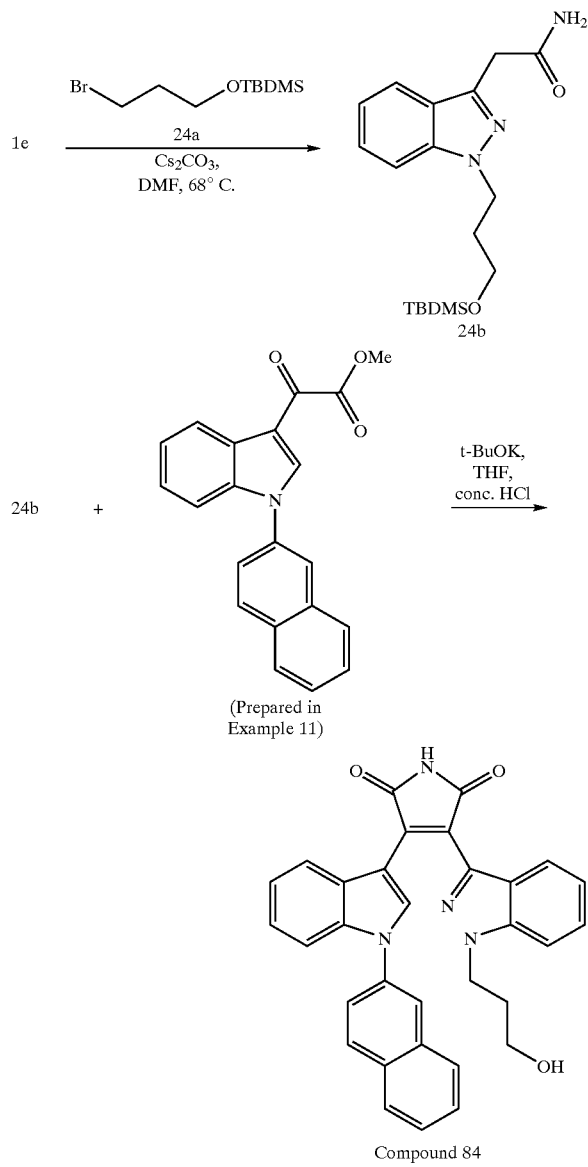

Compound 84

Using the procedure of Example 24 and the appropriate reagents and starting materials known to those skilled in the art, other compounds of the present invention may be prepared including, but not limited to:

| Cpd | Name | ES-MS m/z (MH+) |
|---|---|---|
| 91 | 3-[1-(4-hydroxybutyl)-1H-indazol-3-yl]-4-[1-(2-naphthalenyl)-1H-indol-3-yl]-1H-pyrrole-2,5-dione | 527 |
| 92 | 3-(1-benzo[b]thien-3-yl-1H-indol-3-yl)-4-[1-(4-hydroxybutyl)-1H-indazol-3-yl]-1H-pyrrole-2,5-dione | 533 |
| 99 | 3-(1-benzo[b]thien-3-yl-1H-indol-3-yl)-4-[1-(2-hydroxyethyl)-1H-indazol-3-yl]-1H-pyrrole-2,5-dione | 505 |
| 100 | 3-[1-(2-hydroxyethyl)-1H-indazol-3-yl]-4-[1-(2-naphthalenyl)-1H-indol-3-yl]-1H-pyrrole-2,5-dione | 499 |

EXAMPLE 25

3-(5-chloro-1-methyl-1H-indol-3-yl)-4-[1-(3-hydroxypropyl)-1H-indazol-3-yl]-1H-pyrrole-2,5-dione (Compound 74)

Following the procedure of Example 7, a N-methyl substituted indole methyl ester analog of Compound 7a (0.37 g, 1.47 mmol) and the amide Compound 24b (0.34 g, 0.98 mmol) (prepared in Example 24 and containing a small amount of the N-2 alkylated indazole isomer) were combined in dry THF (5 mL) under argon and cooled in an ice bath as 1M potassium t-butoxide in THF (4.9 mL, 4.90 mmol) was added with stirring over a 10 min period. After 40 min, the reaction was quenched in an ice bath while 12 N HCl (5 mL, 60 mmol) was slowly added over a 5 min period. The mixture was stirred for 10 min, then made basic to slightly basic with 3N NaOH and extracted with EtOAc. The organic layers were combined and washed with saturated NaHCO3 and brine, then dried (Na2SO4) and evaporated in vacuo to afford Compound 74 (0.13 g, 30%) as an orange flaky solid. Compound 74 was then purified by flash column chromatography (96:4:0.4; DCM:MeOH:NH4OH). ¹H NMR (CD3OD) δ 8.14 (s, 1H), 7.63 (d, J=8.3 Hz, 1H), 7.46 (d, J=8.3 Hz, 1H), 7.36 (m, 2H), 7.02 (t, J=7.1 Hz, 2H), 6.04 (d, J=1.2 Hz, 1H), 4.51 (t, J=6.8 Hz, 2H), 3.89 (s, 3H), 3.52 (t, J=5.84 Hz, 2H), 2.00 (m, 2H). ES-MS m/z 435 (MH+). Anal. Calcd. for $C_{23}H_{19}ClN_4O_3$: C, 63.53; H, 4.41; Cl, 8.16; N, 12.89. Found: C, 63.47; H, 4.28; t, 12.63; Cl, 8.49.

EXAMPLE 26

3-(5-chloro-1-methyl-1H-indol-3-yl)-4-[1-[3-[(2-hydroxyethyl)methylamino]propyl]-1H-indazol-3-yl]-1H-pyrrole-2,5-dione (Compound 79)

Pyridine (0.37 g, 4.62 mmol) and methanesulfonic anhydride (0.54 g, 3.08 mmol) were added to Compound 74 (0.67 g, 1.54 mmol) in THF (10 mL). The mixture was heated at 50° C. for 2 h, then cooled to rt. Another portion of THF (5 mL) was added, Followed by 1N HCl (5 mL). The mixture was stirred for another 15 min, then extracted with EtOAc, several times. The combined EtOAc layers were washed once with 1N HCl (10 mL), water (2×20 mL) and saturated NaCl (20 mL), then dried (Na2SO4) and evaporated in vacuo to obtain 3-(5-chloro-1-methyl-1H-indol-3-yl)-4-[1-[3-[(methylsulfonyl)oxy]propyl]-1H-indazol-3-yl]-1H-pyrrole-2,5-dione as Compound 26a (0.73 g, 92%) as a reddish solid. ES-MS m/z 513 (MH+).

2-(methylamino)ethanol (0.4 mL) was added to Compound 26a (0.1 g, 0.2 mmol) in DMA (5 mL). The mixture was heated at 65° C. for 3 h, then cooled to rt. Water (5 mL) was added, then the mixture was extracted with EtOAc (3×50 mL). The organic layers were combined, washed with H2O and brine, then dried (Na2SO4) and evaporated in vacuo to a dark oil. The oil was purified by flash column chromatography (96:4:0.4; DCM:MeOH:NH$_4$OH) to afford Compound 79 (25 mg, 25%) as an orange flaky solid. Compound 79 was dissolved in excess dilute HCl, then frozen and lyophilized to give the hydrochloride salt. $^1$H NMR (CD$_3$OD) δ 8.01 (s, 1H), 7.53 (d, J=8.6 Hz, 1H), 7.41 (d, J=8.2 Hz, 1H), 7.29 (m, 1H), 7.21 (d, J=8.7 Hz, 1H), 6.96 (s, 1H), 6.92 (m, 1H), 5.88 (d, J=1.9 Hz, 1H), 4.33 (t, J=7.0 Hz, 2H), 3.75 (s, 3H), 3.47 (t, J=6.0 Hz, 2H), 2.33 (t, J=6.0 Hz, 2H), 2.26 (t, J=7.0 Hz, 2H), 2.09 (s, 3H), 1.84 (m, 2H). ES-MS m/z 492 (MH$^+$).

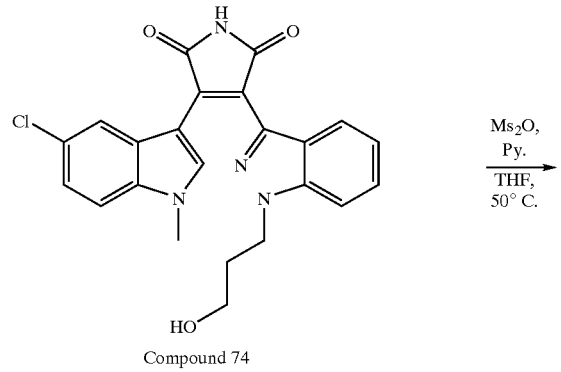

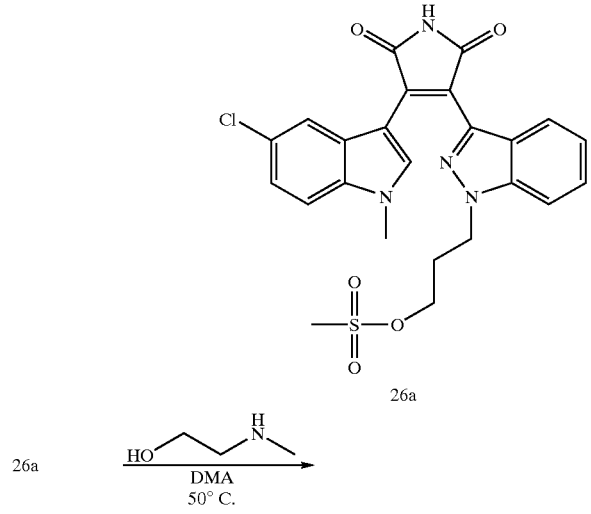

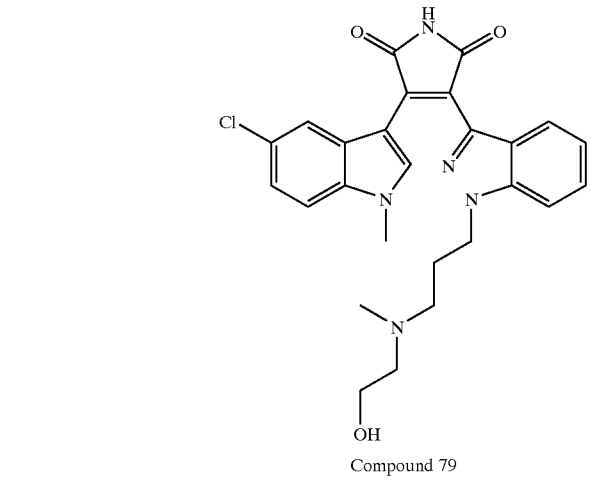

Using the procedure of Example 26 and the appropriate reagents and starting materials known to those skilled in the art, other compounds of the present invention may be prepared including, but not limited to:

| Cpd | Name | ES-MS m/z (MH$^+$) |
| --- | --- | --- |
| 75 | 3-(5-chloro-1-methyl-1H-indol-3-yl)-4-[1-[3-(1-pyrrolidinyl)propyl]-1H-indazol-3-yl]-1H-pyrrole-2,5-dione | 488 |
| 76 | 3-[1-[3-(acetyloxy)propyl]-1H-indazol-3-yl]-4-(5-chloro-1-methyl-1H-indol-3-yl)-1H-pyrrole-2,5-dione | 477 |
| 77 | 3-(5-chloro-1-methyl-1H-indol-3-yl)-4-[1-[3-(4-methyl-1-piperazinyl)propyl]-1H-indazol-3-yl]-1H-pyrrole-2,5-dione | 517 |
| 78 | 3-(5-chloro-1-methyl-1H-indol-3-yl)-4-[1-[3-(4-morpholinyl)propyl]-1H-indazol-3-yl]-1H-pyrrole-2,5-dione | 504 |
| 80 | 3-(5-chloro-1-methyl-1H-indol-3-yl)-4-[1-[3-(methylamino)propyl]-1H-indazol-3-yl]-1H-pyrrole-2,5-dione | 448 |
| 82 | 3-(5-chloro-1-methyl-1H-indol-3-yl)-4-[1-[3-[methyl(phenylmethyl)amino]propyl]-1H-indazol-3-yl]-1H-pyrrole-2,5-dione | 538 |

EXAMPLE 27

3-[1-(2-naphthalenyl)-1H-indol-3-yl]-4-[1-[3-(1-pyrrolidinyl)propyl]-1H-indazol-3-yl]-1H-pyrrole-2,5-dione (Compound 85)

Following the procedure of Example 26, pyridine (0.7 g, 8.35 mmol) and methanesulfonic anhydride (1.09 g, 6.26 mmol) were added to Compound 84 (1.07 g, 2.09 mmol) (prepared in Example 24) in THF (20 mL). The mixture was heated at 50° C. for 2 h, then cooled to rt. Another portion of THF (10 mL) was added, followed by addition of 1N HCl (10 mL). The mixture was stirred for 15 min, then extracted with EtOAc several times. The combined EtOAc layers were washed once with 1 N HCl (10 mL), water (2×20 mL) and saturated NaCl (20 mL), then dried (Na$_2$SO$_4$) and evaporated in vacuo to obtain a 3-[1-[3-[(methylsulfonyl)oxy]propyl]-1H-indazol-3-yl]-4-[1-(2-naphthalenyl)-1H-indol-3-yl]-1H-pyrrole-2,5-dione analog of Compound 26a (1.1 g, 92%) as a reddish solid. ES-MS m/z 591 (MH$^+$).

Pyrrolidine (1 mL) was added to the 3-[1-[3-[(methylsulfonyl)oxy]propyl]-1H-indazol-3-yl]-4-[1-(2-naphthalenyl)-1H-indol-3-yl]-1H-pyrrole-2,5-dione (0.5 g, 0.975 mmol) in DMA (10 mL). The mixture was heated to 65° C. for 3 h, then cooled to rt. Water (5 mL) was added, followed by extraction with EtOAc (3×50 mL). The organic layers were combined, washed with H$_2$O and brine, then dried (Na$_2$SO$_4$) and evaporated in vacuo to a dark brown oil. The oil was purified by flash column chromatography (97:3:0.3; DCM:MeOH:NH$_4$OH) to afford Compound 85 (0.1 g, 18%) as an orange flaky solid. Compound 85 was dissolved in excess dilute HCl, then frozen and lyophilized to give the hydrochloride salt. $^1$H NMR (CD$_3$OD) δ 8.22 (s, 1H), 8.01 (d, J=8.8 Hz, 1H), 7.89 (m, 3H), 7.49 (m, 7H), 7.00 (m, 2H), 6.64 (t, J=7.5 Hz, 1H), 6.39 (d, J=8.1 Hz, 1H), 4.47 (t, J=6.2 Hz, 2H), 3.44 (m, 2H), 3.07 (t, J=7.4 Hz, 2H), 2.82 (m, 2H), 2.16 (m, 2H), 1.93 (m, 4H). ES-MS m/z 566 (MH$^+$).

Using the procedure of Example 27 and the appropriate reagents and starting materials known to those skilled in the art, other compounds of the present invention may be prepared including, but not limited to:

| Cpd | Name | ES-MS m/z (MH+) |
|---|---|---|
| 88 | 3-[1-[3-[(2-hydroxyethyl)methylamino]-propyl]-1H-indazol-3-yl]-4-[1-(2-naphthalenyl)-1H-indol-3-yl]-1H-pyrrole-2,5-dione | 570 |
| 89 | 3-[1-[3-(4-methyl-1-piperazinyl)propyl]-1H-indazol-3-yl]-4-[1-(2-naphthalenyl)-1H-indol-3-yl]-1H-pyrrole-2,5-dione | 595 |
| 114 | 3-[1-[3-[(2-hydroxyethyl)methylamino]-propyl]-1H-indazol-3-yl]-4-[1-(3-pyridinyl)-1H-indol-3-yl]-1H-pyrrole-2,5-dione | 521 |
| 119 | 3-[1-[3-(acetyloxy)propyl]-1H-indazol-3-yl]-4-[1-(3-pyridinyl)-1H-indol-3-yl]-1H-pyrrole-2,5-dione | 506 |

EXAMPLE 28

3-[1-(3-hydroxypropyl)-1H-indazol-3-yl]-4-[1-(3-pyridinyl)-1H-indol-3-yl]-1H-pyrrole-2,5-dione (Compound 94)

Following the procedure of Example 25, the ester Compound 1c (2.4 g, 8.56 mmol) and amide Compound 24b (2 g, 5.75 mmol) were combined in dry THF (10 mL) under argon and cooled in an ice bath as 1M potassium t-butoxide in THF (28 mL, 28 mmol) was added with stirring over a 20 min period. After 40 min, the reaction was quenched in an ice bath, 12 N HCl (10 mL, 120 mmol) was slowly added over a 5 min period. The mixture was stirred for 10 min and made basic to slightly basic with 3N NaOH, then extracted with EtOAc. The organic layers were combined and washed with saturated $NaHCO_3$ and brine, then dried ($Na_2SO_4$) and evaporated in vacuo to a flaky solid. The solid was purified by flash column chromatography (96:4:0.4; DCM:MeOH:$NH_4OH$) to afford Compound 94 (1.70 g, 64%) as an orange flaky solid. Compound 94 was dissolved in excess dilute HCl, then frozen and lyophilized to give the hydrochloride salt. $^1$H NMR ($CD_3OD$) δ 9.33 (s, 1H), 8.91 (m, 2H), 8.29 (m, 2H), 7.64 (m, 3H), 7.39 (t, J=7.4 Hz, 1H), 7.19 (t, J=7.6 Hz, 1H), 7.08 (t, J=7.9 Hz, 1H), 6.77 (t, J=7.7 Hz, 1H), 6.39 (d, J=7.9 Hz, 1H), 4.40 (t, J=6.3 Hz, 2H), 3.36 (t, J=5.6 Hz, 2H), 1.80 (t, J=6.0 Hz, 2H). ES-MS m/z 464 (MH+). Anal. Calcd. for $C_{27}H_{21}N_5O_3 \cdot 1.3HCl \cdot 1.03H_2O$ (463.49/515.29): C, 61.26; H, 4.64; N, 13.23; Cl, 8.71; KF, 3.51. Found. C, 61.63; H, 4.64; N, 13.48; Cl, 9.13; KF, 3.97.

Using the procedure of Example 28 and the appropriate reagents and starting materials known to those skilled in the art, other compounds of the present invention may be prepared including, but not limited to:

| Cpd | Name | ES-MS m/z (MH+) |
|---|---|---|
| 102 | 3-[1-(3-hydroxypropyl)-1H-indazol-3-yl]-4-[1-(2-pyridinyl)-1H-indol-3-yl]-1H-pyrrole-2,5-dione | 464 |
| 105 | 3-[1-(3-hydroxypropyl)-1H-indazol-3-yl]-4-[1-(4-isoquinolinyl)-1H-indol-3-yl]-1H-pyrrole-2,5-dione | 514 |
| 106 | 3-[1-[2-(2-hydroxyethoxy)ethyl]-1H-indazol-3-yl]-4-[1-(3-pyridinyl)-1H-indol-3-yl]-1H-pyrrole-2,5-dione | 494 |
| 110 | 3-[1-(2-hydroxyethyl)-1H-indazol-3-yl]-4-[1-(3-pyridinyl)-1H-indol-3-yl]-1H-pyrrole-2,5-dione | 450 |
| 111 | 3-[1-(4-hydroxybutyl)-1H-indazol-3-yl]-4-[1-(3-pyridinyl)-1H-indol-3-yl]-1H-pyrrole-2,5-dione | 478 |

EXAMPLE 29

3-(7-chloro-1-ethyl-1H-indol-3-yl)-4-[1-[3-(dimethylamino)propyl]-1H-indazol-3-yl]-1H-pyrrole-2,5-dione (Compound 95)

Following the procedure of Example 4, using 7-chloroindole in place of 5-chloroindole, 7-chloroindole (12.5 g, 0.082 mole) in a mixture with ether (150 mL) was cooled in an ice bath and treated dropwise with oxalyl chloride (10.9 g, 0.086 mole) while stirring under argon. The resulting yellow slurry was stirred at 5° C. for 30 min then cooled to −65° C. Anhydrous methanol (25 mL) was added dropwise to the cold mixture over a 30 min period. The mixture was allowed to warm to rt and was stirred for 4 h. The resulting suspension of yellow solid was filtered and the solid washed with ether and air dried to give a 7-chloroindole methyl ester analog of Compound 4b (13.6 g). The crude product was used in the next step without further purification.

Following the procedure of Example 7, a mixture of the 7-chloroindole methyl ester (3.0 g, 0.013 mole) and cesium carbonate (8.5 g, 0.026 mole) in anhydrous DMF (75 mL) was stirred at 30° C. under argon for 1 h. Iodoetharie (9.8 g, 0.063 mole) was added dropwise and the mixture was stirred overnight at 25–30° C. The reaction mixture was then diluted with ether (1 L) and partitioned with water (100 mL). The organic layer was separated and the aqueous layer extracted with ether (200 mL). The combined organic layers were washed with brine, then dried over anhydrous sodium sulfate and concentrated in vacuo to give a N-ethyl substituted 7-chloroindole methyl ester analog of Compound 7a (3.3 g) as a white solid. The solid was used in the next step without further purification.

A mixture of Compound 1f (see Example 1) (170 mg, 0.65 mmol) and the N-ethyl substituted 7-chloroindole methyl ester (207 mg, 0.78 mmol) in anhydrous THF (6 mL) was stirred in an ice bath under argon. 1N solution of potassium t-butoxide (2.6 mL) in THF was added to the mixture dropwise while stirring under argon. The mixture was then stirred for an additional 2.5 h at rt and then cooled in an ice bath and quenched with concentrated hydrochloric acid (1.5 mL). The mixture was stirred for 15 min then partitioned with chloroform and saturated sodium bicarbonate solution. The chloroform layer was washed with brine, then dried over anhydrous sodium sulfate and concentrated in vacuo to give an orange glass (334 mg). The orange glass was dissolved in a 90:10 mixture of chloroform:methanol, then filtered through a plug of silica and stripped in vacuo to give a residual orange solid. The orange solid was purified via reverse-phase HPLC using a gradient of 30%-100% acetonitrile/water (containing 0.2% TFA) to elute the product as a TFA salt. The salt was freeze-dried to give Compound 95 (130 mg) as a fluffy orange solid. $^1$H NMR (DMSO-$d_6$) δ 8.20 (s, 1H), 7.75 (d, 1H), 7.60 (d, 1H), 7.40 (t, 1H), 7.15–7.05 (m, 2H), 6.70 (t, 1H), 6.35 (d, 1H), 4.65

(q, 2H), 4.40 (t, 2H), 3.00 (m, 2H), 2.70 (s, 6H), 2.00 (m, 2H), 1.40 (t, 3H). ES-MS m/z 476 (MH$^+$). Anal. Calc'd for $C_{26}H_{26}ClN_5O_2 \cdot 1.15$ TFA$\cdot 0.5H_2O$: C, 55.17; H, 4.61; N, 11.37; F, 10.64, H$_2$O, 1.46. Found: C, 55.36; H, 4.53; N, 11.42; F, 10.61; H$_2$O, 1.12.

EXAMPLE 30

3-[4-[1-[3-(dimethylamino)propyl]-1H-indazol-3-yl]-2,5-dihydro-2,5-dioxo-1H-pyrrol-3-yl]-1-ethyl-1H-indole-5-carbonitrile (Compound 98)

Following the procedure of Example 4, using 5-cyanoindole in place of 5-chloroindole, 5-cyanoindole (13.7 g, 0.096 mole) in a mixture with ether (200 mL) was cooled in an ice bath and treated dropwise with oxalyl chloride (12.7 g, 0.1 mole) while stirring under argon. The resulting yellow slurry was stirred at 5° C. for 30 min then cooled to −65° C. Anhydrous methanol (25 mL) was added dropwise to the cold mixture over a 30 min period. The mixture was allowed to warm to rt and was stirred for 4 h. The resulting suspension of yellow solid was filtered and the solid washed with ether and air-dried to give a 5-cyanoindole methyl ester analog of Compound 4b (18.4 g). The crude product was used in the next step without further purification.

Following the procedure of Example 7, a mixture of the 5-cyanoindole methyl ester (2.97 g, 0.013 mole) and cesium carbonate (8.5 g, 0.026 mole) in anhydrous DMF (75 mL) was stirred at 30° C. under argon for 1 h. Iodoethane (9.8 g, 0.063 mole) was then added dropwise and the mixture was stirred overnight at 25–30° C. The reaction mixture was then diluted with ether (1 L) and partitioned with water (100 mL). The organic layer was separated and the aqueous layer extracted with ether (200 mL). The combined organic layers were washed with brine, then dried over anhydrous sodium sulfate and concentrated in vacuo to give a N-ethyl substituted 5-cyanoindole methyl ester analog of Compound 7a (1.7 g) as a white solid. The solid was used in the next step without further purification.

A mixture of Compound 1f (see Example 1) (170 mg, 0.65 mmol) and the N-ethyl substituted 5-cyanoindole methyl ester (207 mg, 0.78 mmol) in anhydrous THF (6 mL) was stirred in an ice bath under argon. 1N solution of potassium t-butoxide (2.6 mL) in THF was added to the mixture dropwise while stirring under argon. The mixture was then stirred for an additional 2.5 h at rt and then cooled in an ice bath and quenched with concentrated hydrochloric acid (1.5 mL). The mixture was stirred for 15 min then partitioned with chloroform and saturated sodium bicarbonate solution. The chloroform layer was washed with brine, then dried over anhydrous sodium sulfate and concentrated in vacuo to give an orange glass. The orange glass was purified via reverse-phase HPLC using a gradient of 30%–100% acetonitrile/water containing 0.2% TFA) to elute the product as a TFA salt. The salt was freeze-dried to give Compound 98 (155 mg) as a fluffy orange solid. $^1$H NMR (DMSO-d$_6$) δ 8.45 (s, 1H), 7.80–7.70 (m, 2H), 7.55–7.40 (m, 3H), 7.10 (t, 1H), 6.70 (s, 1H), 4.50 (t, 2H), 4.35 (q, 2H), 3.10 (m, 2H), 2.75 (s, 6H), 2.10 (m, 2H), 1.40 (t, 3H). ES-MS m/z 467 (MH$^+$). Anal. Calc'd. for $C_{27}H_{26}N_6O_2 \cdot 1.15$ TFA$\cdot 0.5H_2O$: C, 58.02; H, 4.65; N, 13.86; F, 10.81, H$_2$O. 1.48. Found: C, 58.34; H, 4.76; N, 13.89: F, 10.72; H$_2$O, 1.58.

EXAMPLE 31

3-[1-[3-hydroxypropyl]-1H-indazol-3-yl]-4-[1-(3-quinolinyl)-1H-indol-3-yl]-1H-pyrrole-2,5-dione (Compound 107)

Following the procedure of Example 1, using 3-bromoquinoline in place of 3-bromopyridine, a 1-(3-quinolinyl)-indol-3-yl glyoxylic methyl ester analog of Compound 1c was prepared. $^1$H NMR (CDCl$_3$) δ 9.15 (d, J=2.3 Hz, 1H), 8.69 (s, 1H), 8.55 (d, J=7.1 Hz, 1H), 8.37 (d, J=2.0 Hz, 1H), 8.28 (d, J=8.5 Hz, 1H), 7.96 (d, J=8.1 Hz, 1H), 7.87 (m, 1H), 7.72 (m, 1H), 7.45 (m, 3H), 3.98 (s, 3H).

The quinolinyl ester (280 mg, 0.85 mmol) and amide Compound 24b (260 mg, 0.75 mmol) were combined in THF (8.0 mL) with 1M potassium t-butoxide in THF (3.0 mL, 3.0 mmol) at 0° C., addition of 12 N HCl gave an orange solid (430 mg). The solid was purified using flash column chromatography, first with an EtOAc system (EtOAc:MeOH; 50:1) and then with a DCM system (DCM:MeOH; 10:1) to afford Compound 107 (220 mg, 57%) as an orange solid. Compound 107 was dissolved in ACN (20 mL) and 0.25 M aqueous HCl (20 mL), then frozen and lyophilized to the hydrochloride salt (220 mg). ES-MS m/z 514 (MH$^+$). $^1$H NMR (DMSO, 300 MHz) δ 9.23 (s, 1H), 8.79 (s, 1H), 8.54 (s, 1H), 8.19 (d, J=8.3 Hz, 2H), 7.90 (m, 1H), 7.75 (m, 3H), 7.63 (d, J=8.3 Hz, 1H), 7.43 (m, 1H), 7.18 (m, 2H), 6.84 (dd, J=7.2, 7.7 Hz, 1H), 6.58 (d, J=8.0 Hz, 1H), 4.42 (m, 2H), 3.25 (m, 2H). 1.74 (m, 2H). Anal. Calcd. for $C_{31}H_{23}N_5O_3 \cdot 1.33HCl \cdot 3.0H_2O$ (513.55/616.09): C, 60.44; H, 4.96; N, 11.36; Cl, 7.65; KF, 8.76. Anal. Found: C. 60.41; H, 4.60; N, 11 08; Cl, 7.86; KF, 7.45.

EXAMPLE 32

3-(1-benzo[b]thien-3-yl-1H-indol-3-yl)-4-[1-[3-(amino)propyl]-1H-indazol-3-yl]-1H-pyrrole-2,5-dione (Compound 108)

Indazole Compound 1e (1.50 g, 8.6 mmol) in DMF (34 mL) was combined with 1-3-bromopropyl)-2,2,5,5-tetramethyl-1-aza-2,5-disilacyclopentane (3.64 g, 10.0 mmol) and cesium carbonate (4.77, 14.6 mmol) and then placed in an oil bath at 65° C. for 2 h. After cooling to rt, the reaction was filtered, evaporated in vacuo and purified by flash column chromatography (88:10:2; DCM:MeOH:NH$_4$OH) to afford Compound 32a (0.70 g, 35%) as a pale yellow solid. $^1$H NMR (CD$_3$OD) δ 7.75 (d, J=8.2 Hz, 1H), 7.54 (d, J=8.5 Hz, 1H), 7.43–7.38 (m, 1H), 7.14 (t, J=7.2, 7.7 Hz, 1H), 4.46 (t, J=6.7 Hz, 2H), 3.89 (s, 2H), 2.85–2.62 (m, 2H), 2.10–2.01 (m, 2H). ES-MS m/z 233 (MH$^+$).

The 1-(3-benzo[b]thienyl)-indol-3-yl glyoxylic methyl ester analog of Compound 1c (prepared in Example 20) (302 mg, 0.90 mmol) and amide Compound 32a (150 mg, 0.64 mmol) were combined in dry THF (6 mL) under nitrogen and cooled in an ice bath as 1M potassium t-butoxide in THF (2.6 mL, 2.6 mmol) was added with stirring over a 10 min period. After 2 h, the reaction was quenched in an ice bath, 12N HCl (3.2 mL) was slowly added and the mixture was stirred for 10 min. The reaction was diluted with ethyl acetate (150 mL), washed with water (2×32 mL), saturated NaHCO3 (55 mL) and brine (55 mL), then dried (Na$_2$SO$_4$) and evaporated in vacuo to a solid. The solid was purified by flash column chromatography (95:3:2; DCM:MeOH: NH$_4$OH) to afford a red solid Compound 108 (0.047 g, 14%). The product was dissolved in 1N HCl/CH$_3$CN (2:1), then frozen and lyophilized to give the hydrochloride salt of Compound 108. For Compound 108: $^1$H NMR (free base, CDCl$_3$) δ 8.29 (s, 1H), 7.95 (d, J=8.0 Hz, 1H), 7.75 (d, J=8.2 Hz, 1H), 7.62 (s, 1H), 7.51–7.38 (m, 5H), 7.26–7.06 (m, 3H), 6.82 (t, J=7.16, 7.92 Hz, 1H), 6.62 (d, J=8.03 Hz, 1H), 4.42 (t, J=6.72 Hz, 2H), 2.54 (t, J=6.79, 6.75 Hz, 2H), 1.87–1.81 (m, 2H). ES-MS m/z 518 (MH$^+$) Anal. Calcd. for $C_{30}H_{23}N_5O_2S \cdot 1.02HCl \cdot 1.5H_2O$ (517.60/581.83): C, 61.94;

H, 4.69; N, 12.04; Cl, 6.22; KF, 4.65. Found: C, 61.97; H, 4.37; N, 11.95; Cl, 6.23; KF, 4.69.

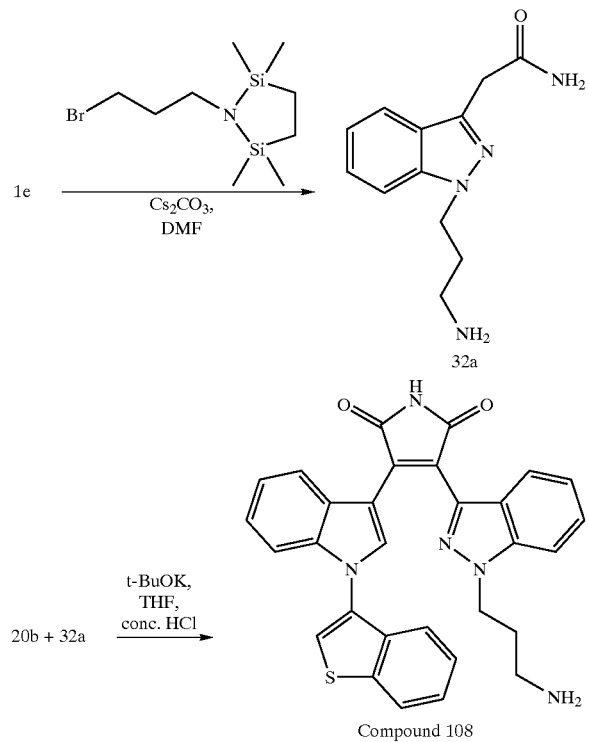

Using the procedure of Example 32 and the appropriate reagents and starting materials known to those skilled in the art, other compounds of the present invention may be prepared including, but not limited to:

| Cpd | Name | ES-MS m/z (MH+) |
|---|---|---|
| 115 | [3-[3-[2,5-dihydro-2,5-dioxo-4-[1-(3-pyridinyl)-1H-indol-3-yl]-1H-pyrrol-3-yl]-1H-indazol-1-yl]propyl]-carbamic acid 1,1-dimethylethyl ester | 563 |

EXAMPLE 33

3-[1-(3-aminopropyl)-1H-indazol-3-yl]-4-[1-(3-pyridinyl)-1H-indol-3-yl]-1H-pyrrole-2,5-dione (Compound 109)

The ester Compound 1c (336 mg, 1.2 mmol) and amide Compound 32a (prepared in Example 32) (200 mg, 0.86 mmol) were combined in dry THF (8 mL) under nitrogen and cooled in an ice bath as 1M potassium t-butoxide in THF (3.4 mL, 3.4 mmol) was added with stirring over a 15 min period. After 1 h, the reaction was warmed to rt. After 2 h, the reaction was quenched in an ice bath. 12N HCl (4.3 mL) was slowly added and the mixture was stirred for 10 min. The reaction was diluted with ethyl acetate (200 mL) and washed with water (2×43 mL), saturated NaHCO3 (74 mL) and brine (74 mL), then dried ($Na_2SO_4$) and evaporated in vacuo to a solid. The solid was purified by flash (column chromatography (93:5:2; DCM:MeOH:$NH_4OH$) to afford Compound 109 (0.041 g, 10%) as a red solid. Compound 109 was dissolved in 1N HCl:$CH_3CN$ (2:1), then frozen and lyophilized give the hydrochloride salt $^1H$ NMR (free base, $CDCl_3$) δ 8.89 (s, 1H), 8.70 (d, J=4.7 Hz, 1H), 8.25 (s, 1H), 7.91 (d, J=8.2 Hz, 1H), 7.80 (d, J=8.2 Hz, 1H), 7.55–7.39 (m, 4H), 7.28–7.12 (m, 2H), 6.80 (t, J=7.9, 7.2 Hz, 1H), 6.50 (d, J=8.0 Hz, 1H), 4.4 (t, J=6.1 Hz, 2H), 2.55 (t, J=6.74 Hz, 2H), 1.79 (t, J=6.73, 6.78 Hz. 2H). ES-MS m/z 463 (MH+). Anal. Calcd. for $C_{27}H_{22}N_6O_2$.2.23HCl.3.0$H_2O$ (462.50/597.87): C, 54.25; H, 5.10; N, 14.06; Cl, 13.23; KF, 9.04. Found: C, 54.25; H, 5.06; N, 13.86; Cl, 13.46, KF, 9.29.

EXAMPLE 34

1H-indazole-1-propanal, 3-[2,5-dihydro-2,5-dioxo-4-[1-(3-pyridinyl)-1H-indol-3-yl]-1H-pyrrol-3-yl]-1H-pyrrole-2,5-dione (Compound 112);

1H-indazole-1-propanoic acid, 3-[2,5-dihydro-2,5-dioxo-4-[1-(3-pyridinyl)-1H-indol-3-yl]-1H-pyrrol-3-yl]-1H-pyrrole-2,5-dione (Compound 113)

Dess-Martin reagent (0.34 g, 0.80 mmol) was added to Compound 94 (prepared in Example 28) (0.31 g, 0.664 mmol) in $CH_2Cl_2$ (12 mL). The mixture was stirred at rt for 3 h, then another portion of Dess-Martin reagent (50 mg, 0.12 mmol) was added and the mixture was stirred for 1 h until TLC showed that Compound 94 was no longer present. The reaction was quenched with 25% $Na_2S_2O_3$ in water (3 mL). The aqueous layer was extracted with chloroform several times. The organic layers were combined and washed with water and brine, then dried ($Na_2SO_4$) and evaporated in vacuo to a reddish solid. The solid was purified by flash column chromatography (95:5:0.5; DCM:MeOH:$NH_4OH$) to afford Compound 112 (300 mg, 98%) as a red solid. $^1H$ NMR ($CD_3OD$) δ 9.43 (s, 1H), 8.84 (d, J=2.4 Hz, 1H), 8.65 (d, J=4.8 Hz, 1H), 8.26 (s, 1H), 8.12 (m, 1H), 7.70 (m, 1H), 7.61 (m, 2H), 7.43 (m, 2H), 7.14 (m, 2H), 6.75 (t, J=7.5 Hz, 1H), 6.43 (d, J=8.1 Hz, 1H), 4.46 (t, J=6.9 Hz, 2H), 1.96 (m, 2H). ES-MS m/z 462 (MH+).

A small amount of crude Compound 113 (4 mg) was also isolated from the column (using 75:20:5; DCM:MeOH:HOAc). Compound 113 was further purified by preparative TLC (95:5:0.5; DCM:MeOH:AcOH). $^1H$ NMR (DMSO) δ 8.90 (d, J=2.3 Hz, 1H), 8.70 (m, 1H), 8.41 (s, 1H), 8.14 (m, 1H), 7.67 (m, 2H), 7.49 (d, J=8.3 Hz, 1H), 7.29 (m, 2H), 7.14 (m, 2H), 6.85 (t, J=7.6 Hz, 1H), 8.56 (d, J=8.1 Hz, 1H), 4.54 (t, J=6.9 Hz, 2H), 2.58 (t, J=6.9 Hz, 2H). ES-MS m/z 478 (MH+).

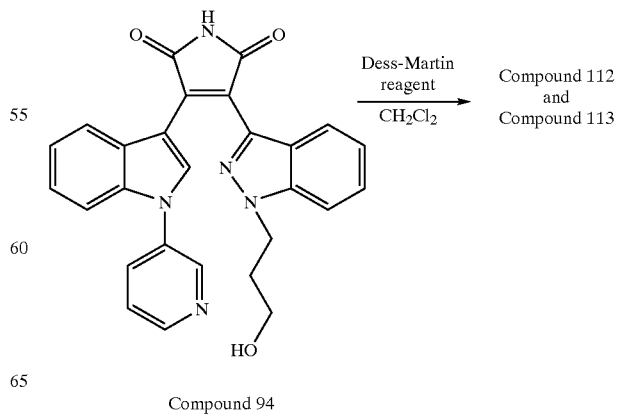

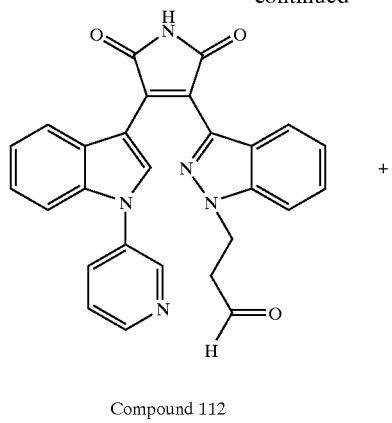

Compound 112

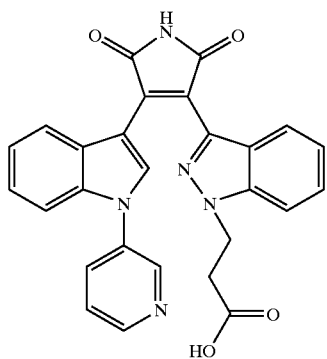

Compound 113

Using the procedure of Example 34 and the appropriate reagents and starting materials known to those skilled in the art, other compounds of the present invention may be prepared including, but not limited to:

| Cpd | Name | ES-MS m/z (MH+) |
|-----|------|-----------------|
| 116 | 3-[4-(1-benzo[b]thien-3-yl-1H-indol-3-yl)-2,5-dihydro-2,5-dioxo-1H-pyrrol-3-yl]-1H-indazole-1-propanoic acid methyl ester | 547 |

EXAMPLE 35

3-[1-(3-methoxypropyl)-1H-indazol-3-yl]-4-[1-(3-pyridinyl)-1H-indol-3-yl]-1H-pyrrole-2,5-dione (Compound 117)

Following the procedure for converting Compound 1e to Compound 1f, the indazole amide Compound 1e (0.31 g, 17.8 mmol) was treated with 1-bromo-3-methoxypropane (0.3 g, 19.6 mmol) in the presence of 95% NaH (0.05 g, 19.6 mmol) in DMF (50 mL) at 0° C. for 20 min and then warmed to 60° C. for 2 h. The mixture was cooled down to rt. Water was added and the aqueous solution was extracted with EtOAc several times. The organic layers were combined and washed with brine, then dried (Na$_2$SO$_4$) and evaporated in vacuo to an oil. The oil was purified by flash column chromatography (96:4:0.4; DCM:MeOH:NH$_4$OH) to afford a 3-methoxypropyl indazole amide analog of Compound 1f (0.32 g, 73%). $^1$H NMR (CDCl$_3$) δ 7.69 (d, J=8.13 Hz, 1H), 7.4 (m, 2H), 7.17 (m, 1H), 6.57 (bd s, 1H), 5.39 (bd s, 1H), 4.47 (t, J=6.65 Hz, 2H), 3.96 (s, 2H), 3.30 (t, J=5.78 Hz, 2H), 3.28 (s, 3H), 2.16 (m, 2H). ES-MS m/z 248 (MH+).

The ester Compound 1c (0.17 g, 0.61 mmol) and the 3-methoxypropyl indazole amide (0.1 g, 0.4 mmol) were combined in dry THF (6 mL) under argon and cooled in an ice bath as 1M potassium t-butoxide in THF (2 mL, 2 mmol) was added with stirring over a 5 min period. After 40 min, the reaction was quenched in an ice bath, 12 N HCl (2 mL, 24 mmol) was slowly added over a 2 min period. The mixture was stirred for 5 min and then made basic to slightly basic by addition of 3N NaOH and extracted with EtOAc. The organic layers were combined and washed with saturated NaHCO$_3$ and brine, then dried (Na$_2$SO$_4$) and evaporated in vacuo to a flaky solid. The solid was purified by flash column chromatography (96:4:0.4; DCM:MeOH:NH$_4$OH) to afford Compound 117 (70 mg, 36%) as an orange flaky solid. Compound 117 was (dissolved in excess dilute HCl, then frozen and lyophilized to give the hydrochloride salt. $^1$H NMR (CD$_3$OD) δ 9.31 (s, 1H), 8.90 (m, 2H), 8.36 (s, 1H), 8.24 (m, 1H), 7.73 (d, J=8.2 Hz, 1H), 7.64 (d, J=8.4 Hz, 1H), 7.59 (d, J=8.5 Hz, 1H), 7.42 (t, J=7.1 Hz, 1H), 7.20 (t, J=7.6 Hz, 1H), 7.12 (t, J=7.4 Hz, 1H), 6.78 (t, J=7.7 Hz, 1H), 6.41 (d, J=8.1 Hz, 1H), 4.40 (t, J=6.6 Hz, 2H), 3.22 (s, 3H), 3.13 (t, J=5.9 Hz, 2H), 1.83 (m, 2H). ES-MS m/z 478 (MH+).

EXAMPLE 36

3-(1H-indazol-3-yl)-4-[1-(3-pyridinyl)-1H-indol-3-yl]-1H-pyrrole-2,5-dione (Compound 118)

The ester Compound 1c (0.22 g, 0.8 mmol) and amide Compound 1e (0.1 g, 0.57 mmol) were combined in dry THF (5 mL) under argon and cooled in an ice bath as 1M potassium t-butoxide in THF (2.9 mL, 2.9 mmol) was added with stirring over a 5 min period. After 40 min, the reaction was quenched in an ice bath, 12 N HCl (2 mL, 24 mmol) was slowly added over a 5 min period. The mixture was stirred for 10 min and then made basic to slightly basic by addition of 3N NaOH and extracted with EtOAc. The organic layers were combined and wash with saturated NaHCO$_3$ and brine, then dried (Na$_2$SO$_4$) and evaporated in vacuo to a flaky solid. The solid was purified by flash column chromatography (96:6:0.6; DCM:MeOH:NH$_4$OH) to afford Compound 118 (70 mg, 30%) as an orange flaky solid. Compound 118 was dissolved in excess dilute HCl, then frozen and lyophilized to give the hydrochloride salt. $^1$H NMR (CD$_3$OD) δ 9.3 (s. 1H). 8.88 (m, 2H), 8.35 (s, 1H), 8.25 (m, 1H), 7.59 (m, 3H), 7.37 (t, J=6.9 Hz, 1H), 7.19 (t, J=7.9 Hz, 1H), 7.05 (t, J=7.8 Hz, 1H), 6.78 (t, J=7.8 Hz, 1H), 6.45 (d, J=7.8 Hz, 1H). ES-MS m/z 406 (MH+).

Using the procedure of Example 36 and the appropriate reagents and starting materials known to those skilled in the art, other compounds of the present invention may be prepared including, but not limited to:

| Cpd | Name | ES-MS m/z (MH+) |
|-----|------|-----------------|
| 104 | 3-(1-(benzo[b]thien-3-yl-1H-indol-3-yl)-4-(1H-indazol-3-yl)-1H-pyrrole-2,5-dione | 461 |

EXAMPLE 37

3-(6-chloro-1-ethyl-1H-indol-3-yl)-4-[1-[3-(dimethylamino)propyl]-1H-indazol-3-yl]-1H-pyrrole-2,5-dione (Compound 90)

Following the procedure of Example 4, using 6-chloroindole in place of 5-chloroindole 6-chloroindole (10.5 g, 0.069 mole) in a mixture with ether (150 mL) was cooled in an ice bath and treated dropwise with oxalyl chloride (9.2 g, 0.072 mole) while stirring under argon. The resulting yellow slurry was stirred at 5° C. for 4 h then cooled to −65° C. Anhydrous methanol (25 mL) was added dropwise to the cold mixture over a 30 min period, then the mixture was allowed to warm to rt and was stirred for 4 h. The resulting suspension of yellow solid was filtered and the solid washed with ether and air-dried to give a 6-chloroindole methyl ester analog of Compound 4b (15.8 g). The crude product was used in the next step without further purification.

Following the procedure of Example 7, a mixture of the 6-chloroindole methyl ester (3.0 g, 0.013 mole) and cesium carbonate (8.5 g, 0.026 mole) in anhydrous DMF (75 mL) was stirred at 30° C. under argon for 1 h. Iodoethane (9.8 g, 0.063 mole) was then added dropwise and stirring continued at 25–30° C. overnight. The reaction mixture was then diluted with ether (1 L) and partitioned with water (100 mL). The organic layer was separated and the aqueous layer extracted with ether (100 mL). The combined organic layers were washed with brine, then dried over anhydrous sodium sulfate and concentrated in vacuo to give a N-ethyl substituted 6-chloroindole methyl ester analog of Compound 7a (3.5 g, 100%) as a white solid. The solid was used in the next step without further purification.

A mixture of Compound 1f (see Example 1) (170 mg, 0.65 mmol) and the N-ethyl substituted 6-chloroindole methyl ester (207 mg, 0.78 mmol) in anhydrous THF (6 mL) was stirred in an ice bath under argon. Then a 1N solution of potassium t-butoxide (2.6 mL) in THF was added dropwise while stirring under argon. The mixture was stirred for an additional 2.5 h at rt, then cooled in an ice bath and quenched with concentrated hydrochloric acid (1.5 mL). The mixture was stirred for 15 min then partitioned with a chloroform and saturated sodium bicarbonate solution. The chloroform layer was washed with brine, then dried over anhydrous sodium sulfate and concentrated in vacuo to give an orange glass. The orange glass was purified via reverse-phase HPLC using a gradient of 30%-90% acetonitrile/water (containing 0.2% TFA) to elute the product as a TFA salt. The salt was freeze-dried to give Compound 90 (45 mg) as a fluffy orange solid. $^1$H NMR (DMSO-d$_6$) δ 8.25 (s, 1H), 7.75 (d, 1H), 7.70 (s, 1H), 7.60 (d, 1H), 7.40 (t, 1H), 7.15 (t, 1H), 6.75 (d, 1H), 6.25 (d, 1H), 4.45 (t, 2H), 4.30 (q, 2H), 3.05 (m, 2H), 2.70 (2s, 6H), 2.00 (m, 2H), 1.35 (t, 3H). ES-MS m/z 476 (MH$^+$). Anal. Calc'd. for C$_{26}$H$_{26}$ClN$_5$O$_2$·1.0 TFA·0.7H$_2$O: C, 55.81; H, 4.75; N, 11.62; F, 9.46, H$_2$O, 2.09. Found: C, 55.40; H, 4.51; N, 11.48; F, 9.66; H$_2$O, 1.48.

EXAMPLE 38

4-[1-[3-(dimethylamino)propyl]-1H-indazol-3-yl]-1, 5-dihydro-3-[1-(3-pyridinyl)-1H-indol-3-yl]-2H-pyrrol-2-one (Compound 125)

The amide compound 1f (1.04 g, 4.0 mmol) and Lawesson's reagent (2,4-bis(4-methoxyphenyl)-1,3-dithia-2,4-diphosphetane-2,4-disulfide) (0.97 g, 2.4 mmol) in dioxane (20 mL) was stirred at rt for 40 h. Additional Lawesson's reagent (0.97 g, 2.4 mmol) was added and the mixture was stirred for another 3 h. The reaction was evaporated to an oil and purified by flash column chromatography (EtOAc:MeOH:NH$_4$OH; 40:8:1) to give a thioamide Compound 38a (0.98 g, 89%) as a white solid. ES-MS m/z 277 (M$^+$). $^1$H NMR (CDCl$_3$) δ 7.73 (d, J=8.2 Hz, 1H), 7.45 (m, 2H), 7.17 (m, 1H), 4.48 (s, 2H), 4.42 (dd, J=6.8, 6.8 Hz, 2H), 2.24 (m, 2H), 2.20 (s, 6H), 2.06 (m, 2H).

Following the procedure of Example 1, the ester Compound 1c (1.1 g, 3.90 mmol) and the thioamide Compound 38a (0.90 g, 3.26 mmol) were combined with 1M potassium t-butoxide in THF (12.8 mL, 12.8 mmol) in THF (30 mL) to afford a thiomaleimide Compound 38b as a red-orange flaky solid (1.95 g). Compound 38b was dissolved in THF (50 mL) and ethanol (20 mL) and Raney nickel (20 g) was added in portions, after washing first with ethanol, and the mixture was stirred for another 30 min. The solution was decanted and evaporated in vacuo to afford Compound 125 as a light orange solid. Compound 125 was purified by flash column chromatography (DCM:MeOH:NH$_4$OH; 80:8:1) to afford a light orange solid (0.28 g, 18%) that was dissolved in aqueous HCl, then frozen and lyophilized. ES-MS m/z 477 (M$^+$). $^1$H NMR (DMSO) δ 8.76 (d, J=1.4 Hz, 1H), 8.61 (dd, J=1.5, 4.9 Hz, 1H), 7.83 (m, 1H), 7.72 (s, 1H), 7.48 (m, 3H), 7.15 (m, 3H), 6.90 (m, 2H), 6.76 (dd, J=7.1, 7.4 Hz, 1H), 6.43 (s, 1H), 4.68 (s, 2H), 4.45 (dd, J=6.8, 6.8 Hz, 2H), 2.23 (m, 2H), 2.20 (s, 6H), 2.04 (m, 2H).

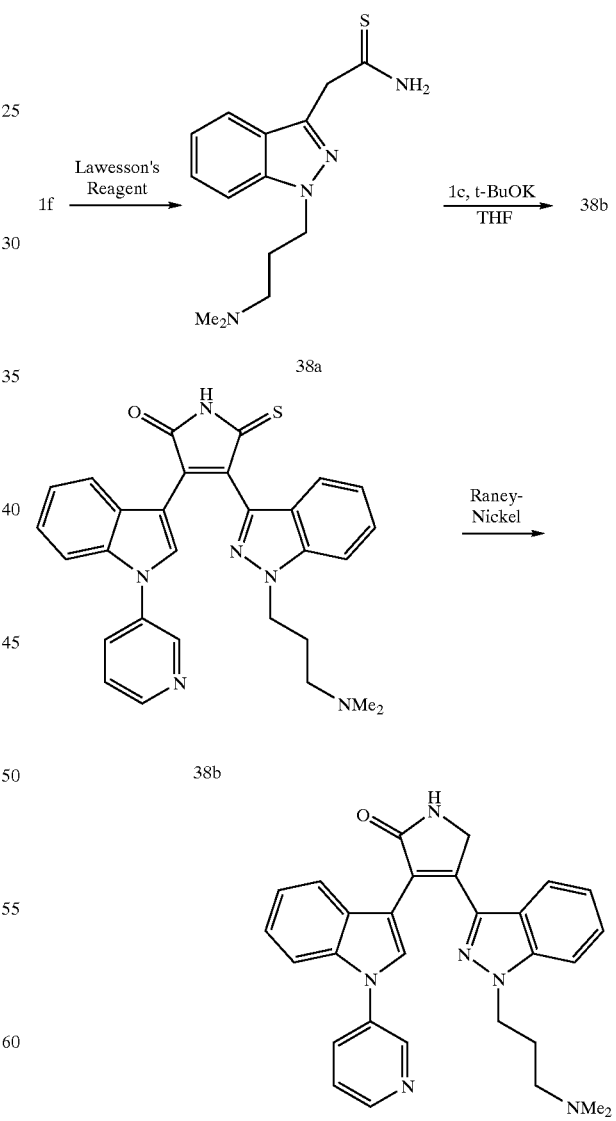

Compound 125

EXAMPLE 39

As a specific embodiment of an oral composition. 100 mg of Compound 14 is formulated with sufficient finely divided lactose to provide a total amount of 580 to 590 mg to fill a size O hard gel capsule.

Biological Experimental Examples

The utility of the compounds to treat kinase or dual-kinase mediated disorders (in particular, kinases selected from protein kinase C and glycogen synthase kinase-3; and, more particularly, kinases selected from protein kinase C α, protein kinase C β-II, protein kinase C γ or glycogen synthase kinase-3β) was determined using the following procedures.

EXAMPLE 1

Protein Kinase C Histone-Based Assay

Compounds were evaluated for PKC selectivity using histone III as the substrate. The PKC isoforms α, β-II or γ were added to a reaction mixture that contained 20 mM HEPES, (pH 7.4), 940 μM $CaCl_2$, 10 mM $MgCl_2$, 1 mM EGTA. 100 μg/mL phosphatidylserine, 20 μg/mL diacylglycerol, 30 μM ATP, 1 μCi ($^{33}$P)ATP and 200 μg/mL histone III. The reaction was incubated for 10 min at 30° C. Reactions were terminated by TCA precipitation and spotting on Whatman P81 filters. Filters were washed in 75 mM phosphoric acid and the radioactivity quantified by liquid scintillation counting.

Table 1 shows the biological activity in the histone based assay as $IC_{50}$ values (μM) for representative compounds of the present invention.

TABLE 1

PKC Activity ($IC_{50}$ μM, Histone Based Assay)

| Cpd | Beta II | Alpha | Gamma |
|---|---|---|---|
| 1 | 0.014 | 0.052 | 0.058 |
| 3 | 0.023 | 0.248 | 0.323 |
| 6 | 0.013 | 0.105 | 0.129 |
| 9 | 0.008 | 0.141 | 0.262 |
| 12 | 0.007 | 0.124 | 0.213 |
| 13 | 0.004 | 0.011 | 0.045 |
| 14 | 0.005 | 0.057 | 0.115 |
| 15 | 0.029 | 1.228 | 3.354 |
| 16 | 0.015 | 0.290 | 0.253 |
| 19 | 0.004 | 0.011 | 0.047 |
| 22 | 0.006 | 0.043 | 0.090 |
| 23 | 0.054 | 0.546 | 0.188 |
| 24 | 0.029 | 0.200 | 1.290 |
| 31 | 0.015 | 0.106 | 0.091 |
| 34 | 0.009 | 0.205 | 0.665 |
| 45 | 0.010 | 0.071 | 0.168 |
| 46 | 0.005 | 0.308 | 0.123 |
| 60 | 0.037 | 0.611 | 0.713 |
| 64 | 0.013 | 0.101 | 0.215 |
| 67 | 0.016 | 1.483 | 0.650 |
| 68 | 0.011 | 0.217 | 0.426 |
| 69 | 0.014 | 0.250 | 0.550 |
| 70 | 0.018 | 0.259 | 0.342 |
| 75 | 0.010 | 0.204 | 0.175 |
| 77 | 0.046 | 0.354 | 0.890 |
| 78 | 0.016 | 0.940 | 0.530 |
| 79 | 0.007 | 0.065 | 0.074 |
| 80 | 0.018 | 0.328 | 0.512 |
| 84 | 0.057 | 0.358 | 0.206 |
| 85 | 0.044 | 0.477 | 0.511 |
| 88 | 0.038 | 0.422 | 0.232 |
| 94 | 0.011 | 0.306 | 0.411 |

TABLE 1-continued

PKC Activity ($IC_{50}$ μM, Histone Based Assay)

| Cpd | Beta II | Alpha | Gamma |
|---|---|---|---|
| 101 | 0.019 | 0.080 | 0.134 |
| 103 | 0.020 | 0.189 | 0.161 |
| 107 | 0.009 | 0.098 | 0.018 |
| 109 | 0.005 | 0.032 | 0.231 |
| 114 | 0.004 | 0.047 | 0.038 |
| 117 | 0.034 | — | — |
| 123 | 0.026 | — | — |
| 125 | 0.005 | 0.339 | — |

EXAMPLE 2

Glycogen Synthase Kinase-3 Assay

Compounds were tested for the ability to inhibit recombinant rabbit GSK-3β protein using the following protocol. The test compound was added to a reaction mixture containing Protein phosphatase inhibitor-2 (PPI-2) (Calbiochem) (45 ng), rabbit GSK-3β protein (New England Biolabs) (0.75 units) and $^{33}$P-ATP (1 μCi) in 50 mM Tris-HCl (pH 8.0), 10 mM $MgCl_2$, 0.1% BSA, 1 mM DTT and 100 μM Sodium Vanadate. The mixture was reacted for 90 minutes at 30° C. to allow phosphorylation of the PPI-2 protein and then the protein in the reaction was precipitated using 10% TCA. The precipitated protein was collected on filter plates (MultiScreen-DV/Millipore), which were subsequently washed. Finally, the radioactivity was quantified using a TopCount Scintillation Counter (Packard). GSK-3 inhibitory compounds resulted in less phosphorylated PPI-2 and thus a lower radioactive signal in the precipitated protein. Staurosporine or Valproate, known inhibitors of GSK-3β, were used as a positive control for screening.

Table 2 shows the biological activity in the GSK-3β assay as $IC_{50}$ values (μM) for representative compounds of the present invention.

TABLE 2

GSK-3β Assay Activity ($IC_{50}$ μM)

| Cpd | GSK-3β |
|---|---|
| 1 | 0.090 |
| 3 | 0.049 |
| 4 | 0.270 |
| 6 | 0.048 |
| 32 | 0.510 |
| 33 | 0.070 |
| 43 | 0.034 |
| 46 | 0.010 |
| 48 | 0.090 |
| 68 | 0.096 |
| 69 | 0.018 |
| 74 | 0.014 |
| 75 | 0.033 |
| 76 | 0.085 |
| 77 | 0.043 |
| 78 | 0.041 |
| 79 | 0.014 |
| 80 | 0.051 |
| 86 | 0.130 |
| 90 | 0.096 |
| 94 | 0.058 |
| 95 | 0.060 |
| 98 | 0.015 |
| 102 | 0.210 |
| 105 | 0.073 |

TABLE 2-continued

GSK-3β Assay Activity (IC$_{50}$ μM)

| Cpd | GSK-3β |
|---|---|
| 106 | 0.033 |
| 107 | 0.820 |
| 110 | 0.075 |
| 111 | 0.040 |
| 112 | 0.115 |
| 114 | 0.155 |
| 115 | 0.055 |
| 117 | 0.070 |
| 118 | 0.200 |

The results from the foregoing indicate that a compound of the present invention would be expected to be useful in treating or ameliorating a kinase or dual-kinase mediated disorder.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of Formula (I):

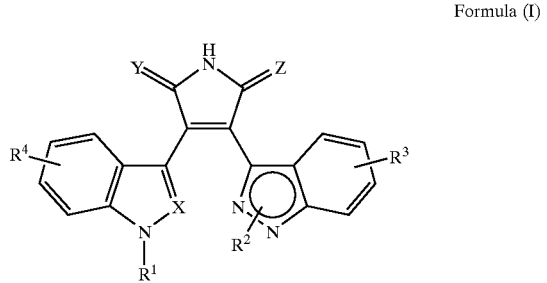

Formula (I)

wherein $R^1$ and $R^2$ are independently selected from the group consisting of:

hydrogen, $C_{1-8}$alkyl, $C_{2-8}$alkenyl, $C_{2-8}$alkynyl {wherein alkyl, alkenyl and alkynyl are optionally substituted with one to two substituents independently selected from the group consisting of —O—($C_{1-8}$)alkyl, —O—($C_{1-8}$)alkyl-OH, —O—($C_{1-8}$)alkyl-O—($C_{1-8}$)alkyl, —O—($C_{1-8}$)alkyl-NH$_2$, —O—($C_{1-8}$)alkyl-NH—($C_{1-8}$)alkyl, —O—($C_{1-8}$)alkyl-N[($C_{1-8}$)alkyl]$_2$, —O—($C_{1-8}$)alkyl-S—($C_{1-8}$)alkyl, —O—($C_{1-8}$)alkyl-SO$_2$—($C_{1-8}$)alkyl, —O—($C_{1-8}$)alkyl-SO$_2$—NH$_2$, —O—($C_{1-8}$)alkyl-SO$_2$—NH—($C_{1-8}$)alkyl, —O—($C_{1-8}$)alkyl-SO$_2$—N[($C_{1-8}$)alkyl]$_2$, —O—C(O)H, —O—C(O)—($C_{1-8}$)alkyl, —O—C(O)—NH$_2$, —O—C(O)—NH—($C_{1-8}$)alkyl, —O—C(O)—N[($C_{1-8}$)alkyl]$_2$, —O—($C_{1-8}$)alkyl-C(O)H, —O—($C_{1-8}$)alkyl-C(O)—($C_{1-8}$)alkyl, —O—($C_{1-8}$)alkyl-CO$_2$H, —O—($C_{1-8}$)alkyl-C(O)—O—($C_{1-8}$)alkyl, —O—($C_{1-8}$)alkyl-C(O)—NH$_2$, —O—($C_{1-8}$)alkyl-C(O)—NH—($C_{1-8}$)alkyl, —O—($C_{1-8}$)alkyl-C(O)—N[($C_{1-8}$)alkyl]$_2$, —C(O)H, —C(O)—($C_{1-8}$)alkyl, —CO$_2$H, —C(O)—O—($C_{1-8}$)alkyl, —C(O)—NH$_2$, —C(NH)—NH$_2$, —C(O)—NH—($C_{1-8}$)alkyl, —C(O)—N[($C_{1-8}$)alkyl]$_2$, —SH, —S—($C_{1-8}$)alkyl, —S—($C_{1-8}$)alkyl-S—($C_{1-8}$)alkyl, —S—($C_{1-8}$)alkyl-O—($C_{1-8}$)alkyl, —S—($C_{1-8}$)alkyl-O—($C_{1-8}$)alkyl-OH, —S—($C_{1-8}$)alkyl-O—($C_{1-8}$)alkyl-NH$_2$, —S—($C_{1-8}$)alkyl-O—($C_{1-8}$)alkyl-NH—($C_{1-8}$)alkyl, —S—($C_{1-8}$)alkyl-O—($C_{1-8}$)alkyl-N[($C_{1-8}$)alkyl]$_2$, —S—($C_{1-8}$)alkyl-NH—($C_{1-8}$)alkyl, —SO$_2$—($C_{1-8}$)alkyl, —SO$_2$—NH$_2$, —SO$_2$—NH—($C_{1-8}$)alkyl, —SO$_2$—N[($C_{1-8}$)alkyl]$_2$, amino (substituted with two substituents independently selected from the group consisting of hydrogen, $C_{1-8}$alkyl, $C_{2-8}$alkenyl, $C_{2-8}$alkynyl, —($C_{1-8}$)alkyl-OH, —($C_{1-8}$)alkyl-O—($C_{1-8}$)alkyl, —($C_{1-8}$)alkyl-NH$_2$, —($C_{1-8}$)alkyl-NH—($C_{1-8}$)alkyl, —($C_{1-8}$)alkyl-N[($C_{1-8}$)alkyl]$_2$, —($C_{1-8}$)alkyl-S—($C_{1-8}$)alkyl, —C(O)—($C_{1-8}$)alkyl, —C(O)—O—($C_{1-8}$)alkyl, —C(O)—NH$_2$, —C(O)—NH—($C_{1-8}$)alkyl, —C(O)—N[($C_{1-8}$)alkyl]$_2$, —SO$_2$—($C_{1-8}$)alkyl, —SO$_2$—NH$_2$, —SO$_2$—NH—($C_{1-8}$)alkyl, —SO$_2$—N[($C_{1-8}$)alkyl]$_2$, —C(N)—NH$_2$, aryl and aryl($C_{1-8}$)alkyl (wherein aryl is optionally substituted with one to three substituents independently selected from the group consisting of halogen, $C_{1-8}$alkyl, $C_{1-8}$alkoxy, amino (substituted with two substituents selected from the group consisting of hydrogen and $C_{1-8}$alkyl), cyano, halo, (halo)$_{1-3}$($C_{1-8}$)alkyl, (halo)$_{1-3}$($C_{1-8}$)alkoxy, hydroxy, hydroxy($C_{1-8}$)alkyl and nitro)), cyano, (halo)$_{1-3}$, hydroxy, nitro, oxo, and aryl is optionally substituted with one to three substituents independently selected from the group consisting of $C_{1-8}$-alkyl, $C_{1-8}$alkoxy, amino (substituted with two substituents selected from the group consisting of hydrogen and $C_{1-8}$-alkyl), cyano, halo, (halo)$_{1-3}$ ($C_{1-8}$)alkyl, (halo)$_{1-3}$ ($C_{1-8}$)alkoxy, hydroxy, hydroxy($C_{1-8}$)alkyl and nitro)}, —C(O)—($C_{1-8}$)alkyl, —C(O)-aryl, —C(O)—O—($C_{1-8}$)alkyl, —C(O)—O-aryl, —C(O)—NH—($C_{1-8}$)alkyl, —C(O)—NH-aryl, —C(O)—N[($C_{1-8}$)alkyl]$_2$, —SO$_2$—($C_{1-8}$)alkyl, —SO$_2$-aryl, aryl, pyridinyl, quinolinyl and isoquinolinyl {wherein auyl, pyridinyl, quinolinyl and isoquinolinyl are optionally substituted with one to three substituents independently selected from the group consisting of $C_{1-8}$alkyl, $C_{2-8}$alkenyl, $C_{2-8}$alkynyl, $C_{1-8}$alkoxy, —C(O)H, —C(O)—($C_{1-8}$)alkyl, —CO$_2$H, —C(O)—O—($C_{1-8}$)alkyl, —C(O)—NH$_2$, —C(NH)—NH$_2$, —C(O)—NH-($C_{1-8}$)alkyl, —C(O)—N[($C_{1-8}$)alkyl]$_2$, —SH, —S—($C_{1-8}$)alkyl, —SO$_2$—($C_{1-8}$)alkyl, —SO$_2$—NH$_2$, —SO$_2$—NH—($C_{1-8}$)alkyl, —SO$_2$—N[($C_{1-8}$)alkyl]$_2$, amino (substituted with two substituents independently selected from the group consisting of hydrogen, $C_{1-8}$alkyl, $C_{2-8}$alkenyl, $C_{2-8}$alkynyl, —($C_{1-8}$)alkyl-NH$_2$, —C(O)—($C_{1-8}$)alkyl, —C(O)—O—($C_{1-8}$)alkyl, —C(O)—NH$_2$, —C(O)—NH—($C_{1-8}$)alkyl, —C(O)—N[($C_{1-8}$)alkyl]$_2$, —SO$_2$—($C_{1-8}$)alkyl, —SO$_2$—NH$_2$, —SO$_2$NH—($C_{1-8}$)alkyl, —SO$_2$—N[($C_{1-8}$)alkyl]$_2$ and —C(NH)—NH$_2$), amino-($C_{1-8}$)alkyl-(wherein amino is substituted with two substituents independently selected from the group consisting of hydrogen, $C_{1-8}$alkyl, $C_{2-8}$alkenyl, $C_{2-8}$alkynyl, —($C_{1-8}$)alkyl-NH$_2$, —C(O)—($C_{1-8}$)alkyl, —C(O)—O—($C_{1-8}$)alkyl, —C(O)—NH$_2$, —C(O)—NH—($C_{1-8}$)alkyl, —C(O)—N[($C_{1-8}$)alkyl]$_2$, —SO$_2$—($C_{1-8}$)alkyl, —SO$_2$—NH$_2$, —SO$_2$—NH—($C_{1-8}$)alkyl, —SO$_2$—N[($C_{1-8}$)alkyl]$_2$ and —C(NH)—NH$_2$), cyano, halo, (halo)$_{1-3}$($C_{1-8}$)alkyl-, (halo)$_{1-3}$($C_{1-8}$)alkoxy-, hydroxy, hydroxy($C_{1-8}$)alkyl, nitro, aryl, and —($C_{1-8}$)alkyl-aryl, with the proviso that at least one of $R^1$ and $R^2$ is selected from the group consisting of pyridinyl, quinolinyl and isoquinolinyl;

X is selected from the group consisting of N and $CR^5$;

$R^3$ and $R^4$ are independently selected from the group consisting of hydrogen, $C_{1-8}$alkyl, $C_{2-8}$alkenyl, $C_{2-8}$alkynyl, $C_{1-8}$alkoxy, —C(O)H, —C(O)—($C_{1-8}$)alkyl, —$CO_2$H, —C(O)—O—($C_{1-8}$)alkyl, —C(O)—$NH_2$, —C(NH)—$NH_2$, —C(O)—NH—($C_{1-8}$)alkyl, —C(O)—N[($C_{1-8}$ alkyl]$_2$, —SH, —S—($C_{1-8}$)alkyl, —$SO_2$—($C_{1-8}$)alkyl, —$SO_2$—$NH_2$, —$SO_2$—NH—($C_{1-8}$)alkyl, —$SO_2$—N [($C_{1-8}$)alkyl]$_2$, amino (substituted with two substituents independently selected from the group consisting of hydrogen, $C_{1-8}$alkyl, $C_{2-8}$alkenyl, $C_{2-8}$alkynyl, —($C_{1-8}$) alkyl-$NH_2$, —C(O)—($C_{1-8}$)alkyl, —C(O)—O—($C_{1-8}$) alkyl, —C(O)—$NH_2$, —C(O)—NH—($C_{1-8}$)alkyl, —C(O)—N[($C_{1-8}$)alkyl]$_2$, —$SO_2$—($C_{1-8}$)alkyl, —$SO_2$—$NH_2$, —$SO_2$—NH—($C_{-18}$)alkyl, —$SO_2$—N[($C_{1-8}$) alkyl]$_2$ and —C(NH)—$NH_2$), amino-($C_{1-8}$)alkyl- (wherein amino is substituted with two substituents independently selected from the group consisting of hydrogen, $C_{1-8}$alkyl, $C_{2-8}$alkenyl, $C_{2-8}$alkynyl, —($C_{1-8}$) alkyl-$NH_2$, —C(O)—($C_{1-8}$)alkyl, —C(O)—O—($C_{1-8}$) alkyl, —C(O)—$NH_2$, —C(O)—NH—($C_{1-8}$)alkyl, —C(O)—N[($C_{1-8}$)alkyl]$_2$, —$SO_2$—($C_{1-8}$)alkyl, —$SO_2$—$NH_2$, —$SO_2$—NH—($C_{1-8}$)alkyl, —$SO_2$—N[($C_{1-8}$) alkyl]$_2$ and —C(NH)—$NH_2$), cyano, halo, (halo)$_{1-3}$($C_{1-8}$) alkyl-, (halo)$_{1-3}$($C_{1-8}$)alkoxy-, hydroxy, hydroxy($C_{1-8}$) alkyl-, nitro, aryl, and —($C_{1-8}$)alkyl-aryl;

Y and Z are independently selected from the group consisting of O, S, (H,OH) and (H,H); with the proviso that one of Y and Z is O and the other is selected from the group consisting of O, S, (H,OH) and (H,H); and, $R^5$ is selected from the group consisting of:

hydrogen, halogen, $C_{1-8}$alkyl, $C_{2-8}$alkenyl, $C_{2-8}$alkynyl {wherein alkyl, alkenyl and alkynyl are optionally substituted with one to two substituents independently selected from the group consisting of amino (substituted with two substituents selected from the group consisting of hydrogen and $C_{1-8}$alkyl), cyano, halo, hydroxy, nitro, oxo, and aryl}, and aryl and heteroaryl {wherein aryl and heteroaryl are optionally substituted with one to two substituents independently selected from the group consisting of $C_{1-8}$alkyl, $C_{1-8}$alkoxy, amino (substituted with two substituents selected from the group consisting of hydrogen and $C_{1-8}$alkyl), cyano, halo, hydroxy and nitro};

and a pharmaceutically acceptable salt thereof.

2. The compound of claim 1 wherein $R^1$ and $R^2$ are independently selected from the group consisting of:

hydrogen, $C_{1-4}$alkyl, $C_{2-4}$alkenyl, $C_{2-4}$alkynyl {wherein alkyl, alkenyl and alkynyl are optionally substituted with one to two substituents independently selected from the group consisting of —O—($C_{1-4}$)alkyl, —O—($C_{1-4}$)alkyl-OH, —O—($C_{1-4}$)alkyl-O—($C_{1-4}$)alkyl, —O—($C_{1-4}$)alkyl-$NH_2$, —O—($C_{1-4}$)alkyl-NH—($C_{1-4}$)alkyl, —O—($C_{1-4}$) alkyl-N[($C_{1-4}$)alkyl]$_2$, —O—($C_{1-4}$)alkyl-S—($C_{1-4}$)alkyl, —O—($C_{1-4}$)alkyl-$SO_2$—($C_{1-4}$)alkyl, —O—($C_{1-4}$)alkyl-$SO_2$—$NH_2$, —O—($C_{1-4}$)alkyl-$SO_2$—NH—($C_{1-4}$)alkyl, —O—($C_{1-4}$)alkyl-$SO_2$—N[($C_{1-4}$)alkyl]$_2$, —O—C(O)H, —O—C(O)—($C_{1-4}$)alkyl, —O—C(O)—$NH_2$, —O—C(O)—NH—($C_{1-4}$)alkyl, —O—C(O)—N[($C_{1-4}$)alkyl]$_2$, —O—($C_{1-4}$)alkyl-C(O)H, —O—($C_{1-4}$)alkyl-C(O)—($C_{1-4}$)alkyl, —O—($C_{1-4}$)alkyl-$CO_2$H, —O—($C_{1-4}$)alkyl-C(O)—O—($C_{1-4}$)alkyl, —O—($C_{1-4}$)alkyl-C(O)—$NH_2$, —O—($C_{1-4}$)alkyl-C(O)—NH—($C_{1-4}$)alkyl, —O—($C_{1-4}$) alkyl-C(O)—N[($C_{1-4}$)alkyl]$_2$, —C(O)H, —C(O)—($C_{1-4}$) alkyl, —$CO_2$H, —C(O)—O—($C_{1-4}$)alkyl, —C(O)—$NH_2$, —C(NH)—$NH_2$, —C(O)—NH—($C_{1-4}$)alkyl, —C(O)—N[($C_{1-4}$)alkyl]$_2$, —SH, —S—($C_{1-4}$)alkyl, —S—($C_{1-4}$)alkyl-S—($C_{1-4}$)alkyl, —S—($C_{1-4}$)alkyl-O—($C_{1-4}$)alkyl, —S—($C_{1-4}$)alkyl-O—($C_{1-4}$)alkyl-OH, —S—($C_{1-4}$)alkyl-O—($C_{1-4}$)alkyl-$NH_2$, —S—($C_{1-4}$)alkyl-O—($C_{1-4}$)alkyl-NH—($C_{1-4}$)alkyl, —S—($C_{1-4}$)alkyl-O—($C_{1-4}$)alkyl-N[($C_{1-4}$)alkyl]$_2$, —S—($C_{1-4}$)alkyl-NH—($C_{1-4}$)alkyl, —$SO_2$—($C_{1-4}$)alkyl, —$SO_2$—$NH_2$, —$SO_2$—NH—($C_{1-4}$)alkyl, —$SO_2$—N[($C_{1-4}$)alkyl]$_2$, amino (substituted with two substituents independently selected from the group consisting of hydrogen, $C_{1-4}$alkyl, $C_{2-4}$alkenyl, $C_{2-4}$alkynyl, —($C_{1-4}$)alkyl-OH, —($C_{1-4}$) alkyl-O—($C_{1-4}$)alkyl, —($C_{1-4}$)alkyl-$NH_2$, —($C_{1-4}$)alkyl-NH—($C_{1-4}$)alkyl, —($C_{1-4}$)alkyl-N[($C_{1-4}$)alkyl]$_2$, —($C_{1-4}$) alkyl-S—($C_{1-4}$)alkyl, —C(O)—($C_{1-4}$)alkyl, —C(O)—O—($C_{1-4}$)alkyl, —C(O)—$NH_2$, —C(O)—NH—($C_{1-4}$) alkyl, —C(O)—N[($C_{1-4}$)alkyl]$_2$, —$SO_2$—($C_{1-4}$)alkyl, —$SO_2$—$NH_2$, —$SO_2$—NH—($C_{1-4}$)alkyl, —$SO_2$—N [($C_{1-4}$)alkyl]$_2$, —C(N)—$NH_2$, aryl pyridinyl, quinolinyl, and isoquinolinyl, and aryl($C_{1-4}$)alkyl (wherein aryl is optionally substituted with one to three substituents independently selected from the group consisting of halogen, $C_{1-4}$alkyl, $C_{1-4}$alkoxy, amino (substituted with two substituents selected from the group consisting of hydrogen and $C_{1-4}$alkyl), cyano, halo, (halo)$_{1-3}$($C_{1-4}$)alkyl, (halo)$_{1-3}$ ($C_{1-4}$)alkoxy, hydroxy, hydroxy($C_{1-4}$)alkyl and nitro)), cyano, (halo)$_{1-3}$, hydroxy, nitro, oxo, heterocyclyl, aryl and heteroaryl (wherein heterocyclyl, aryl and heteroaryl are optionally substituted with one to three substituents independently selected from the group consisting of $C_{1-4}$alkyl, $C_{1-4}$alkoxy, amino (substituted with two substituents selected from the group consisting of hydrogen and $C_{1-4}$alkyl), cyano, halo, (halo)$_{1-3}$($C_{1-4}$)alkyl, (halo)$_{1-3}$ ($C_{1-4}$)alkoxy, hydroxy, hydroxy($C_{1-4}$)alkyl and nitro)}, —C(O)—($C_{1-4}$)alkyl, —C(O)-aryl, —C(O)—O—($C_{1-4}$) alkyl, —C(O)—O-aryl, —C(O)—NH—($C_{1-4}$)alkyl, C(O)—NH-aryl, —C(O)—N[($C_{1-4}$)alkyl]$_2$, —$SO_2$—($C_{1-4}$)alkyl, —$SO_2$-aryl, aryl and heteroaryl {wherein aryl and heteroaryl are optionally substituted with one to three substituents independently selected from the group consisting of $C_{1-4}$alkyl, $C_{2-4}$alkenyl, $C_{2-4}$alkynyl, $C_{1-4}$alkoxy, —C(O)H, —C(O)—($C_{1-4}$)alkyl. —$CO_2$H, —C(O)—O—($C_{1-4}$) alkyl, —C(O)—$NH_2$, —C(NH)—$NH_2$, —C(O)—NH—($C_{1-4}$)alkyl, —C(O)—N[($C_{1-4}$)alkyl]$_2$, —SH, —S—($C_{1-4}$)alkyl, —$SO_2$—($C_{1-4}$)alkyl, —$SO_2$—$NH_2$, —$SO_2$—NH—($C_{1-4}$)alkyl, —$SO_2$—N[($C_{1-4}$)alkyl]$_2$, amino (substituted with two substituents independently selected from the group consisting of hydrogen, $C_{1-4}$alkyl, $C_{2-4}$alkenyl, $C_{2-4}$alkynyl, —($C_{1-4}$)alkyl-$NH_2$, —C(O)—($C_{1-4}$)alkyl, —C(O)—O—($C_{1-4}$)alkyl, —C(O)—$NH_2$, —C(O)—NH—($C_{1-4}$)alkyl, —C(O)—N[($C_{1-4}$)alkyl]$_2$, —$SO_2$—($C_{1-4}$)alkyl, —$SO_2$—$NH_2$, —$SO_2$—NH—($C_{1-4}$) alkyl, —$SO_2$—N[($C_{1-4}$)alkyl]$_2$ and —C(NH)—$NH_2$), amino-($C_{1-4}$)alkyl- (wherein amino is substituted with two substituents independently selected from the group consisting of hydrogen, $C_{1-4}$alkyl, $C_{2-4}$alkenyl, $C_{2-4}$alkynyl, —($C_{1-4}$)alkyl-$NH_2$, —C(O)—($C_{1-4}$)alkyl, —C(O)—O—($C_{1-4}$)alkyl, —C(O)—$NH_2$, —C(O)—NH—($C_{1-4}$)alkyl, —C(O)—N[($C_{1-4}$)alkyl]$_2$, —$SO_2$—($C_{1-4}$)alkyl, —$SO_2$—$NH_2$, —$SO_2$—NH—($C_{1-4}$)alkyl, —$SO_2$—N[($C_{1-4}$)alkyl]$_2$ and —C(NH)—$NH_2$), cyano, halo, (halo)$_{1-3}$($C_{1-4}$)alkyl, (halo)$_{1-3}$($C_{1-4}$)alkoxy, hydroxy, hydroxy($C_{1-4}$)alkyl, nitro, and with the provisio that at least one of $R^1$ and $R^2$ is selected from the group consisting of pyridinyl, quinolinyl and isoquinolinyl.

3. The compound of claim 1 wherein $R^1$ and $R^2$ are independently selected from the group consisting of:

hydrogen, $C_{1-4}$alkyl, $C_{2-4}$alkenyl {wherein alkyl is substituted with one to two substituents independently selected from the group consisting of —O—($C_{1-4}$)alkyl, —O—($C_{1-4}$)alkyl-OH, —O—($C_{1-4}$)alkyl-NH—($C_{1-4}$)alkyl, —O—C(O)—($C_{1-4}$)alkyl, —C(O)H, —CO$_2$H, —C(O)—O—($C_{1-4}$)alkyl, amino (substituted with two substituents independently selected from the group consisting of hydrogen, $C_{1-4}$alkyl, —($C_{1-4}$)alkyl-OH, —C(O)—O—($C_{1-4}$)alkyl and aryl ($C_{1-4}$)alkyl), hydroxy, heterocyclyl, aryl and heteroaryl (wherein heterocyclyl, aryl and heteroaryl are optionally substituted with one to three substituents independently selected from the group consisting of $C_{1-4}$alkyl and halo)}, aryl and heteroaryl {wherein aryl and heteroaryl are optionally substituted with one to two substituents independently selected from the group consisting of $C_{1-4}$alkyl, ($C_{1-4}$alkoxy, amino (substituted with two substituents independently selected from the group consisting of hydrogen and $C_{1-4}$alkyl), cyano, halo, (halo)$_{1-3}$($C_{1-4}$)alkyl, (halo)$_{1-3}$($C_{1-4}$)alkoxy, hydroxy, hydroxy($C_{1-4}$)alkyl, and with the provisio that at least one of $R^1$ and $R^2$ is selected from the group consisting of pyridinyl, quinolinyl and isoquinolinyl.

4. The compound of claim 1 wherein $R^1$ is selected from the group consisting of:

hydrogen, $C_{1-4}$-alkyl, $C_{2-4}$alkenyl {wherein alkyl is substituted with one to two substituents independently selected from the group consisting of —O—($C_{1-4}$)alkyl-NH—($C_{1-4}$)alkyl, amino (substituted with two substituents independently selected from the group consisting of hydrogen and $C_{1-4}$alkyl), hydroxy, heterocyclyl, aryl and heteroaryl (wherein heterocyclyl, aryl and heteroaryl are optionally substituted with one to three substituents independently selected from the group consisting of $C_{1-4}$alkyl and halo)}, aryl and heteroaryl {wherein aryl and heteroaryl are optionally substituted with one to two substituents independently selected from the group consisting of $C_{1-4}$-alkyl, $C_{1-4}$alkoxy, amino (substituted with two substituents independently selected from the group consisting of hydrogen and $C_{1-4}$alkyl), cyano, halo, (halo)$_{1-3}$($C_{1-4}$)alkyl, (halo)$_{1-3}$($C_{1-4}$)alkoxy, hydroxy, hydroxy($C_{1-4}$)alkyl, and aryl.

5. The compound of claim 1 wherein $R^1$ is selected from the group consisting of:

hydrogen, $C_{1-4}$alkyl, $C_{2-3}$alkenyl {wherein alkyl is substituted with one to two substituents independently selected from the group consisting of —O—($C_{1-4}$)alkyl-NH—($C_{1-4}$)alkyl, amino (substituted with two substituents independently selected from the group consisting of hydrogen and $C_{1-4}$alkyl), hydroxy, phenyl, naphthalenyl, (wherein phenyl is optionally substituted with one to two chloro substituents)}, phenyl, naphthalenyl, pyridinyl, quinolinyl and isoquinolinyl (wherein phenyl, naphthalenyl and pyridinyl are optionally substituted with one to two substituents independently selected from the group consisting of $C_{1-4}$alkyl, $C_{1-4}$alkoxy, halo and hydroxy; and, wherein phenyl is optionally substituted with phenyl).

6. The compound of claim 1 wherein $R^2$ is selected from the group consisting of:

hydrogen, $C_{1-4}$alkyl {wherein alkyl is substituted with one to two substituents independently selected from the group consisting of —O—($C_{1-4}$)alkyl, —O—($C_{1-4}$)alkyl-OH, —O—($C_{1-4}$)alkyl-NH—($C_{1-4}$)alkyl, —O—C(O)—($C_{1-4}$)alkyl, —C(O)H, —CO$_2$H, —C(O)—O—($C_{1-4}$)alkyl, amino (substituted with two substituents independently selected from the group consisting of hydrogen, $C_{1-4}$alkyl, —($C_{1-4}$)alkyl-OH, —C(O)—O—($C_{1-4}$)alkyl and aryl ($C_{1-4}$)alkyl), hydroxy}, pyridinyl, quinolinyl and isoquinolinyl.

7. The compound of claim 1 wherein $R^2$ is selected from the group consisting of:

hydrogen, $C_{1-4}$alkyl {wherein alkyl is substituted with one to two substituents independently selected from the group consisting of —O—($C_{1-4}$)alkyl, —O—($C_{1-4}$)alkyl-OH, —O—($C_{1-4}$)alkyl-NH—($C_{1-4}$)alkyl, —O—C(O)—($C_{1-4}$)alkyl, —C(O)H, —CO$_2$H, —C(O)—O—($C_{1-4}$)alkyl, amino (substituted with two substituents independently selected from the group consisting of hydrogen, $C_{1-4}$alkyl, —($C_{1-4}$)alkyl-OH, —C(O)—O—($C_{1-4}$)alkyl and phenyl ($C_{1-4}$)alkyl), hydroxy}, and pyridinyl.

8. The compound of claim 1 wherein X is $CR^5$.

9. The compound of claim 1 wherein $R^3$ and $R^4$ are independently selected from the group consisting of hydrogen, $C_{1-4}$alkyl, $C_{2-4}$alkenyl, $C_{2-4}$alkynyl, $C_{1-4}$alkoxy, —C(O)H, —C(O)—($C_{1-4}$)alkyl, —CO$_2$H, —C(O)—O—($C_{1-4}$)alkyl, —C(O)—NH$_2$, —C(NH)—NH$_2$, —C(O)—NH—($C_{1-4}$)alkyl, —C(O)—N[($C_{1-4}$)alkyl]$_2$, —SH, —S—($C_{1-4}$)alkyl, —SO$_2$—($C_{1-4}$)alkyl, —SO$_2$—NH$_2$, —SO$_2$—NH—($C_{1-4}$)alkyl, —SO$_2$—N[($C_{1-4}$)alkyl]$_2$, amino (substituted with two substituents independently selected from the group consisting of hydrogen, $C_{1-4}$alkyl, $C_{2-4}$alkenyl, $C_{2-4}$alkynyl, —($C_{1-4}$)alkyl-NH$_2$, —C(O)—($C_{1-4}$)alkyl, —C(O)—O—($C_{1-4}$)alkyl, —C(O)—NH$_2$, —C(O)—NH—($C_{1-4}$)alkyl, —C(O)—N[($C_{1-4}$)alkyl]$_2$, —SO$_2$—($C_{1-4}$)alkyl, —SO$_2$—NH$_2$, —SO$_2$—NH—($C_{1-4}$) alkyl, —SO$_2$—N[($C_{1-4}$)alkyl]$_2$ and —C(NH)—NH$_2$), amino-($C_{1-4}$)alkyl- (wherein amino is substituted with two substituents independently selected from the group consisting of hydrogen, $C_{1-4}$alkyl, $C_{2-4}$alkenyl, $C_{2-4}$alkynyl, —($C_{1-4}$)alkyl-NH$_2$, —C(O)—($C_{1-4}$)alkyl, —C(O)—O—($C_{1-4}$)alkyl, —C(O)—NH$_2$, —C(O)—NH—($C_{1-4}$)alkyl, —C(O)—N[($C_{1-4}$)alkyl]$_2$, —SO$_2$—($C_{1-4}$)alkyl, —SO$_2$—NH$_2$, —SO$_2$—NH—($C_{1-4}$)alkyl, —SO$_2$—N[($C_{1-4}$)alkyl]$_2$ and —C(NH)—NH$_2$), cyano, halo, (halo)$_{1-3}$($C_{1-4}$)alkyl, (halo)$_{1-3}$($C_{1-4}$)alkoxy, hydroxy, hydroxy($C_{1-4}$)alkyl, nitro, aryl and —($C_{1-4}$)alkyl-aryl.

10. The compound of claim 1 wherein $R^3$ and $R^4$ are independently selected from the group consisting of hydrogen, $C_{1-4}$alkyl, $C_{1-4}$alkoxy, cyano and halogen.

11. The compound of claim 1 wherein $R^3$ and $R^4$ are independently selected from the group consisting of hydrogen, methyl, methoxy, cyano and chloro.

12. The compound of claim 1 wherein Y is O, and Z is O.

13. The compound of claim 1 wherein Y and Z are independently selected from the group consisting of O and (H,H); with the proviso that one of Y and Z is O, and the other is selected from the group consisting of O and (H,H).

14. The compound of claim 1 wherein $R^5$ is selected from the group consisting of:

hydrogen, halogen,

C$_{1-4}$alkyl, C$_{2-4}$alkenyl, C$_{2-4}$alkynyl {wherein alkyl, alkenyl and alkynyl are optionally substituted with one to two substituents independently selected from the group consisting of amino (substituted with two substituents selected from the group consisting of hydrogen and C$_{1-4}$alkyl), cyano, halo, hydroxy, nitro, oxo, and aryl},
aryl {wherein aryl is optionally substituted with one to two substituents independently selected from the group consisting of C$_{1-4}$alkyl, C$_{1-4}$alkoxy, amino (substituted with two substituents selected from the group consisting of hydrogen and C$_{1-4}$alkyl), cyano, halo, hydroxy and nitro}.

15. The compound of claim 1 wherein R$^5$ is selected from the group consisting of C$_{1-4}$alkyl and aryl.

16. The compound of claim 1 wherein R$^5$ is selected from the group consisting of methyl and naphthalenyl.

17. The compound of claim 1 wherein the compound of Formula (I) is a compound selected from Formula (Ia):

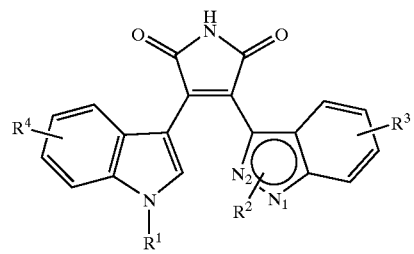

Formula (Ia)

wherein R$^1$, R$^2$, R$^3$ and R$^4$ are dependently selected from the group consisting of:

| R$^1$ | R$^2$ | R$^3$ | R$^4$ |
|---|---|---|---|
| 3-pyridinyl | N1-[Me$_2$NCH$_2$CH(OH)CH$_2$] | H | H; |
| 3-pyridinyl | N1-[MeNHCH$_2$CH(OH)CH$_2$] | H | H; |
| 4-isoquinolinyl | N1-[Me$_2$N(CH$_2$)$_3$] | H | H; |
| 3-pyridinyl | N1-[Me$_2$NCH$_2$CH(OH)CH$_2$] | 5-Cl | H; |
| 3-quinolinyl | N1-[Me$_2$N(CH$_2$)$_3$] | 5-Cl | H; |
| 3-quinolinyl | N1-[Me$_2$N(CH$_2$)$_3$] | H | 5-Cl; |
| 3-quinolinyl | N1-[Me$_2$N(CH$_2$)$_3$] | H | H; |
| 3-quinolinyl | N1-[Me$_2$N(CH$_2$)$_3$] | H | H; |
| 3-pyridinyl | N1-[Me$_2$N(CH$_2$)$_3$] | H | H; |
| 3-pyridinyl-CH$_2$ | N1-[Me$_2$N(CH$_2$)$_3$] | H | 4-Cl; |
| (6-CH$_3$)pyridin-3-yl | N1-[Me$_2$N(CH$_2$)$_3$] | H | H; |
| 2-pyridinyl | N1-[Me$_2$N(CH$_2$)$_3$] | H | H; |
| 4-pyridinyl | N1-[Me$_2$N(CH$_2$)$_3$] | H | 5-Cl; |
| (5-Br)pyridin-2-yl | N1-[Me$_2$N(CH$_2$)$_3$] | H | H; |
| Me$_2$N(CH$_2$)$_3$ | N1-3-pyridinyl | H | H; |
| 6-quinolinyl | N1-[Me$_2$N(CH$_2$)$_3$] | H | H; |
| 2-quinolinyl-CH$_2$ | N1-[Me$_2$N(CH$_2$)$_3$] | H | 6-Cl; |
| 3-pyridinyl | N1-[HO(CH$_2$)$_2$O(CH$_2$)$_2$] | H | H; |
| 3-quinolinyl | N1-[HO(CH$_2$)$_3$] | H | H; |
| 3-pyridinyl | N1-[H$_2$N(CH$_2$)$_3$] | H | H; |
| 3-pyridinyl | N1-[HO(CH$_2$)$_2$] | H | H; |
| 3-pyridinyl | N1-[HO(CH$_2$)$_4$] | H | H; |
| 3-pyridinyl | N1-[OHC(CH$_2$)$_2$] | H | 5-OMe; |
| 3-pyridinyl | N1-[HO$_2$C(CH$_2$)$_2$] | H | H; |
| 3-pyridinyl | N1-[(HOCH$_2$CH$_2$)MeN(CH$_2$)$_3$] | H | H; |
| 3-pyridinyl | N1-[MeO(CH$_2$)$_2$] | H | H; |
| 3-pyridinyl | H | H | H |
| 3-pyridinyl and | N1-[[AcO(CH$_2$)$_3$] | H | H; |
| 3-pyridinyl | N2-[HO(CH$_2$)$_3$] | H | H; | and a pharmaceutically acceptable salt thereof.

18. The compound of claim 1 wherein the compound of Formula (I) is a compound selected from Formula (Ib):

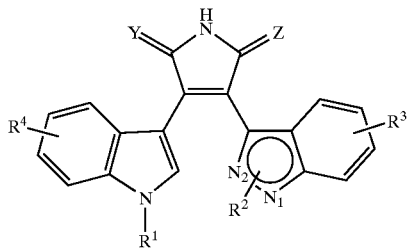

Formula (Ib)

wherein Y, Z, $R^1$, $R^2$, $R^3$ and $R^4$ are dependently selected from the group consisting of:

| Y | Z | $R^1$ | $R^2$ | $R^3$ | $R^4$ |
|---|---|---|---|---|---|
| H, H | O | 2-pyridinyl | N1-[$Me_2N(CH_2)_3$] | H | H; | and a pharmaceutically acceptable salt thereof.

19. The compound of claim 1 wherein the compound of Formula (I) is a compound selected from Formula (Ic):

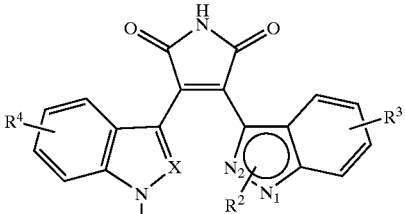

Formula (Ic)

wherein X, $R^1$, $R^2$, $R^3$, $R^4$ and $R^5$ are dependently selected from the group consisting of:

| X | $R^1$ | $R^2$ | $R^3$ | $R^4$ | $R^5$ |
|---|---|---|---|---|---|
| C-$R^5$ and | 3-pyridinyl | N1-[$Me_2N(CH_2)_3$] | H | H | 2-naphthyl; |
| C-$R^5$ | 3-pyridinyl | N1-[$Me_2N(CH_2)_3$] | H | 5-Cl | $CH_3$; | and a pharmaceutically acceptable salt thereof.

20. A pharmaceutical composition comprising a compound of claim 1 and a pharmaceutically acceptable carrier.

* * * * *